(12) United States Patent
Kara et al.

(10) Patent No.: US 10,584,166 B2
(45) Date of Patent: Mar. 10, 2020

(54) LIGANDS THAT POTENTIATE THE BIOACTIVITY OF GONADOTROPINS

(71) Applicant: Repropharm, Nouzilly (FR)

(72) Inventors: Elodie Kara, Veigne (FR); Jeremye Decourtye, Tours (FR); Sophie Casteret, Valleres (FR); Marie-Christine Maurel, Tours (FR)

(73) Assignee: REPROPHARM VET, Nouzilly (FR)

( * ) Notice: Subject to any disclaimer, the term of this patent is extended or adjusted under 35 U.S.C. 154(b) by 0 days.

(21) Appl. No.: 15/510,640

(22) PCT Filed: Sep. 10, 2015

(86) PCT No.: PCT/FR2015/052414
§ 371 (c)(1),
(2) Date: Mar. 10, 2017

(87) PCT Pub. No.: WO2016/038309
PCT Pub. Date: Mar. 17, 2016

(65) Prior Publication Data
US 2017/0190774 A1    Jul. 6, 2017

(30) Foreign Application Priority Data

Sep. 10, 2014   (FR) .................................... 14 58469
Aug. 31, 2015   (FR) .................................... 15 58078

(51) Int. Cl.
*C07K 16/26* (2006.01)
*A61K 39/00* (2006.01)

(52) U.S. Cl.
CPC ........ *C07K 16/26* (2013.01); *A61K 2039/505* (2013.01); *C07K 2317/14* (2013.01); *C07K 2317/33* (2013.01); *C07K 2317/54* (2013.01); *C07K 2317/55* (2013.01); *C07K 2317/56* (2013.01); *C07K 2317/565* (2013.01); *C07K 2317/569* (2013.01); *C07K 2317/622* (2013.01); *C07K 2317/624* (2013.01); *C07K 2317/626* (2013.01); *C07K 2317/70* (2013.01); *C07K 2317/75* (2013.01); *C07K 2317/92* (2013.01)

(58) Field of Classification Search
None
See application file for complete search history.

(56) References Cited

U.S. PATENT DOCUMENTS

| 2002/0102613 A1 | 8/2002 | Hoogenboom |
| 2013/0243795 A1 | 9/2013 | Chen et al. |
| 2017/0190773 A1 | 7/2017 | Kara et al. |

FOREIGN PATENT DOCUMENTS

| EP | 1518863 A1 | 3/2005 | |
| WO | WO 94/05690 * | 3/1994 | ............ C07H 21/02 |
| WO | 9712038 A1 | 4/1997 | |
| WO | WO 2007/030930 * | 3/2007 | ............ C12N 15/13 |
| WO | 2012066519 A1 | 5/2012 | |

OTHER PUBLICATIONS

Bernauer et al. "A new protein-protein docking scoring function based on interface residue properties" Bioinformatics; 2007; vol. 23(5); pp. 555-562.
Bernauer et al. "A Voronoi tessellation-based method for discriminating crystallographis and biological protein-protein interactions"; Structural Bioinformatics; 2008; vol. 24(5); pp. 652-658.
Bourquard et al. "A Collaborative Filtering Approach for Protein-Protein Docking Scoring Functions" PLoS One; 2011; 6(4); e18541.
Bourquard et al. Unraveling the molecular architecture of a G protein-coupled receptor / B-arrestin/ Erk module complex; Scientific Reports; 2015; 5:10760.
Brochet et al IMGT/V-Quest: the highly customized and integrated system for IG and TR standardized V-J and V-D-J sequence analysis; Nuc. Acids Res.; 2008; vol. 26; W503-W508.
Chopineau et al. "Topography of equine chorionic gonadotropin epitopes relative to the luteinizing hormone and follicle-stimulating hormone receptor interaction sites" Mol. Cell. Endocrinol; 1993; 92(2); 229-239.
Corpet "Multiple sequence alignment with hierarchical clustering" Nucl. Acids Res.; 1988; vol. 16(22); 10881-10890.
Fan et al. "Structure of human follicle-stimulating hormone in complex with its receptor" Nature; 2005; 433; 269-277.
Giudicelli et al "INGT/GENE-DB: a comprehensive database for human and mouse immunoglobulin and T cell receptor genes" Nucl. Acids Res.; 2005; vol. 33; D256-D261.
Giudicelli et al. "IMGT/V-QUEST: IMGT Standarized Analysis of the Immunoglobulin (IG) and T Cell Receptor (TR) Nucleotide Sequences" Cold Spring Harb Protoc.; 2011; 2011(6) 695-715.
Glencross et al. "Monoclonal antibody enhancement of OSH-induced uterine growth in snell dwarf mice" Journal of Endocrinology, Society for Endocrinology, BG, vol. 136, No. 3, Mar. 1, 1993, pp. R5-R7, XP009145848.
International Preliminary Report on Patentability; Application No. PCT/FR2015/052414; International Filing Date Sep. 9, 2015, dated Jan. 2, 2017, 5 pages;Non-English Translation.
International Preliminary Report on Patentability; Application No. PCT/FR2015/052414; International Filing Date Sep. 9, 2015, dated Jan. 2, 2017, 7 pages; English Translation.
International Search Report; International Application No. PCT/FR2015/052414; International Filing Date Sep. 10, 2015; dated Dec. 15, 2015, 3 pages; English Translation.
International Search Report;International Application No. PCT/FR2015/052414; International Filing Date Sep. 10, 2015; dated Nov. 12, 2015, 5 pages; Non-English Translation.
Li et al. "An improved calcium chloride method preparation and transformation of competent cells" African Journal of Biotechnology; 2010; vol. 9(50); pp. 2549-2554.

(Continued)

*Primary Examiner* — Christina M Borgeest
(74) *Attorney, Agent, or Firm* — Cantor Colburn LLP

(57) ABSTRACT

The invention relates to antibodies directed against follicle-stimulating hormone (FSH) and capable of potentiating the bioactivity of gonadotropins.

29 Claims, 26 Drawing Sheets
Specification includes a Sequence Listing.

(56) References Cited

OTHER PUBLICATIONS

Miller K F et al. "Immunoaffinity chromatography of bovine FSH using monoclonal antibodies" Database Medline (Online), US National Library of Medicine, Bethesda, MD, US; Nov. 1987, XP002751132, Database accession No. NLM3125301.
Reverchon et al. Chemerin inhibits IGF-I-induced progesterone and estradiol secretion in human granulosa cells; Human Reproduction; 2012; 27(6); pp. 1790-1800.
Scobey et al Mixed protocols: Multiple ratios of FSH and KH bioactivity using highly purified, human-derived FSH (BRAVEKKE) and highly purified hMG (MENOPUR) are unaltered by mixing together in the same syringe; Reproductive Biology and Endocrinology; 2005; 3; 61.
Steelman et al. "Assay of the Follucle Stimulating Hormone based on the Augmentation with Human Chorionic Gonadotropin" Endocrinology; 1953; 53; 604-616.
Ulloa-Aguirre et al. "Novel pathways in gonadotropin recertor signaling and biased agonism" Reviews in Endocrine and Metabolic Disorders, Kluwer Academic Publishers, BO, vol. 12, No. 4, Apr. 28, 2011, pp. 259-274, XP019972343.
Ward et al. "Binding activities of a repertoire of single immunoglobulin variable domains secreted from *Escherichia coil*" Nature; 1989; 341; 544-546.
Wehbi et al. Selective Modulation of Follicle-Stimulating Hormone Signaling Pathways with Enhancing Equine Chorionic Gonadotropin/ANtibody Immune Complexes; Endocrinology; 2010; 151(6); 2788-2799.
Written Opinion of the International Searching Authority; International Application No. PCT/FR2015/052414; International Filing Date Sep. 9, 2015; dated Mar. 17, 2016, 6 pages; Non-English Translation.
Bhattacharya et al "Impact of genetic variation on three dimensional structure and function of proteins"; PLOS ONE; 2017; 12(3); pp. 1-22; https://doi.org/10.1371/journal.pone.0171355.
Johnson & Everett in Essential Reproduction, Fifth Edition, 2000; Blackwell Science Ltd,. Chapter 15, "Fertility", pp. 265-271.

\* cited by examiner

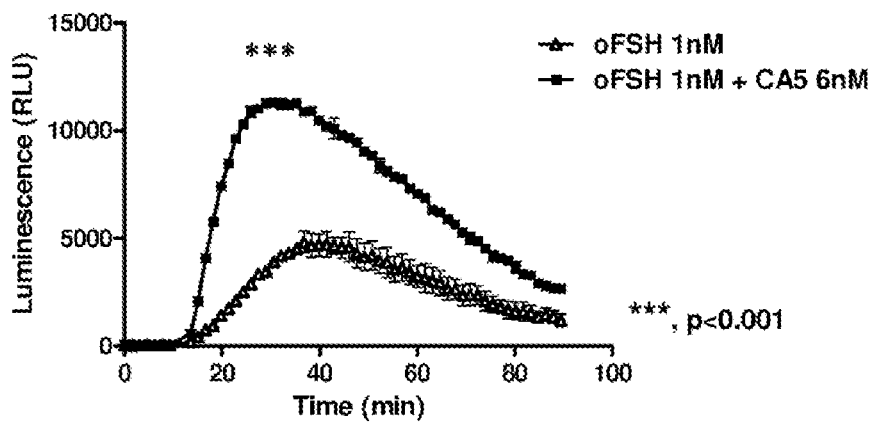
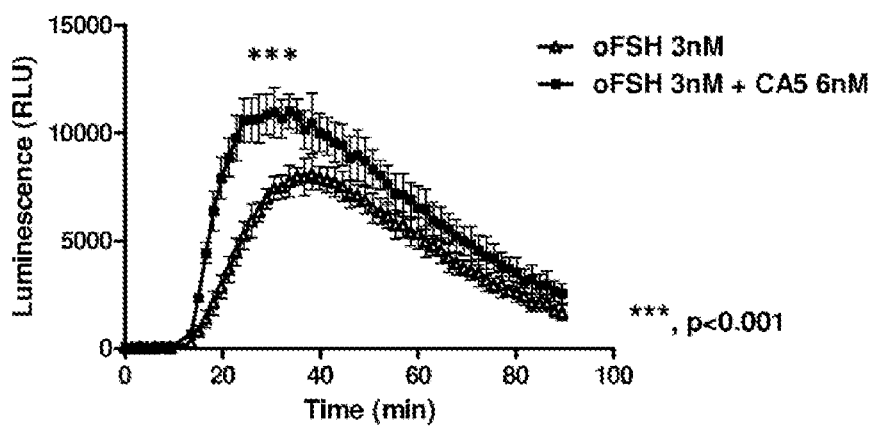
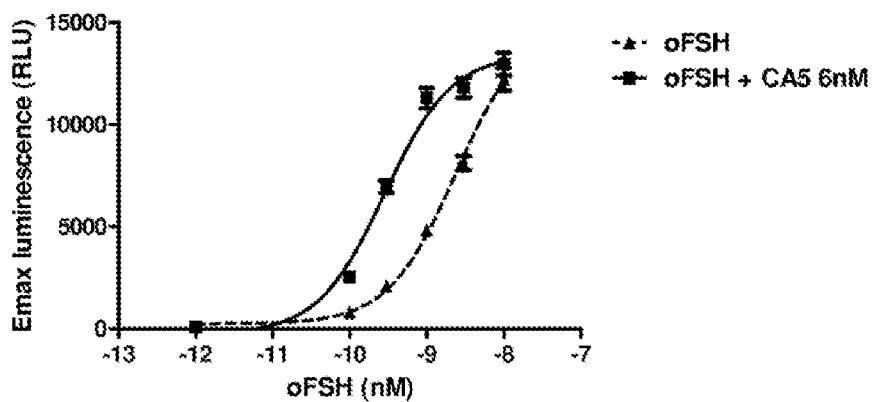
FIGURE 3 (end)

D 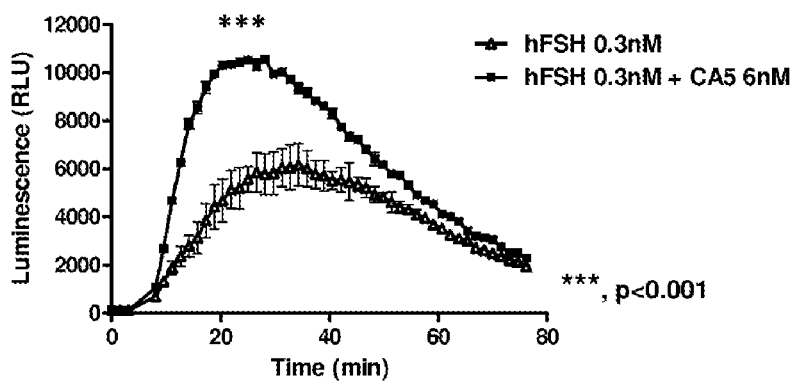
E 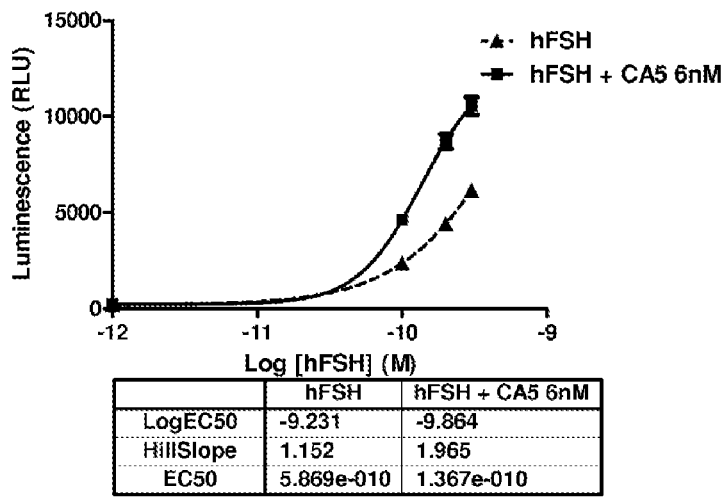
F 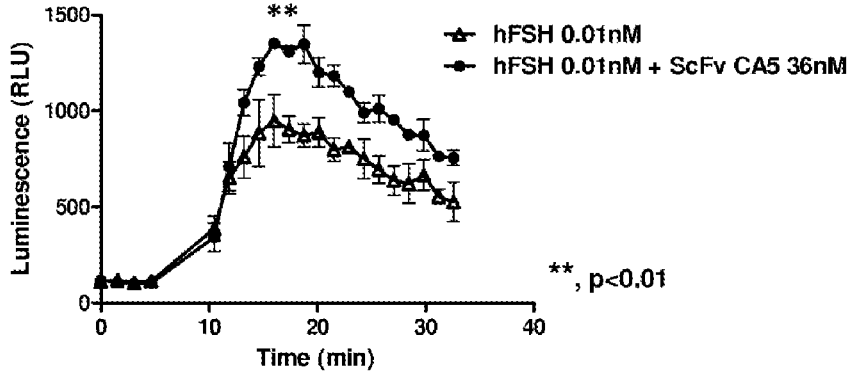
Figure 5 (end)

A

CA5 / FSH : **, $p<0.01$
CA5 or FSH / serum Φ : ***, $p<0.001$

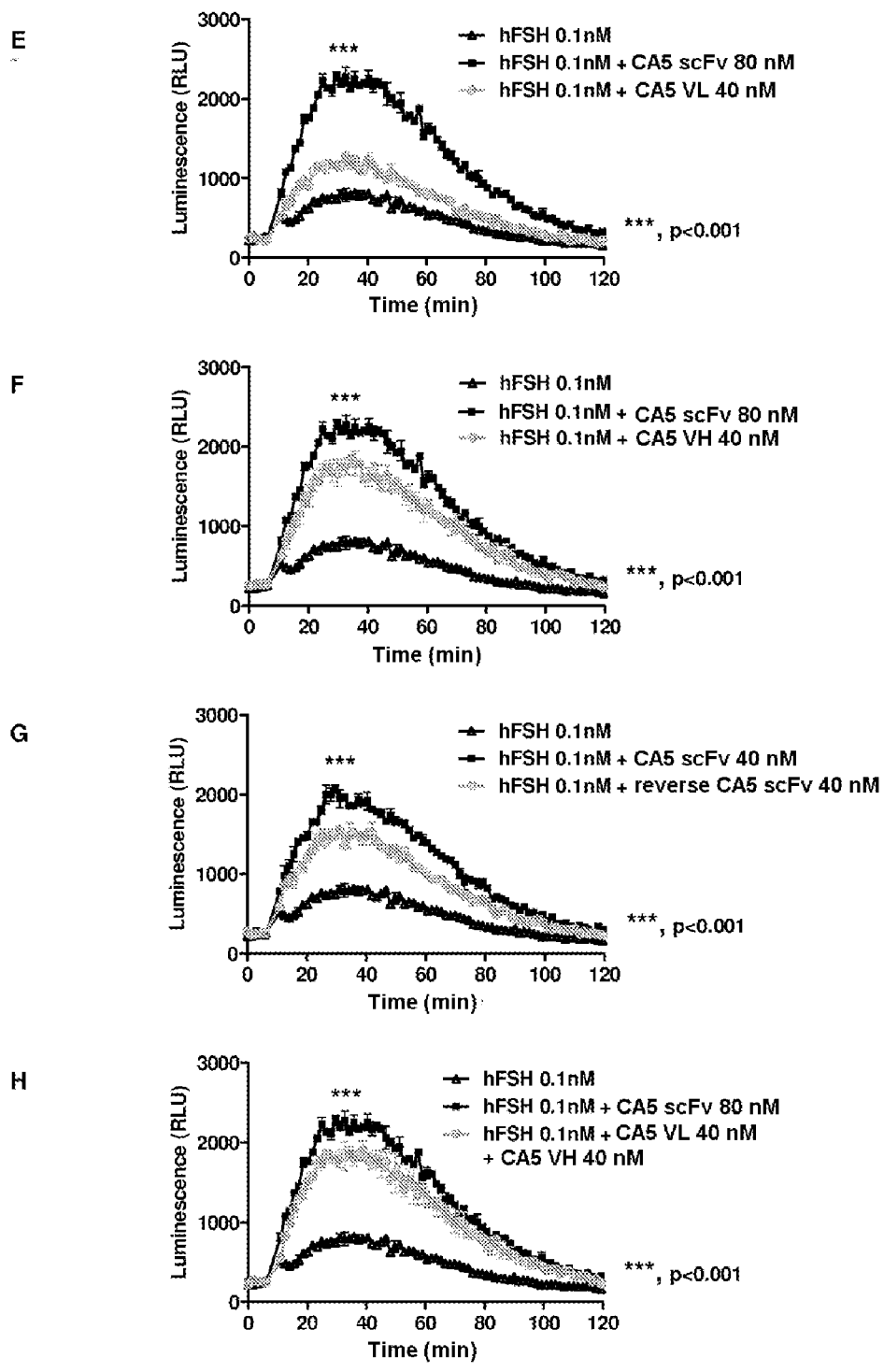
FIGURE 22 (end)

LIGANDS THAT POTENTIATE THE BIOACTIVITY OF GONADOTROPINS

CROSS REFERENCE TO RELATED APPLICATIONS

This is a U.S. national stage of application No. PCT/FR2015/052414, filed on Sep. 10, 2015. Priority under 35 U.S.C. § 119(a) and 35 U.S.C. § 365(b) is claimed from French Application No. 1458469 filed on Sep. 10, 2014 and French Application No. 1558078 filed on Aug. 31, 2015, the disclosure of which is also incorporated herein by reference in its entirety.

TECHNICAL FIELD

The present invention relates to antibodies directed against follicle-stimulating hormone (FSH) and capable of potentiating the bioactivity of gonadotropins.

The present invention has its applications mainly in human and veterinary medicine, for inducing ovulation in a female mammal.

In the description below, the references between square brackets ([ ]) refer to the list of references presented at the end of the text.

BACKGROUND

Gonadotropins (or gonadotrophins) are complex glycoprotein hormones which play a central role in the regulation of reproduction in vertebrates by acting on the functions of the gonads (ovaries and testicles). Two of these hormones are secreted in all vertebrates: luteinizing hormone (LH) and follicle-stimulating hormone (FSH). In two groups of mammals, members of the horse family and primates, there is also a chorionic gonadotropin (CG) secreted by the placenta: human chorionic gonadotropin (hCG) and equine chorionic gonadotropin (eCG) which both act via LH receptors.

Luteinizing hormone (LH) is produced by the gonadotropic cells of the anterior lobe of the pituitary gland under stimulation from GnRH, itself produced by the hypothalamus. LH stimulates testosterone production in males, whereas it is involved in modifications of the ovarian cycle in females where it is responsible for terminal follicular growth and for ovulation and then for conversion of the ruptured ovulatory follicle into the corpus luteum. During the luteal phase of the menstrual cycle, LH stimulates progesterone secretion by the corpus luteum, essential for the early development and implantation of the embryo. LH consists of an α-subunit common to all the glycoprotein hormones of one and the same species (such as FSH, CG and thyroid-stimulating hormone, TSH), and of a β-subunit responsible for the specificity of activity of the hormone; activity which exists only if the two subunits are noncovalently linked in the form of a dimer.

Follicle-stimulating hormone (or FSH) is produced by the anterior pituitary gland under stimulation from GnRH produced by the hypothalamus. In males, it stimulates the Sertoli cells essential for spermatogenesis. In females, it is responsible for the recruitment of immature primordial follicles, for their growth and for their differentiation into pre-ovulatory follicles by stimulating the FSH receptors of the granulosa cells. FSH consists of two subunits, α and β, and has a structure similar to that of LH. Only the dimer is capable of stimulating FSH receptors.

In females, the LH and FSH levels are cyclical: very low during the period of sexual rest or outside the ovulatory period, with a secretion peak in the preovulatory period.

Gonadotropins are used in veterinary and human medicine, to induce ovulation in female mammals. Although effective, these treatments present a health risk because of the use of hormones extracted from biological fluids (blood, urine) or from tissues (pituitary glands), particularly in the veterinary field. This is the case with equine chorionic gonadotropin (eCG) extracted from gravid mare blood, and with a porcine LH and FSH extracted from pig pituitary glands. In the veterinary field, an hCG extracted from urine from pregnant women, Chorulon® (MSD laboratory), is also used.

In the human clinical field, and particularly the field of Assisted Reproductive Technology (or ART), hormones extracted from urine from menopausal women, such as Fostimon® (Laboratoire Genévrier) which is a purified FSH, and Menopur® (Ferring Pharmaceuticals laboratory), which is an hMG (human menopausal gonadotropin), a mixture of FSH and LH and the chorionic gonadotropin Endo5000, which is a purified hCG (Schering-Plough laboratory), are used. Use is also made of recombinant human FSHs, such as Gonal-F® (Merck Serono laboratory) and Puregon® (Merck Schering-Plough laboratory); and recombinant hCG and LH such as Ovidrel® and Luveris® (Merck Serono laboratory).

In addition, repeated use of these hormones usually causes an immune reaction which neutralizes the effect of the hormones, thus resulting in a decrease in therapeutic efficacy. However, it has also been demonstrated in some cases that the immune reaction can produce antibodies capable of potentiating the activity of the hormone when it is co-administered (patent EP 1 518 863) [1]. Since then, three anti-LH monoclonal antibodies capable of potentiating its action, and also that of FSH for two of them, have also been demonstrated (international application WO 2012/066519) [2].

SUMMARY

The inventors have now obtained monoclonal antibodies produced against the β-subunit of FSH, which are capable of potentiating its action and also that of LH and of hCG.

These monoclonal antibodies are respectively called CA5 and CH10.

The hybridoma which produced the CA5 antibody was deposited, in accordance with the Treaty of Budapest, on Oct. 3, 2013 with the CNCM (Collection Nationale de Culture de Microorganismes [French National Collection of Microorganism Cultures], Institut Pasteur, 25 rue du Docteur Roux, 75724 Paris Cedex 15, France), under number CNCM I-4801.

The hybridoma which produced the CH10 antibody was deposited, in accordance with the Treaty of Budapest, on Oct. 3, 2013 with the CNCM (Collection Nationale de Culture de Microorganismes [French National Collection of Microorganism Cultures], Institut Pasteur, 25 rue du Docteur Roux, 75724 Paris Cedex 15, France), under number CNCM I-4802.

The nucleotide sequences of the heavy and light chain variable regions of the CA5 and CH10 antibodies have been determined, and the corresponding peptide sequences have been deduced. They are presented respectively in tables 1 and 2 below.

TABLE 1

CA5 monoclonal antibody

Heavy chain (VH)

| | |
|---|---|
| Nucleotide sequence (SEQ ID NO: 1) | GAGGTGAAGCTGGTGGAATCTGGAGGAGGCTTGGTACAGCCT GGGGGTTCTCTGAGACTCTCCTGTGCAACTTCTGGGTTCACCTT CAGTGATTTCTACATGGAGTGGGTCCGCCAGCCTCCAGGGAAG AGACTGGAGTGGATTGCTGCAAGTAGAAACAAAGCTAAGGATT ATACAACAGAGTACAGTGCATCTGTGAAGGGTCGGTTCATCGT CTCCAGAGACACTTCCCAAAGCATCCTCTACCTTCAGATGAATG CCCTGAGAGCTGAGGACACTGCCATTTATTTCTGTGCAAGAGAT GCAAGGTTTGCTTACTGGGGCCAAGGGACTCTGGTCACTGTCT CTGCA |
| Peptide sequence (SEQ ID NO: 2) | EVKLVESGGGLVQPGGSLRLSCATSGFTFSDFYMEWVRQPPGKR LEWIAASRNKAKDYTTEYSASVKGRFIVSRDTSQSILYLQMNALRA EDTAIYFCARDARFAYWGQGTLVTVSA |

Light chain (VL)

| | |
|---|---|
| Nucleotide sequence (SEQ ID NO: 3) | GACATTGTGATGTCACAGTCTCCATCCTCCCTAGCTGTGTCAGT TGGAGAGAAGATTACTATGAGCTGCAAGTCCAGTCAGAGCCTTT TATATAGTAGCAATCAAAAGAACTACTTGGCCTGGTACCAGCAG AAACCAGGGCAGTCTCCTAAACTGCTGATTTACTGGGCATCCAC TAGGGAATCTGGGGTCCCTGATCGCTTCACAGGCAGTGGATCT GGGACAGATTTCACTCTCACCATCAGCAGTGTGAAGGCTGAAG ACCTGGCAGTTTATTACTGTCAGCAATATTATAGCTATCCTCGG ACGTTCGGTGGAGGCACCAAGCTGGAAATCAAA |
| Peptide sequence (SEQ ID NO: 4) | DIVMSQSPSSLAVSVGEKITMSCKSSQSLLYSSNQKNYLAWYQQK PGQSPKLLIYWASTRESGVPDRFTGSGSGTDFTLTISSVKAEDLAV YYCQQYYSYPRTFGGGTKLEIK |

TABLE 2

CH10 monoclonal antibody

Heavy chain (VH)

| | |
|---|---|
| Nucleotide sequence (SEQ ID NO: 5) | GAGGTGCAGCTTGTTGAGTCTGGTGGAGGATTGGTGCAGCCTA AAGGGTCATTGAAACTCTCATGTGCAGCCTCTGGATTCACCTTC AATACCTACGCCATGAACTGGGTCCGCCAGGCTCCAGGAAAGG GTTTGGAATGGGTTGCTCGCATAAGAAGTAAAAGTAATAATTAT GCAACATATTATGCCGATTCAGTGAAAGACAGGTTCACCATCTC CAGAGATGATTCACAAAGCATGCTCTATCTGCAAATGAACAACT TGAAAACTGAGGACACAGCCATGTATTACTGTGTGAGACAGGAT TACTACGGTAGTAGCTACTTTGACTACTGGGGCCAAGGCACCA CTCTCACAGTCTCCTCA |
| Peptide sequence (SEQ ID NO: 6) | EVQLVESGGGLVQPKGSLKLSCAASGFTFNTYAMNWVRQAPGKG LEWVARIRSKSNNYATYYADSVKDRFTISRDDSQSMLYLQMNNLK TEDTAMYYCVRQDYYGSSYFDYWGQGTTLTVSS |

Light chain (VL)

| | |
|---|---|
| Nucleotide sequence (SEQ ID NO: 7) | GACATTGTGATGACTCAGTCTCCAGCCACCCTGTCTGTGACTCC AGGAGATAGAGTCTCTCTTTCCTGCAGGGCCAGCCAGAGTATT AGCGACTACTTACACTGGTATCAACAAAAATCACATGAGTCTCC AAGGCTTCTCATCAAATATGCTTCCCAATCCATCTCTGGGATCC CCTCCAGGTTCAGTGGCAGTGGATCAGGGTCAGATTTCACTCT CAGTATCAACAGTGTGGAACCTGAAGATGTTGGAGTGTATTACT GTCAAAATGGTCACAGCTTTCCGTACACGTTCGGAGGGGGGAC CAAGCTGGAAATAAAA |
| Peptide sequence (SEQ ID NO: 8) | DIVMTQSPATLSVTPGDRVSLSCRASQSISDYLHWYQQKSHESPR LLIKYASQSISGIPSRFSGSGSGSDFTLSINSVEPEDVGVYYCQNG HSFPYTFGGGTKLEIK |

The sequences encoding the CDRs (complementarity determining regions) have been determined from the sequences of the variable regions of the heavy (VH-CDR) and light (VL-CDR) chains of the CA5 and CH10 antibodies above. The corresponding peptide sequences have been deduced and are presented respectively in tables 3 and 4 below.

TABLE 3

| CA5 monoclonal antibody | | |
|---|---|---|
| VH-CDR1 | (SEQ ID NO: 9) | GFTFSDFY |
| VH-CDR2 | (SEQ ID NO: 10) | SRNKAKDYTT |

TABLE 3-continued

CA5 monoclonal antibody

| | |
|---|---|
| VH-CDR3 (SEQ ID NO: 11) | ARDARFAY |
| VL-CDR1 (SEQ ID NO: 12) | QSLLYSSNQKNY |
| VL-CDR2 | WAS |
| VL-CDR3 (SEQ ID NO: 13) | QQYYSYPRT |

TABLE 4

CH10 monoclonal antibody

| | |
|---|---|
| VH-CDR1 (SEQ ID NO: 14) | GFTFNTYA |
| VH-CDR2 (SEQ ID NO: 15) | IRSKSNNYAT |
| VH-CDR3 (SEQ ID NO: 16) | VRQDYYGSSYFDY |
| VL-CDR1 (SEQ ID NO: 17) | QSISDY |
| VL-CDR2 | YAS |
| VL-CDR3 (SEQ ID NO: 18) | QNGHSFPYT |

A subject of the present invention is a follicle-stimulating hormone (FSH) ligand which potentiates the bioactivity of FSH, of luteinizing hormone (LH) and of chorionic gonadotropin (CG), characterized in that it comprises the paratope of an anti-FSH β-subunit antibody.

For the purposes of the present invention, the term "anti-FSH β-subunit antibody" is intended to mean any antibody obtained by immunization of an animal on the basis of primary injections of FSH followed by several boosters with injection of the FSH β-subunit. The injections can be given using FSH from various mammals, for example ovine, human, bovine, caprine or porcine, equine, canine, murine, etc., FSH and β-subunits of FSH of homologous or heterologous origin. Thus, the CA5 and CH10 monoclonal antibodies were obtained following an immunization using ovine FSH and ovine FSH β-subunit.

In particular, a subject of the present invention is thus a ligand according to the invention, characterized in that:

the heavy chain variable domain contains the following CDRs:
VH-CDR1, defined by the sequence GFTFSDFY (SEQ ID NO: 9);
VH-CDR2, defined by the sequence SRNKAKDYTT (SEQ ID NO: 10);
VH-CDR3, defined by the sequence ARDARFAY (SEQ ID NO: 11); and
the light chain variable domain contains the following CDRs:
VL-CDR1, defined by the sequence QSLLYSSNQKNY (SEQ ID NO: 12);
VL-CDR2, defined by the sequence WAS;
VL-CDR3, defined by the sequence QQYYSYPRT (SEQ ID NO: 13).

In particular, a subject of the present invention is thus a ligand according to the invention, characterized in that:

the heavy chain variable domain contains the following CDRs:
VH-CDR1, defined by the sequence GFTFNTYA (SEQ ID NO: 14);
VH-CDR2, defined by the sequence IRSKSNNYAT (SEQ ID NO: 15);
VH-CDR3, defined by the sequence VRQDYYGSSYFDY (SEQ ID NO: 16); and
the light chain variable domain contains the following CDRs:
VL-CDR1, defined by the sequence QSISDY (SEQ ID NO: 17);
VL-CDR2, defined by the sequence YAS;
VL-CDR3, defined by the sequence QNGHSFPYT (SEQ ID NO: 18).

For the purposes of the present invention, the term "CDR" is intended to mean the three hypervariable regions of the variable regions of the heavy and light chains of an antibody which constitute the elements of the paratope and make it possible to determine the complementarity of the antibody with the epitope of the antigen. These three hypervariable regions are framed by four constant regions which constitute the "framework" regions (FRs) and give the variable domain a stable configuration.

A ligand according to the present invention is for example:
the CA5 monoclonal antibody produced by the CNCM I-4801 hybridoma;
the CH10 monoclonal antibody produced by the CNCM I-4802 hybridoma;
a Fab, Fab', F(ab')2, Fv, dsFv or scFv fragment or a nanobody of an antibody above. Preferably, it is a Fab fragment or an scFv fragment;
a bivalent, trivalent or tetravalent form (diabodies, triabodies, tetrabodies) of two, three or four scFv fragments, respectively;
a recombinant antibody comprising the paratope of an antibody above and the constant regions of which have been modified so as to minimize the immunogenicity with respect to the animal or the human being for which it is intended. For example, it is a chimeric (humanized, ovinized, caprinized, bovinized, porcinized, etc.) or entirely humanized, ovinized, caprinized, bovinized, porcinized antibody.

By way of nonlimiting example, the nucleotide sequences of scFvs derived from the CA5 and CH10 antibodies have been determined, and the corresponding peptide sequences deduced, and are presented respectively in tables 5 and 6 below.

TABLE 5

CA5 scFv

| | |
|---|---|
| Nucleotide sequence (SEQ ID NO: 19) | CAGGTGCAGCTGCAGCAGTCAGGCGGCGGCCTGGTACA ACCTGGTGGCTCACTGCGCCTGAGCTGCGCAACCAGCG GTTTTACCTTTAGCGATTTCTACATGGAATGGGTTCGC CAACCGCCGGGTAAGCGTCTGGAATGGATCGCGGCGAG CCGTAACAAGGCGAAAGATTATACCACTGAATATAGCG CGTCGGTGAAAGGTCGCTTCATTGTCTCGCGCGATACC AGCCAGTCGATTCTGTATCTGCAAATGAATGCCCTGCG TGCCGAAGACACGGCCATCTACTTCTGTGCGCGTGATG CACGCTTTGCCTATTGGGGCCAAGGCACCCTGGTGACC GTTAGCGCCGGTGGTGGCGGTTCAGGTGGTGGCGGTAG CGGTGGCGGTGGCTCAGATATTCAGATGACCCAGACCC CGTCAAGCCTGGCGGTGTCAGTCGGCGAAGAGATTACT ATGAGCTGTAAAAGCTCGCAGAGCCTGCTGTACTCATC GAACCAGAAAAATTACCTGGCATGGTATCAACAGAAGC CGGGTCAGTCGCCGAAACTGCTGATCTACTGGGCCTCA ACCCGTGAGAGCGGCGTACCGGATCGCTTTACTGGCAG CGGCAGCGGCACGGACTTTACGCTGACGATTAGCTCGG TGAAGGCCGAAGACCTGGCGGTTTATTATTGCCAACAG TACTATAGCTACCCTCGTACCTTCGGCGGCGGCACGAA ACTCGAGATTAAACATCACCATCACCATCACTAACTCG AGATCAAGTAA |

TABLE 5-continued

CA5 scFv

| | |
|---|---|
| Peptide sequence (SEQ ID NO: 20) | QVQLQQSGGGLVQPGGSLRLSCATSGFTFSDFYMEWVR QPPGKRLEWIAASRNKAKDYTTEYSASVKGRFIVSRDT SQSILYLQMNALRAEDTAIYFCARDARFAYWGQGTLVT VSAGGGGSGGGGSGGGGSDIQMTQTPSSLAVSVGEEIT MSCKSSQSLLYSSNQKNYLAWYQQKPGQSPKLLIYWAS TRESGVPDRFTGSGSGTDFTLTISSVKAEDLAVYYCQQ YYSYPRTFGGGTKLEIKHHHHHH |

TABLE 6

CH10 scFv

| | |
|---|---|
| Nucleotide sequence (SEQ ID NO: 21) | CAGGTGCAGCTGCAGCAATCAGGCGGCGGCCTGGTCCA ACCGAAAGGTAGCCTGAAACTGTCGTGCGCCGCCAGCG GCTTTACGTTCAACACTTACGCGATGAATTGGGTGCGT CAGGCGCCTGGTAAAGGCCTGGAATGGGTGGCACGCAT CCGTTCAAAAAGCAACAATTACGCGACGTATTATGCAG ACAGCGTAAAAGATCGCTTTACCATCAGCCGTGATGAT TCACAGTCAATGCTGTACCTGCAAATGAATAACCTGAA AACTGAAGACACTGCGATGTATTATTGTGTTCGCCAGG ACTATTACGGTAGCTCGTATTTCGATTACTGGGGCCAA GGCACCACCCTGACGGTGAGCTCGGGTGGCGGTGGCTC AGGTGGTGGTGGTAGCGGCGGTGGCGGTAGCGATATCC AGATGACCCAGA CCCCGGCAACCCTGAGCGTTACCCC TGGTGACCGCGTTTCGCTGAGCTGCCGTGCCTCGCAGA GCATTTCGGACTATCTGCACTGGTATCAGCAAAAATCA CACGAATCACCGCGTCTGCTGATTAAGTACGCCAGCCA ATCGATTAGCGGTATTCCGAGCCGCTTTTCGGGCTCGG GTTCGGGCTCGGATTTTACCCTGTCAATTAATAGCGTA GAGCCGGAAGATGTAGGCGTCTACTATTGTCAGAACGG CCATTCATTCCCGTACACGTTTGGCGGCGGCACCAAGC TCGAGATTAAGCATCACCATCATCACCATTAACTCGAG ATCAAGTAA |
| Peptide sequence (SEQ ID NO: 22) | QVQLQQSGGGLVQPKGSLKLSCAASGFTFNTYAMNWVR QAPGKGLEWVARIRSKSNNYATYYADSVKDRFTISRDD SQSMLYLQMNNLKTEDTAMYYCVRQDYYGSSYFDYWGQ GTTLTVSSGGGGSGGGGSGGGGSDIQMTQTPATLSVTP GDRVSLSCRASQSISDYLHVVYQQKSHESPRLLIKYAS QSISGIPSRFSGSGSGSDFTLSINSVEPEDVGVYYCQN GHSFPYTFGGGTKLEIKHHHHHH |

A subject of the present invention is also a nucleotide sequence encoding a ligand according to the invention.

A subject of the present invention is also a recombinant vector, in particular an expression vector, comprising a nucleotide sequence according to the invention.

A subject of the present invention is also a host cell comprising a nucleotide sequence according to the invention or a recombinant vector according to the invention. For example, it is the CNCM I-4801 and CNCM I-4802 hybridomas or a cell transformed with a nucleotide sequence or a recombinant vector according to the invention.

A subject of the present invention is also a method for producing a ligand according to the invention, characterized in that it comprises culturing host cells according to the invention in an appropriate medium, and recovering said ligand from said culture.

The inventors have demonstrated that the CA5 antibody strongly potentiates porcine, ovine and bovine FSH and, to a lesser extent although significantly, human FSH. In addition, the inventors have demonstrated that the scFvs derived from the CA5 and CH10 antibodies have the same binding and potentiating properties as the antibodies from which they are derived.

A subject of the present invention is also a ligand according to the invention for use as a medicament, in particular for potentiating the bioactivity of FSH, of LH and of chorionic gonadotropin (CG) for inducing ovulation in a female mammal and for reducing hormone-dependent infertility or hypofertility problems in a male or female mammal.

A subject of the present invention is also a complex formed from a ligand and from a gonadotropin, or from an active peptide thereof, capable of binding to said ligand and the activity of which is potentiated by said ligand. For example, it is the complex of a ligand with LH, with the chorionic gonadotropin (CG) hormone or with FSH which have been extracted from biological tissues or fluids or which are recombinant, or an active peptide of said hormones capable of binding to said ligand and the activity of which is potentiated by said ligand.

A subject of the present invention is also a ligand or complex according to the invention for use as a medicament, in particular for potentiating the bioactivity of FSH, of LH and of chorionic gonadotropin (CG) for inducing ovulation or even polyovulation in a female mammal or for reducing hormone-dependent infertility or hypofertility problems in a male or female mammal. Said medicament also makes it possible to increase the level of circulating endogenous progesterone secreted by one or more corpora lutea in a female mammal, thus promoting early embryonic development and reducing the risk of abortion.

A subject of the present invention is also a method for meat production, wherein said method comprises the administration of ligand and/or of complex of the invention to a non-human animal female mammal.

A subject of the present invention is also a ligand and/or complex of the invention for use in the treatment of hormone-dependent infertility or of hypofertility in a mammal. In the case of a female mammal suffering from infertility or hypofertility, the administration of the ligand or complex of the invention will make it possible to stimulate a natural, medically assisted or artificial procreation. It should be noted that the administration of the ligand or complex of the invention to a healthy female mammal will also make it possible to trigger ovulation in the context of natural or artificial procreation.

For the purposes of the present invention, the term "hormone-dependent infertility/hypofertility" is intended to mean infertility/hypofertility due to hormonal insufficiency, for example low circulating concentrations of FSH and LH or an absence of these hormones resulting, for example, from an external cause (for example pesticides) or an internal cause (for example, pituitary or hypothalamic insufficiency or a problem of gonad receptiveness to LH and/or FSH due to an abnormality of LH, FSH or CG receptors or gonadotropins, for example a receptor mutation or polymorphism).

The ligands and complexes of the invention can be used in humans or animals, in particular members of the ovine, bovine, caprine, equine, porcine, murine, canine, camel, etc. families.

The ligands, the hormones or the complexes according to the invention can be administered either separately, or sequentially, or jointly, by injection, for example intramuscular, intravenous, intraperitoneal, subcutaneous, transcutaneous, intradermal, intraorbital, intraocular or ophthalmic injection, or via the transocular route, without modifying their potentiating effect.

A subject of the present invention is also a pharmaceutical composition comprising a ligand or a complex of the invention and a pharmaceutically acceptable carrier. Said pharmaceutical composition can also comprise an FSH and/or an LH and/or a chorionic gonadotropin (CG) hormone.

Other advantages may further emerge to those skilled in the art on reading the examples below, illustrated by the appended figures, given by way of illustration.

BRIEF DESCRIPTION OF THE FIGURES

FIG. 20 represents the conformational epitope of the CA5 ligand on the hFSH, hCG, hLH, oLH, pLH, oFSH and pFSH hormones and on the human FSH receptor.

FIG. 21 represents the conformational epitope of the CH10 ligand, on the hFSH, hCG, hLH, oLH, pLH, oFSH and pFSH hormones and on the human FSH receptor.

DETAILED DESCRIPTION AND EXAMPLES

Figure 1:
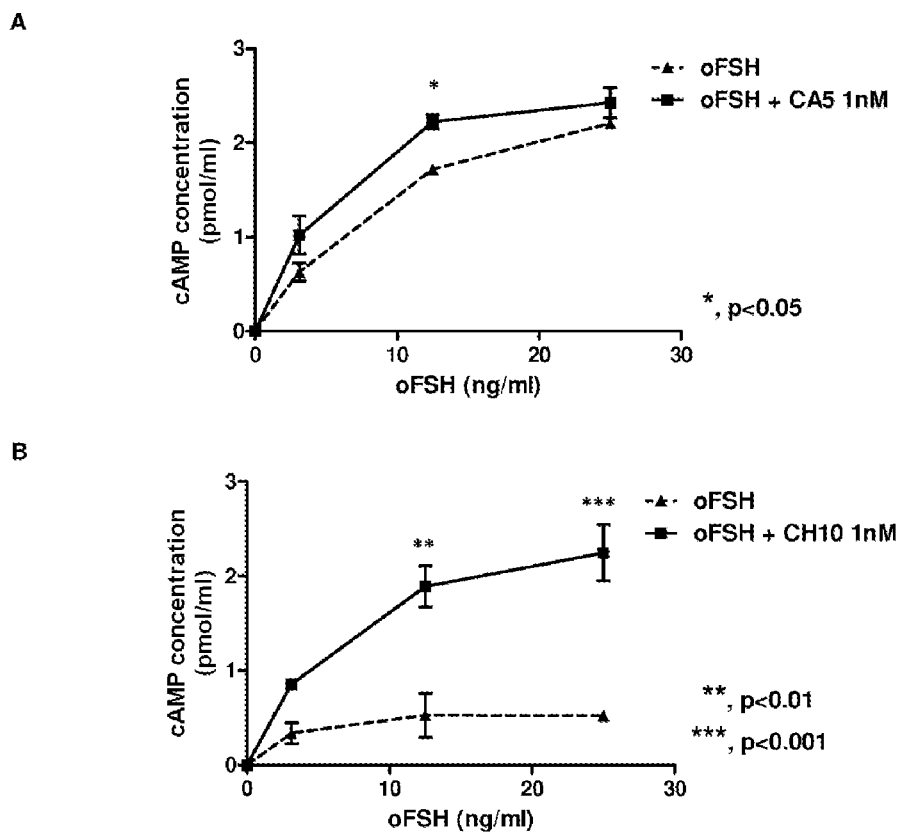
FIG. 1 illustrates the in vitro potentiating effect of the CA5 (A) and CH10 (B) monoclonal antibodies on the bioactivity of ovine FSH (oFSH), on bovine granulosa cells.

Example 1: Obtaining the Ligands of the Invention, and Characterization Thereof

1/Mouse Immunization Strategy

The injections were all carried out intraperitoneally on mice (Balb/C). Five mice were used for each immunization strategy.

Mouse Immunization Strategy for the CA5 Antibody and the CH10 Antibody

A first injection (D0) was carried out with 100 µg of purified ovine FSH with complete Freund's adjuvant. Several booster injections were then carried out according to the following sequence:

D21 and D44: 100 µg of purified ovine FSH with incomplete Freund's adjuvant;

D134 and D204: 50 µg of ovine FSH beta-subunit with incomplete Freund's adjuvant;

D217, D218 and D219: 30 µg of ovine FSH beta-subunit without adjuvant;

D220: fusion.

2/Isotyping

The isotyping of the CA5 and CH10 antibodies was carried out with the FastElysa iostyping kit sold by RD Biotech (reference RDB 3255) according to the manufacturers recommendations.

The CA5 antibody is an immunoglobin of IgG2a class and of Kappa isotype. The optical density (OD) values obtained were 0.335 and 0.371 respectively.

The CH10 antibody is an immunoglobin of IgM class and of Kappa isotype. The optical density (OD) values obtained were 0.2 and 0.124 respectively.

3/Sequencing

The nucleotide sequences of the variable part of the heavy (VH) and light (VL) chains of the CA5 and CH10 antibodies secreted by the CNCM I-4801 and CNCM I-4802 hybridomas respectively, were determined from their messenger RNA (mRNA) according to the protocol below.

The RNAs were extracted from the cells using the Nucleospin® RNA kit (Macherey Nagel, Germany) according to the manufacturer's recommendations. The purified RNA concentrations were estimated by measuring the absorbance (A) at 260 nm and their quality was estimated by the A260 nm/280 nm ratio and visually after electrophoretic migration on an agarose gel.

The complementary DNAs of the mRNAs were then synthesized using an oligo-dT$_{18}$ as primer by reverse transcription reaction with the M-MLV enzyme (Ref. M1701, Promega, USA) according to the manufacturer's recommendations.

The synthesis of the second DNA strand was carried out by a polymerase chain reaction (PCR) according to the following protocol: the following are added to 4 μl of the reverse transcription reaction in a final volume of 50 μl: the reaction buffer (1× final concentration), 200 μM of each dNTP, 300 nM of forward and reverse primers, 1.25 U of GoTaq polymerase (Ref M3175, Promega, USA).

For the amplification of the variable part of the light chains, nine different primer pairs were used (MKRev2 to 8+MKC5For) and three different pairs for those of the heavy chains (CA5: VHRev1+VHFor, CH10: VHRev1+MpCFor).

TABLE 7

Nucleotide sequences of the primers used for sequencing the heavy (VH) and light (VL) chains of the CA5 antibody
CA5 antibody

| Name | 5'-3' sequence | SEQ ID NO |
|---|---|---|
| Heavy Chain (VH) | | |
| VHRev1 | CGGGATCCTCTAGAGGTCCAACTGCAGGAG TCAGG | SEQ ID NO: 23 |
| VHFor | CAGGGGCCAGTGGATAGAC | SEQ ID NO: 24 |
| Light chain (VL) | | |
| MKRev5 | GACATTGTGATGACCCAGTCT | SEQ ID NO: 25 |
| MKC5For | GGATACAGTTGGTGCAGCATC | SEQ ID NO: 26 |

TABLE 8

Nucleotide sequences of the primers used for sequencing the 5' part of the heavy (VH) and light (VL) chains of the CA5 antibody
CA5 antibody

| Name | 5'-3' sequence | SEQ ID NO |
|---|---|---|
| Heavy chain (VH) | | |
| CA5VH_Fw | CACTTTTACATGGTATCCAGTG | SEQ ID NO: 27 |
| CA5VH_Rev | GTTTCTACTTGCAGCAATCCACT | SEQ ID NO: 28 |
| Light chain (VL) | | |
| CA5VL_Fw | GAVVTCACAGROCCAGGTYC | SEQ ID NO: 29 |
| CA5VL_Rev | CCCAGTAAATCAGCAGTTTAGGA | SEQ ID NO: 30 |

TABLE 9

Nucleotide sequences of the primers used for sequencing the heavy (VH) and light (VL) chains of the CH10 antibody
CH10 antibody

| Name | 5'-3' sequence | SEQ ID NO |
|---|---|---|
| Heavy chain (VH) | | |
| VHRev1 | CGGGATCCTCTAGAGGTCCAACTGC AGGAGTCAGG | SEQ ID NO: 23 |
| MpCFor | GGGGAAGACATTTGGGAAGG | SEQ ID NO: 31 |

TABLE 9-continued

Nucleotide sequences of the primers used for sequencing the heavy (VH) and light (VL) chains of the CH10 antibody
CH10 antibody

| Name | 5'-3' sequence | SEQ ID NO |
|---|---|---|
| Light chain (VL) | | |
| MKRev2 | GATATTGTGATGACGCAGGCT | SEQ ID NO: 32 |
| MKRev3 | GATATTGTGATAACCCAG | SEQ ID NO: 33 |
| MKRev4 | GACATTGTGCTGACCCAATCT | SEQ ID NO: 34 |
| MKRev6 | GATATTGTGCTAACTCAGTCT | SEQ ID NO: 35 |
| MKRev8 | GACATCCAGCTGACTCAGTCT | SEQ ID NO: 36 |
| MKC5For | GGATACAGTTGGTGCAGCATC | SEQ ID NO: 37 |

TABLE 10

Nucleotide sequences of the primers used for sequencing the 5' part of the heavy (VH) and light (VL) chains of the CH10 antibody
CH10 antibody

| Name | 5'-3' sequence | SEQ ID NO |
|---|---|---|
| Heavy chain (VH) | | |
| CH10VH_Fw | ATGGTGTTGGGGCTGAAGTG | SEQ ID NO: 38 |
| CH10VH_Rev | CAGTTCATGGCGTAGGTATTGA | SEQ ID NO: 39 |
| Light chain (VL) | | |
| CH10VL_Fw | TTCTGGAYTTCAGCCTCCAG | SEQ ID NO: 40 |
| CH10VL_Rev | GATTGGGAAGCATATTTGATGAG | SEQ ID NO: 41 |

The PCR program used is composed of an initial denaturation for 2 min at 95° C. followed by 30 cycles of denaturation for 30 sec at 95° C., hybridization for 30 sec at 47° C. and amplification for 1 min at 72° C. and, finally, a final amplification for 5 min at 72° C. The PCR products obtained were desalted with the QIAquick®Gel extraction kit (Ref 28704, Qiagen GmbH, Germany), then ligated with the pGEMT easy vector plasmid (Ref A1360, Promega, USA) so as to be used to transform bacteria. The plasmid DNA extracted from various bacterial clones was sent for sequencing analysis (Macrogen Europe, the Netherlands).

The 5'-terminal nucleotide sequences of the VH and VL of the two antibodies were subsequently determined through the design of specific primers anchored in the leader sequences of the cDNAs (Fw primer). These primers were designed following the identification of homology by alignment between the VL and VH sequences previously obtained and the database of the IMGT/V-QUEST software (Brochet et al., Nucl. Acids Res., 36: W503-508, 2008; Giudicelli et al., Cold Spring Harb Protoc., 2011(6): 695-715, 2011) [3, 4] and extraction of the leader sequences of interest from IMGT/GENE-DB (Giudicelli et al., Nucl. Acids Res., 33: D256-261, 2005) [5]. The reverse (Rev) primers were designed in the previously determined respective VH and VL sequences of each of the antibodies. The protocol used to obtain the 5' part is the same as that described in the previous paragraph.

The consensus nucleotide sequences were deduced from the alignment of the sequences using the MultAlin software (Corpet, Nucl. Acids Res., 16(22): 10881-10890, 1988) [6]. The transcription into polypeptide sequences and the annotation of the CDRs were carried out using the IMGT/V-QUEST software. The results are presented in tables 11 to 14.

TABLE 11

Nucleotide and peptide sequences of the heavy (VH) and light (VL) variable parts of the CA5 antibody
Antibody (CA5)

Heavy chain (VH)

| | |
|---|---|
| Nucleotide sequence SEQ ID NO: 1 | GAGGTGAAGCTGGTGGAATCTGGAGGAGGCTTGGTACAGCCTGG GGGTTCTCTGAGACTCTCCTGTGCAACTTCTGGGTTCACCTTCAG TGATTTCTACATGGAGTGGGTCCGCCAGCCTCCAGGGAAGAGAC TGGAGTGGATTGCTGCAAGTAGAAACAAAGCTAAGGATTATACAA CAGAGTACAGTGCATCTGTGAAGGGTCGGTTCATCGTCTCCAGAG ACACTTCCCAAAGCATCCTCTACCTTCAGATGAATGCCCTGAGAG CTGAGGACACTGCCATTTATTTCTGTGCAAGAGATGCAAGGTTTG CTTACTGGGGCCAAGGGACTCTGGTCACTGTCTCTGCA |
| Peptide sequence SEQ ID NO: 2 | EVKLVESGGGLVQPGGSLRLSCATSGFTFSDFYMEWVRQPPGKRL EWIAASRNKAKDYTTEYSASVKGRFIVSRDTSQSILYLQMNALRAEDT AIYFCARDARFAYWGQGTLVTVSA |

Light chain (VL)

| | |
|---|---|
| Nucleotide sequence SEQ ID NO: 3 | GACATTGTGATGTCACAGTCTCCATCCTCCCTAGCTGTGTCAGTT GGAGAGAAGATTACTATGAGCTGCAAGTCCAGTCAGAGCCTTTTA TATAGTAGCAATCAAAAGAACTACTTGGCCTGGTACCAGCAGAAA CCAGGGCAGTCTCCTAAACTGCTGATTTACTGGGCATCCACTAGG GAATCTGGGGTCCCTGATCGCTTCACAGGCAGTGGATCTGGGAC AGATTTCACTCTCACCATCAGCAGTGTGAAGGCTGAAGACCTGGC AGTTTATTACTGTCAGCAATATTATAGCTATCCTCGGACGTTCGGT GGAGGCACCAAGCTGGAAATCAAA |
| Peptide sequence SEQ ID NO: 4 | DIVMSQSPSSLAVSVGEKITMSCKSSQSLLYSSNQKNYLAWYQQKP GQSPKLLIYWASTRESGVPDRFTGSGSGTDFTLTISSVKAEDLAVYY CQQYYSYPRTFGGGTKLEIK |

TABLE 12

Nucleotide and peptide sequences of the heavy (VH) and light (VL) variable parts of the CH10 antibody
CH10 antibody

Heavy chain (VH)

| | |
|---|---|
| Nucleotide sequence SEQ ID NO: 5 | GAGGTGCAGCTTGTTGAGTCTGGTGGAGGATTGGTGCAGCCTAA AGGGTCATTGAAACTCTCATGTGCAGCCTCTGGATTCACCTTCAA TACCTACGCCATGAACTGGGTCCGCCAGGCTCCAGGAAAGGGTT TGGAATGGGTTGCTCGCATAAGAAGTAAAAGTAATAATTATGCAAC ATATTATGCCGATTCAGTGAAAGACAGGTTCACCATCTCCAGAGA TGATTCACAAAGCATGCTCTATCTGCAAATGAACAACCTGAAAACT GAGGACACAGCCATGTATTACTGTGTGAGACAGGATTACTACGGT AGTAGCTACTTTGACTACTGGGGCCAAGGCACCACTCTCACAGTC TCCTCA |
| Peptide sequence SEQ ID NO: 6 | EVQLVESGGGLVQPKGSLKLSCAASGFTFNTYAMNWVRQAPGKGL EWVARIRSKSNNYATYYADSVKDRFTISRDDSQSMLYLQMNNLKTE DTAMYYCVRQDYYGSSYFDYWGQGTTLTVSS |

Light chain (VL)

| | |
|---|---|
| Nucleotide sequence SEQ ID NO: 7 | GACATTGTGATGACTCAGTCTCCAGCCACCCTGTCTGTGACTCCA GGAGATAGAGTCTCTCTTTCCTGCAGGGCCAGCCAGAGTATTAGC GACTACTTACACTGGTATCAACAAAAATCACATGAGTCTCCAAGG CTTCTCATCAAATATGCTTCCCAATCCATCTCTGGGATCCCCTCCA GGTTCAGTGGCAGTGGATCAGGGTCAGATTTCACTCTCAGTATCA ACAGTGTGGAACCTGAAGATGTTGGAGTGTATTACTGTCAAAATG GTCACAGCTTTCCGTACACGTTCGGAGGGGGGACCAAGCTGGAA ATAAAA |
| Peptide sequence SEQ ID NO: 8 | DIVMTQSPATLSVTPGDRVSLSCRASQSISDYLHWYQQKSHESPRLL IKYASQSISGIPSRFSGSGSGSDFTLSINSVEPEDVGVYYCQNGHSFP YTFGGGTKLEIK |

TABLE 13

CDRs of the heavy (VH) and light (VL) variable parts of the CA5 antibody

| | |
|---|---|
| VH-CDR1 (SEQ ID NO: 9) | GFTFSDFY |
| VH-CDR2 (SEQ ID NO: 10) | SRNKAKDYTT |
| VH-CDR3 (SEQ ID NO: 11) | ARDARFAY |
| VL-CDR1 (SEQ ID NO: 12) | QSLLYSSNQKNY |
| VL-CDR2 | WAS |
| VL-CDR3 (SEQ ID NO: 13) | QQYYSYPRT |

TABLE 14

CDRs of the heavy (VH) and light (VL) variable parts of the CH10 antibody

| | |
|---|---|
| VH-CDR1 (SEQ ID NO: 14) | GFTFNTYA |
| VH-CDR2 (SEQ ID NO: 15) | IRSKSNNYAT |
| VH-CDR3 (SEQ ID NO: 16) | VRQDYYGSSYFDY |
| VL-CDR1 (SEQ ID NO: 17) | QSISDY |
| VL-CDR2 | YAS |
| VL-CDR3 (SEQ ID NO: 18) | QNGHSFPYT |

4/Construction, Production and Characterization of scFvs
a/Construction of the scFv Antibody Fragments The synthetic genes of the single-chain variable fragments (scFvs) derived from the CA5 and CH10 antibodies were synthesized by ATG:Biosynthetics GmbH (Germany).

Each sequence was designed from the fusion of the heavy and light variable parts (SEQ ID NO: 1/SEQ ID NO: 3 for CA5; SEQ ID NO: 5/SEQ ID NO: 7 for CH10) lined by a sequence encoding the peptide $(Gly_4Ser)_3$ ensuring the functionality of the protein, and ending with a sequence encoding the $His_6$ peptide (HIS-tag peptide) that will allow purification of the scFvs. In order to enable their insertion into the expression plasmid, the sequences were flanked by the PstI and SalI restriction enzyme sites. An additional sequence was added between the 3' end of the VL and the SalI site allowing elimination of the $His_6$ peptide if desired. The codons were optimized for expression in *E. coli*. A diagrammatic representation of the construction of the scFvs synthetic genes is given in detail below:

| VH | Linker | VL | |
|---|---|---|---|
| LQ ............ | $(G_4S)_3$ | ................. LE | $IKH_6$ LE IK VD |
| PstI | | .. XhoI | XhoI SalI |

The antibody fragments were inserted between the PstI and XhoI enzymatic sites of the pSW1 expression plasmid (ATG:Biosynthetics GmbH, Germany) according to E. S. Ward et al. (VVard et al., Nature, 341: 544-546, 1989) [7] which contains, under the control of a LacZ inducible promoter, a PelB signal sequence which, fused in reading frame with the gene of the recombinant antibody fragment, allows trafficking of the synthesized protein to the bacterial periplasm. In the periplasm, this signal sequence is eliminated by a peptidase.

After verification, by sequencing, of the quality of the constructs, the pSW1-CA5 and pSW1-CH10 plasmids were used to transform, by heat shock, HB2151 bacteria (T53040, Interchim, France) made competent (Li et al., Afr. J. Biotechnol., 9(50): 8549-8554, 2010) [8].

TABLE 15

Nucleotide and peptide sequences of the CA5 scFv
CA5 scFv

| | |
|---|---|
| Nucleotide sequence SEQ ID NO: 19 | CAGGTGCAGCTGCAGCAGTCAGGCGGCGGCCTGGTACAACCT<br>GGTGGCTCACTGCGCCTGAGCTGCGCAACCAGCGGTTTTACCT<br>TTAGCGATTTCTACATGGAATGGGTTCGCCAACCGCCGGGTAAG<br>CGTCTGGAATGGATCGCGGCGAGCCGTAACAAGGCGAAAGATT<br>ATACCACTGAATATAGCGCGTCGGTGAAAGGTCGCTTCATTGTC<br>TCGCGCGATACCAGCCAGTCGATTCTGTATCTGCAAATGAATGC<br>CCTGCGTGCCGAAGACACGGCCATCTACTTCTGTGCGCGTGAT<br>GCACGCTTTGCCTATTGGGGCCAAGGCACCCTGGTGACCGTTA<br>GCGCCGGTGGTGGCGGTTCAGGTGGTGGCGGTAGCGGTGGCG<br>GTGGCTCAGATATTCAGATGACCCAGACCCCGTCAAGCCTGGC<br>GGTGTCAGTCGGCGAAGAGATTACTATGAGCTGTAAAAGCTCGC<br>AGAGCCTGCTGTACTCATCGAACCAGAAAAATTACCTGGCATGG<br>TATCAACAGAAGCCGGGTCAGTCGCCGAAACTGCTGATCTACTG<br>GGCCTCAACCCGTGAGAGCGGCGTACCGGATCGCTTTACTGGC<br>AGCGGCAGCGGCACGGACTTTACGCTGACGATTAGCTCGGTGA<br>AGGCCGAAGACCTGGCGGTTTATTATTGCCAACAGTACTATAGC<br>TACCCTCGTACCTTCGGCGGCGGCACGAAACTCGAGATTAAACA<br>TCACCATCACCATCACTAACTCGAGATCAAGTAA |
| Peptide sequence SEQ ID NO: 20 | QVQLQQSGGGLVQPGGSLRLSCATSGFTFSDFYMEWVRQPPGKR<br>LEWIAASRNKAKDYTTEYSASVKGRFIVSRDTSQSILYLQMNALRAE<br>DTAIYFCARDARFAYWGQGTLVTVSAGGGGSGGGGSGGGGSDIQ<br>MTQTPSSLAVSVGEEITMSCKSSQSLLYSSNQKNYLAVVYQQKPGQ<br>SPKLLIYWASTRESGVPDRFTGSGSGTDFTLTISSVKAEDLAVYYC<br>QQYYSYPRTFGGGTKLEIKHHHHHH |

TABLE 16

Nucleotide and peptide sequences of the CH10 scFv

CH10 scFv

| | |
|---|---|
| Nucleotide sequence SEQ ID NO: 21 | CAGGTGCAGCTGCAGCAATCAGGCGGCGGCCTGGTCCAACCG AAAGGTAGCCTGAAACTGTCGTGCGCCGCCAGCGGCTTTACGT TCAACACTTACGCGATGAATTGGGTGCGTCAGGCGCCTGGTAAA GGCCTGGAATGGGTGGCACGCATCCGTTCAAAAAGCAACAATTA CGCGACGTATTATGCAGACAGCGTAAAAGATCGCTTTACCATCA GCCGTGATGATTCACAGTCAATGCTGTACCTGCAAATGAATAAC CTGAAAACTGAAGCACTGCGATGTATTATTGTGTTCGCCAGGA CTATTACGGTAGCTCGTATTTCGATTACTGGGGCCAAGGCACCA CCCTGACGGTGAGCTCGGGTGGCGGTGGCTCAGGTGGTGGTG GTAGCGGCGGTGGCGGTAGCGATATCCAGATGACCCAGACCCC GGCAACCCTGAGCGTTACCCCTGGTGACCGCGTTTCGCTGAGC TGCCGTGCCTCGCAGAGCATTTCGGACTATCTGCACTGGTATCA GCAAAAATCACACGAATCACCGCGTCTGCTGATTAAGTACGCCA GCCAATCGATTAGCGGTATTCCGAGCCGCTTTTCGGGCTCGGG TTCGGGCTCGGATTTTACCCTGTCAATTAATAGCGTAGAGCCGG AAGATGTAGGCGTCTACTATTGTCAGAACGGCCATTCATTCCCG TACACGTTTGGCGGCGGCACCAAGCTCGAGATTAAGCATCACC ATCATCACCATTAACTCGAGATCAAGTAA |
| Peptide sequence SEQ ID NO: 22 | QVQLQQSGGGLVQPKGSLKLSCAASGFTFNTYAMNWVRQAPGKG LEWVARIRSKSNNYATYYADSVKDRFTISRDDSQSMLYLQMNNLKT EDTAMYYCVRQDYYGSSYFDYWGQGTTLTVSSGGGGSGGGGSG GGGSDIQMTQTPATLSVTPGDRVSLSCRASQSISDYLHVVYQQKSH ESPRLLIKYASQSISGIPSRFSGSGSGSDFTLSINSVEPEDVGVYYC QNGHSFPYTFGGGTKLEIKHHHHHH | b/Production of the Recombinant Antibody Fragments
Bacterial Culture

A preculture was prepared in 5 ml of 2×YT medium containing 50 μg/ml of ampicillin overnight at 37° C. The following day, 500 μl of this preculture were inoculated into 500 ml of the same medium and grown at 37° C. at 150 RPM until an $OD_{600nm}$ of 1.4 was obtained. The synthesis of the scFv was induced by adding 0.1 mM of IPTG for 16 h at 16° C. at 150 RPM.

Extraction

The culture medium was centrifuged for 30 min at 4500 g at 4° C. The remainder of the preparation was carried out at 4° C. To extract the bacterial periplasm, the pellet was resuspended and incubated in 10 ml of TES (0.2 M Tris, pH 8, 0.5 M EDTA, 0.5 M sucrose) for 30 min to which were then added 15 ml of TES diluted to ¼, followed by further incubation for 30 min. The bacterial extract was centrifuged for 30 min at 10,000 g. The supernatant was dialyzed against PBS overnight. The dialyzed supernatant was immediately treated in order to purify the scFv or stored at −20° C. until use.

The production of the scFv in the periplasm was analyzed by Western blotting using an anti-His-Tag HRP antibody (Ref R93125 Life Technologies, France) according to the manufacturers recommendations for use.

Purification

The periplasm was centrifuged for 20 min at 5,000 g at 4° C. The supernatant was incubated with HIS-Select® Nickel Affinity Gel (Sigma-Aldrich, MO, USA) with stirring for 1 h at 4° C. The gel was washed with a 0.05 M sodium phosphate buffer containing 0.3 M NaCl, pH8, then the same buffer with 20 mM of imidazole added thereto, until an $OD_{280nm}$ close to 0 was obtained. The scFv was then eluted with a 0.05 M sodium phosphate buffer containing 0.3 M NaCl and 250 mM imidazole, pH8. The eluate was dialyzed against PBS overnight. It is stored at −20° C.

Quality Control

The purified scFv was analyzed by electrophoresis on a 15% polyacrylamide gel after staining with Coomassie blue and by exclusion chromatography on a Sephadex™ 75 10/300 GL column (Ref 17-5174-01 GE Healthcare, Germany).

5/Specificity

The specificity of the antibodies and of the scFv thereof was studied by the ELISA technique. Each hormone evaluated was prepared at the concentration of 10 μg/ml in a 0.1M sodium carbonate buffer, pH 9.6, and distributed in a proportion of 100 μl per well on an ELISA plate. The adsorption time was 18 hours at +4° C. After five washes, the wells were treated with 100 μl of PBS supplemented with 0.1% Tween and 1% BSA for 45 minutes at 37° C., then each antibody or scFv was distributed in a proportion of 100 μl/well and incubated for one hour at 37° C. On each hormone evaluated, the antibodies and the scFvs were distributed at various concentrations according to a range of 10 to 250 μg/ml for the antibodies and of 10 to 150 or 200 μg/ml for the scFvs.

After five washes, a secondary antibody coupled to peroxidase (HRP) was distributed in a proportion of 100 μl/well and incubated for one hour at 37° C. Depending on the isotype of the monoclonal antibody studied, the secondary antibody was an anti-IgG1 HRP (Ref. 115-035-205, Jackson ImmunoResearch Laboratories Inc), an anti-IgG2a HRP (Ref. 115-035-206, Jackson Laboratories) or an anti-IgM HRP (Ref. 115-035-075, Jackson Laboratories). For the scFvs, an anti-His Tag HRP (Ref. R93125 Life Technologies, France) was used. After five washes, the enzymatic activity was revealed with TMB distributed in a proportion of 100 μl/well. The revealing time was from 5 to 30 min at ambient temperature depending on the rate of the reaction. After the reaction had been stopped with 1M $H_2SO_4$ (50 μl/well), the strength of the colored reaction (optical density) was measured using a spectrophotometer for ELISA plates.

For the CA5 and CH10 antibodies and the scFvs thereof, the percentage of cross reaction was calculated relative to the values obtained with ovine FSH (oFSH) considered to be the 100% reference value. The percentage of cross reaction was calculated conventionally by comparing the dose-response curves obtained with the concentration range of the antibody or of the scFv. On the basis of the curve obtained with the reference hormone:

let A be the concentration giving 50% of the maximum optical density (ED 50).

On the basis of the curve obtained with another hormone, let B be the concentration corresponding to the same optical density value as that used to define A.

The percentage of cross reaction is equal to A divided by B and multiplied by 100: [(A/B)×100].

Specificity of the CA5 Antibody and of the scFv Thereof

Table 17 illustrates the percentages of cross reaction of the CA5 antibody with the α- and β-subunits (s.u.) of ovine FSH and the β-subunit of human FSH:

TABLE 17

| CA5 | oFSH | α-s.u. oFSH | β-s.u. oFSH | β-s.u. hFSH |
|---|---|---|---|---|
| Cross reaction | 100% | 6% | 80% | 50% |

The CA5 antibody recognizes the ovine α-subunit very little, but strongly recognizes the β-subunit of ovine FSH (80%); it also cross reacts with the β-subunit of human FSH, less strongly (50%). Its specificity is anti-FSH β-subunit.

Table 18 illustrates the percentages of cross reaction of CA5 and of the CA5 scFv with porcine FSH (pFSH) and various human FSHs:

TABLE 18

|  | oFSH | pFSH | hFSH (Gonal F) | hFSH (Puregon) | hFSH (Fostimon) | hMG (Menopur) |
|---|---|---|---|---|---|---|
| CA5 | 100% | 134% | 128% | 70% | 76% | 61% |
| CA5 scFv | 100% | 61% | ND | ND | 10% | 10% |

The CA5 antibody exhibits strong recognition of porcine FSH and of the human FSH Gonal-F. It also cross reacts significantly with the other human FSHs between 61 and 76%. The CA5 antibody recognizes the FSHs tested better in their dimeric form, which tends to indicate specificity against a conformational epitope.

The CA5 scFv significantly recognizes pFSH (61%) and more weakly an hFSH (Fostimon) and hMG (Menopur). The cross reaction on the other two human FSHs could not be measured (ND) because of binding that was too weak. The binding of the CA5 scFv, just like that of the whole antibody, therefore appears to be dependent on the conformation of the hormone, which is probably modified during the adsorption onto the plastic of the ELISA plate.

The specificity of the CA5 scFv was evaluated with respect to porcine LH (pLH), ovine LH (oLH), bovine LH (bLH), eCG and the hCGs Chorulon and Endo 5000. The results are given in table 19:

TABLE 19

|  | oLH | pLH | bLH | eCG | Chorulon | Endo 5000 |
|---|---|---|---|---|---|---|
| CA5 scFv | 25% | 29% | 33% | ND | 10% | ND |

The binding of the CA5 scFv is significant with respect to the animal LHs with a cross reaction between 35% and 40%. Conversely, only the hCG Chorulon is weakly recognized (10%). The binding that was too weak on the other two hCG adsorbed did not make it possible to quantify cross reaction. These results reinforce the hypothesis of a specificity toward a conformational epitope, given the biological effects of CA5 and of the scFv thereof obtained in vitro and in vivo on the hCG activity (see results in examples 2 and 3).

This hypothesis is reinforced by the results obtained by Western blotting by incubating the CA5 antibody on oFSH migrated on a 5% polyacrylamide gel under denaturing or non-denaturing conditions. Only the β-oFSH band was recognized under non-denaturing conditions and gave a significant signal. No signal was observed on the oFSH migrated under denaturing conditions.

An estimation of the dissociation constant Kd of the scFv, with respect to the various FSH, LH and CG studied, was calculated on GraphPad Prism (GraphPad Software Inc., San Diego, Calif., USA, version 5) using the "One site-Specific binding" function in a saturation binding model ("saturation binding experiment model", GraphPad PRISM software). The various values obtained are indicated in tables 20 and 21.

TABLE 20

| CA5 scFv | oFSH | pFSH | hFSH Gonal-F | hFSH Puregon | hFSH Fostimon | hMG Menopur |
|---|---|---|---|---|---|---|
| Kd ($10^{-6}$M) | 0.54 | 1.24 | 1.43 | 2.67 | 2.03 | 2.41 |

TABLE 21

| CA5 scFv | oLH | pLH | bLH | eCG | hCG Chorulon | hCG Endo 5000 |
|---|---|---|---|---|---|---|
| Kd ($10^{-6}$M) | 1.95 | 2.47 | 2.43 | 4.07 | 3.80 | 3.14 |

Comparison of the dissociation constants Kd thus estimated indicates a greater affinity of the CA5 scFv for the ovine and porcine FSHs with a value of 0.54 and 1.24 µM respectively. With the exception of the recombinant human FSH Gonal F (Kd 1.43 µM), the CA5 scFv exhibits a lower affinity for the human FSHs (Kd of 2.03 to 2.67 µM). In comparison with oFSH and pFSH, the CA5 scFv exhibits a medium affinity with respect to ovine LH and porcine LH (Kd of 1.95 and 2.47 µM respectively). The Kds estimated with respect to the hCGs and the eCG (Kd of 3.14 to 4.07 µM) indicate a lower affinity of the CA5 scFv for these hormones.

Specificity of the CH10 Antibody and of the scFv Thereof

Table 22 illustrates the percentages of cross reaction of the CH10 antibody with the α- and β-subunits (s.u.) of ovine FSH and the β-subunit of human FSH:

TABLE 22

| CH10 | oFSH | α-s.u. oFSH | β-s.u. oFSH | β-s.u. hFSH |
|---|---|---|---|---|
| Cross reaction | 100% | 43% | 88% | 40% |

The CH10 antibody preferentially recognizes the β-subunit of ovine FSH (88%) and two times less the β-subunit of human FSH and the ovine α-subunit (40% and 43%). According to these results, the specificity of CH10 is anti-FSH β-subunit, preferentially anti-oFSH β-subunit. It recognizes to a lesser extent, but not insignificantly, the ovine α-subunit unlike the CA5 antibody. All of these results can lead to the hypothesis of an epitope involving mainly β but also α, on the region of linkage of the two subunits for example.

Table 23 illustrates the percentages of cross reaction of CH10 and of the CH10 scFv obtained with porcine FSH (pFSH) and various human FSHs:

TABLE 23

|  | oFSH | pFSH | hFSH (Gonal F) | hFSH (Puregon) | hFSH (Fostimon) | hMG (Menopur) |
|---|---|---|---|---|---|---|
| CH10 | 100% | 24% | 50% | 71% | 100% | 48% |
| CH10 scFv | 100% | 175% | 32% | 67% | 30% | 61% |

The CH10 antibody and the scFv thereof exhibit a strong recognition of the animal FSHs and a cross reaction ranging from 30 to 100% for the human FSHs.

The specificity of the CH10 scFv was evaluated with respect to porcine LH (pLH), ovine LH (oLH), bovine LH (bLH), eCG and the hCGs Chorulon and Endo 5000. The results are given in table 24:

TABLE 24

|  | oLH | pLH | bLH | eCG | Chorulon | Endo 5000 |
|---|---|---|---|---|---|---|
| CH10 scFv | 68% | 63% | 52% | ND | ND | ND |

The binding of the CH10 scFv with respect to the animal LHs is significant with a cross reaction between 52% and 68%. Conversely, the binding that was too weak on the hCG and the eCG adsorbed did not make it possible to quantify a cross reaction. These results reinforce the hypothesis of a specificity toward a conformational epitope, given the biological effects of CH10 and of the scFv thereof obtained in vitro and in vivo on the activity of the hCGs Chorulon and Endo 5000 (see results in examples 2 and 3).

An estimation of the dissociation constant Kd of the CH10 scFv, with respect to the various FSH, LH and CG studied, was calculated on GraphPad Prism (GraphPad Software Inc., San Diego, Calif., USA, version 5) using the "One site-Specific binding" function in a saturation binding model ("saturation binding experiment model", GraphPad PRISM software). The values obtained are indicated in tables 25 and 26.

TABLE 25

| CH10 scFv | oFSH | pFSH | hFSH Gonal-F | hFSH Puregon | hFSH Fostimon | hMG Menopur |
|---|---|---|---|---|---|---|
| Kd ($10^{-6}$M) | 2.85 | 5.22 | 1.82 | 11.5 | 1.59 | 7.36 |

TABLE 26

| CH10 scFv | oLH | pLH | bLH | eCG | hCG Chorulon | hCG Endo 5000 |
|---|---|---|---|---|---|---|
| Kd ($10^{-6}$M) | 1.55 | 2.47 | 1.94 | 1.97 | 1.47 | 2.09 |

The dissociation constants Kd thus estimated indicate an affinity of the CH10 scFv both for the ovine and porcine FSHs (Kd of 7.51 and 5.22 µM) and for the human FSHs Gonal F and Fostimon and the hMG Menopur (Kd of 1.82, 1.59 and 7.36 µM respectively). The Kds estimated with respect to the hCGs and the eCG (Kd of 1.47 to 2.09 µM) indicate good affinity of the CH10 scFv for these hormones compared with the FSHs.

Example 2: In Vitro Measurement of the Potentiating Effect of the Ligands of the Invention on the Bioactivity of Fsh The demonstration of the potentiating effect of the ligands of the invention on the bioactivity of FSH was carried out by comparing the biological response obtained with various cell types or lines stimulated either with FSH alone or with the FSH/monoclonal antibody (MAb) complex.

In each of the cases, comparison of the dose-response curves obtained made it possible to quantify the potentiating effect in vitro of the MAb on the biological activity of the complexed FSH. The statistical analysis of the results was carried out using the Prism software (GraphPad Software Inc., San Diego, Calif., USA, version 5).

1/On Primary Cultures of Bovine Granulosa Cells

The potentiating effect of the CA5 and CH10 MAbs on the bioactivity of ovine FSH (oFSH) was first of all characterized on bovine granulosa cells endogenously expressing the bovine FSH receptor.

Hybridoma supernatants at the final concentration of 0.1 µg/ml of CA5 or CH10 antibody were incubated with a range of ovine or human FSH ranging from 3 ng/ml to 25 ng/ml, for 30 mn at 37° C.

The bovine granulosa cells were taken by ovarian puncture on cow ovaries from follicles having a diameter ranging from 2 to 6 mm, according to the protocol described by Chopineau et al. (Mol. Cell Endocrinol., 92(2): 229-39, 1993) [8] and Wehbi et al. (Endocrinology, 151(6): 2788-2799, 2010) [9]. The bovine granulosa cells in suspension in a McCoy's 5A medium (Lonza, Belgium, reference BE12-688F), prepared at 80,000 cells per 0.5 ml, were stimulated for 3 hours at 37° C., with stirring, in the presence of 48 µg/ml of IBMX (Sigma Aldrich, France, reference I5879), with a range of FSH of from 3 ng/ml to 25 ng/ml, alone or pre-complexed with a monoclonal antibody according to the protocol above. The biological response measured was cAMP secretion.

After centrifugation, the cAMP produced was assayed in the culture supernatant using an ELISA kit (Biomedical Technologies Inc., MA, USA, BT-730).

The results are presented in FIG. 1.

The results show an amplification of cAMP secretion by a factor of 1.3 times for CA5 and by a factor of 5.5 times for CH10 on the activity of ovine FSH. The statistical analysis by two-way analysis of variance (two-way ANOVA, GraphPad PRISM software) shows a significant effect ranging from $p<0.05$ (*) for CA5 to $p<0.01$ () and $p<0.001$ (*) for CH10.

2/On HEK 293 Cell Line Stably Transfected with the Human FSH Receptor

The potentiating effect of the MAbs on the FSH of various species was measured on HEK 293 cells stably expressing the human FSH receptor. This system made it possible to measure the cAMP production following activation of the FSH receptor after a stimulation with FSH alone or with the FSH/MAb complex for one hour at 37° C.

For this, 60,000 cells were distributed into wells of 96-well plates (Becton Dickinson, NJ, USA, reference 353072) and cultured for 24 h at 37° C., 5% $CO_2$ in a humid atmosphere, in 100 µl of MEM medium (Ozyme, France, reference BE12-611F) containing 10% FCS (Lonza, Belgium, reference DE14-801F), 1% penicillin/streptomycin (Sigma Aldrich, France, reference P-4333) and 400 pg/ml of G418 (Sigma Aldrich, France, reference A1720). After 2 h of weaning in MEM medium, the cells were stimulated for 1 h at 37° C. The culture supernatant was recovered and assayed using an ELISA kit (Biomedical Technologies Inc., MA, USA, BT-730). The results express the amount of cAMP secreted at the end point. They were analyzed using the Prism software (GraphPad Software Inc., San Diego, Calif., USA, version 5).

Figure 2:
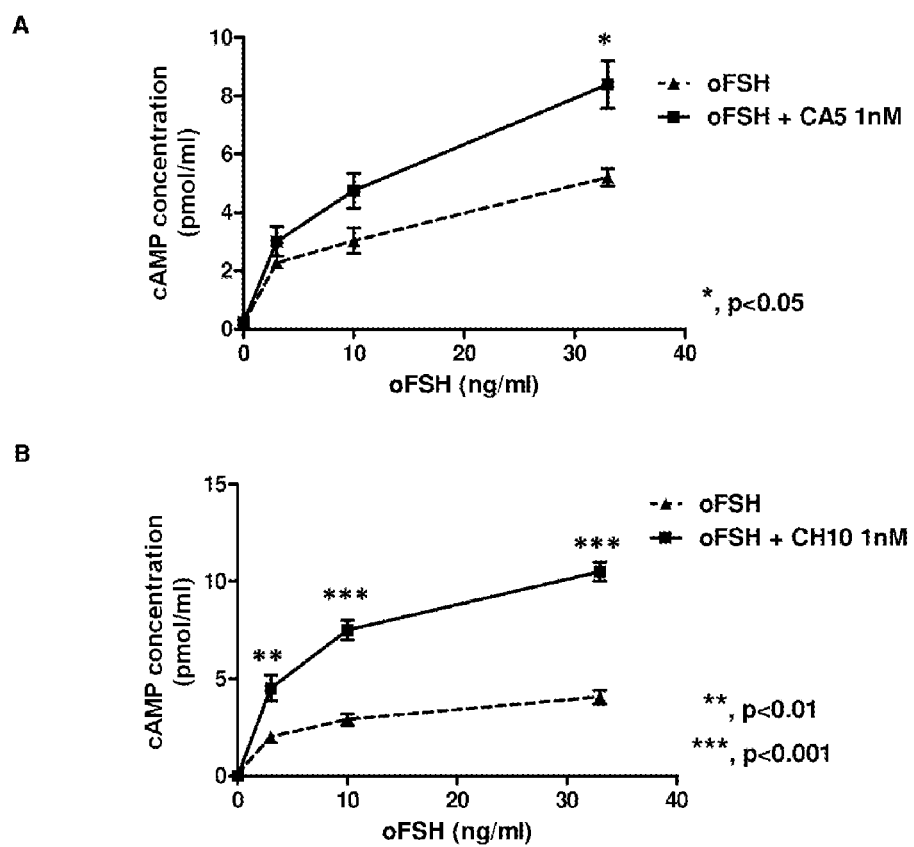
FIG. 2 represents the in vitro potentiating effect of the CA5 (A) and CH10 (B) monoclonal antibodies on the bioactivity of ovine FSH (oFSH) on an HEK 293 cell line stably transfected with the human FSH receptor.

FIG. 2 represents the potentiating effect of the CA5 and CH10 monoclonal antibodies on the bioactivity of ovine FSH (oFSH) in vitro on HEK 293 cells stably transfected with the human FSH receptor. For this, the cells were stimulated either with a range of from 3 ng/ml to 32.5 ng/ml of ovine FSH, or with the same FSH range points previously incubated, for 30 minutes at 37° C., with the monoclonal antibody (final concentration 0.1 µg/ml) before the stimulation of the cells. A two-way analysis of variance (two-way ANOVA, GraphPad PRISM software) made it possible to compare the dose-response curves obtained with the FSH alone or with the FSH/monoclonal antibody complex. The CA5 antibody showed a potentiating effect ranging from 160% to 200% on the activity of oFSH; this effect is significant for the 32.5 ng/ml concentration of oFSH ($p<0.05$). The CH10 antibody exerts a greater potentiating effect on oFSH for all of the concentrations tested ranging from 225% for the 3 ng/ml point ($p<0.01$) to 260% for the 10 ng/ml and 33 ng/ml points respectively ($p<0.001$).

3/On HEK 293 Cell Line Stably Transfected with the Human FSH Receptor and with the Glosensor® System The potentiating effect of the MAbs on the FSHs of various species was measured in real time on HEK 293 cells stably expressing the human FSH receptor and the GloSensor™ vector (Promega, France). This cell system made it possible to monitor the cAMP production following stimulation of the FSH receptor with the agonist (FSH alone or FSH/monoclonal antibody complex) in real time. Following the binding of the cAMP on the GloSensor™ protein, the GloSensor™ substrate (Promega, France, reference E1291) was hydrolyzed and resulted in an emission of luminescence measured by means of a PolarStar Optima reader (BMG Labtech, Germany) and expressed in RLU (Relative Luminescence Units). This stable line was developed by the Biology and BioInformatics of Signaling Systems team at the INRA [French National Institute for Agricultural Research] center, Val de Loire, 37380 Nouzilly, France) and was kindly made available for these assays.

For this, the HEK 293 cells were cultured in a proportion of 80,000 cells per well of a transparent-bottom, white 96-well microplate (Dominique Dutscher, France, reference 655903) and cultured in 100 µl of MEM medium (Ozyme, France, reference BE12-611F) supplemented with 10% FCS (Lonza, Belgium, reference DE14-801F), 1% penicillin/streptomycin (Sigma Aldrich, France, reference P-4333), 200 µg/ml of hygromycin B (Life Technologies™, France, reference 10687010) and 400 µg/ml of G418 (Sigma Aldrich, France, reference A1720) overnight. After 2 h of weaning in 100 µl of MEM medium supplemented with 1% BSA (PAA, France, reference K45012) and containing 4% of GloSensor™ substrate for 2 h at ambient temperature in the dark, the plate of cells was placed in the PolarStar Optima reader and a first reading was carried out for 5 minutes in order to measure the basal level of luminescence. The plate was then removed from the reader and 11 µl of ligand (FSH alone or FSH/monoclonal antibody complex) were added thereto so as to obtain the concentrations indicated. The luminescence emitted was then measured for approximately 1 h 30.

The results obtained were analyzed using the Prism software (GraphPad Prism Software Inc., San Diego, Calif., USA, version 5). The non-linear function "log (agonist) versus response" was used to plot the response as a function of the FSH concentration. This made it possible to characterize and compare the EC50 for the FSH alone and the FSH complexed with the monoclonal antibody. For each example, the significant effect of the FSH/potentiating antibody complex was measured by two-way analysis of variance (two-way ANOVA, GraphPad PRISM software) by comparing the two curves in their entirety.

CA5 Monoclonal Antibody

Figure 3:
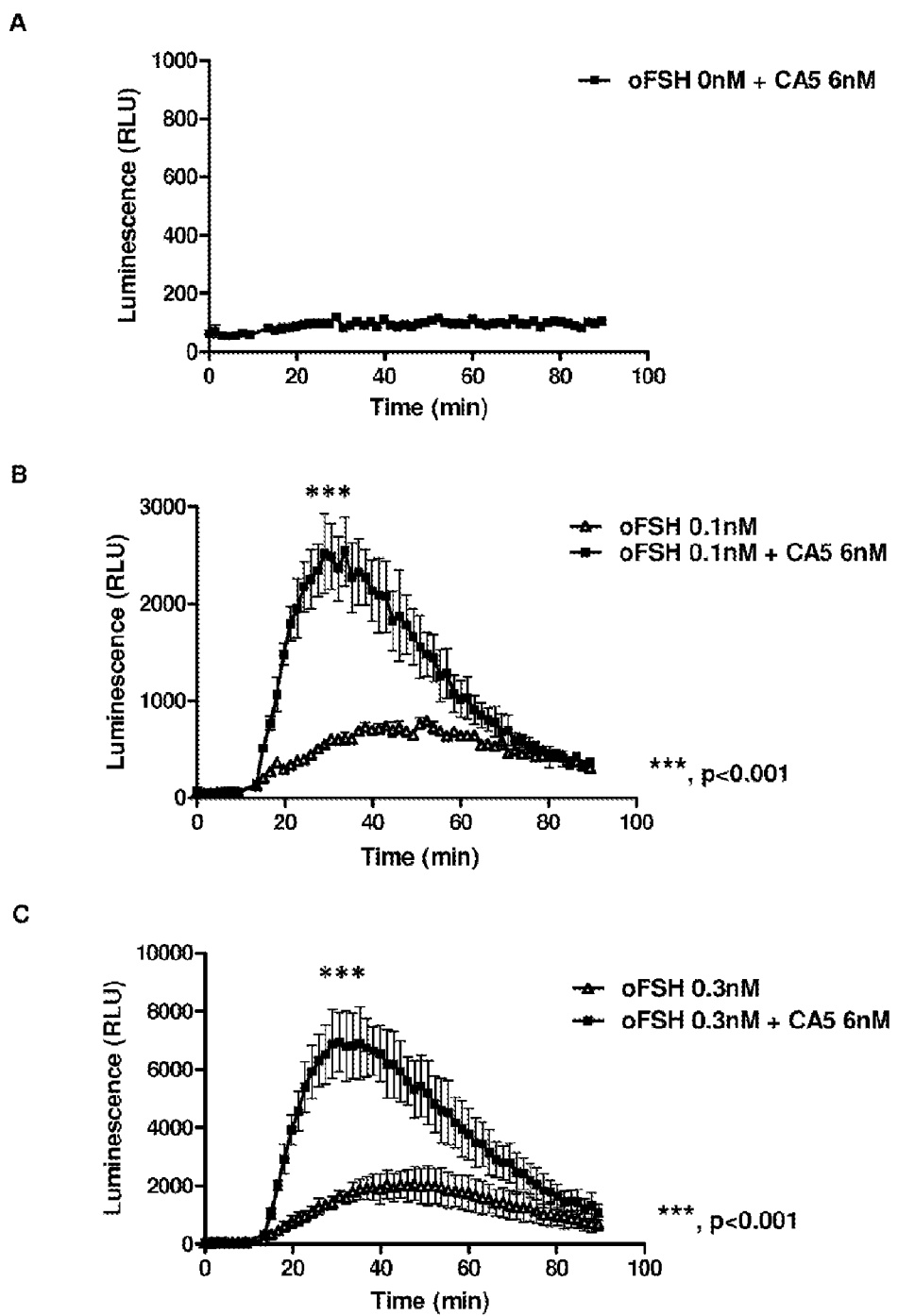
FIG. 3 represents the in vitro potentiating effect of the CA5 monoclonal antibody on the bioactivity of ovine FSH (oFSH) on an HEK 293 cell line stably transfected with the human FSH receptor and the Glosensor® vector.

FIG. 3 illustrates the cAMP production kinetics curves expressed in relative luminescence units as a function of time (in minutes) obtained at the concentrations 0-0.1-0.3-1 and 3 nM of ovine FSH alone or complexed with the CA5 antibody. It is observed that the cells "stimulated" by the antibody alone, without FSH, show no response: the luminescent signal remains at its basal level (curve 3A). The CA5 antibody alone exerts no agonist or antagonist effect on the human FSH receptor expressed by the HEK 293 cells. Conversely, the CA5 monoclonal antibody (final concentration 6 nM), complexed with oFSH very significantly and notably amplifies the stimulating activity of the hormone. An increase in the maximum cell response of 350% and 330% at the concentrations of 0.1 and 0.3 nM of oFSH (curves B and C) and an increase of 230% and 140% respectively for the concentrations of 1 and 3 nM of oFSH (curves D and E) are thus observed. The amplitude of the potentiating effect becomes less with the higher concentrations of oFSH (1 and 3 nM) because of a saturation of the cell response and of the luminescent signal at 11000 RLU in this case. The EC50 value measured by GraphPad Prism is $2.36 \times 10^{-9}$M for oFSH and $2.83 \times 10^{-10}$M for the oFSH/CA5 complex, reflecting an increase of one unit of LogEC50 (from $10^{-8.6}$ to $10^{-9.54}$) when the FSH is complexed with the CA5 antibody. The difference between the two curves of oFSH compared with oFSH/CA5 is highly significant for all of the oFSH doses tested ($p<0.001$).

Figure 4:
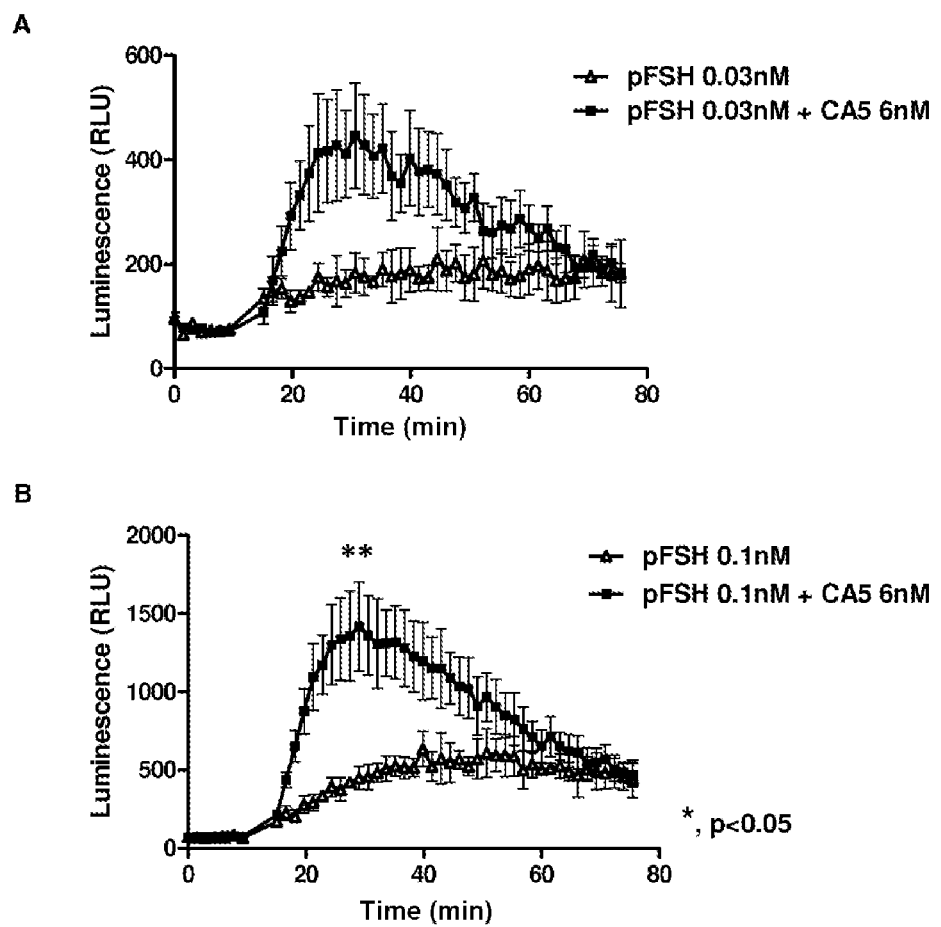
FIG. 4 represents the potentiating effect of the CA5 monoclonal antibody on the bioactivity of porcine FSH (pFSH) on an HEK 293 cell line stably transfected with the human FSH receptor and the Glosensor® vector.

The potentiating effect of the CA5 antibody measured on porcine FSH is illustrated by FIG. 4. An increase of 190% of the maximum response at 0.03 nM of pFSH is observed when said pFSH is complexed with the CA5 antibody (final concentration 6 nM) (curve A), but this increase is not significant. The potentiating effect reaches 250% at the 0.1 nM concentration of pFSH (curve B) and is significant ($p<0.01$). The level of response obtained with 0.03 nM pFSH complexed with CA5 is equivalent to that obtained with 0.1 nM pFSH alone (500 RLU compared with 585 RLU respectively), which means that the 0.03 nM pFSH/CA5 complex induces the same amplitude of response as the pFSH alone at a concentration 3.3 times higher (0.1 nM; i.e. 0.5 Log).

Figure 5:
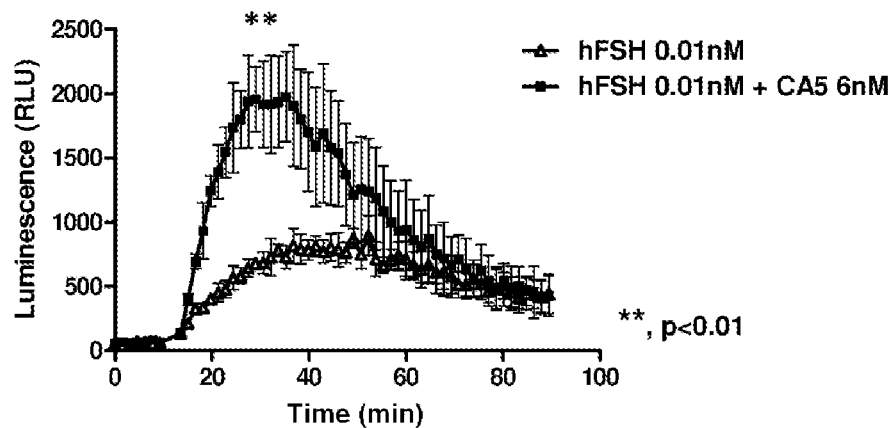
FIG. 5 represents the in vitro potentiating effect of the CA5 monoclonal antibody (A to E) and of the CA5 scFv (F) on the bioactivity of human FSH (hFSH) on an HEK 293 cell line stably transfected with the human FSH receptor and the Glosensor® vector.
Figure 5:
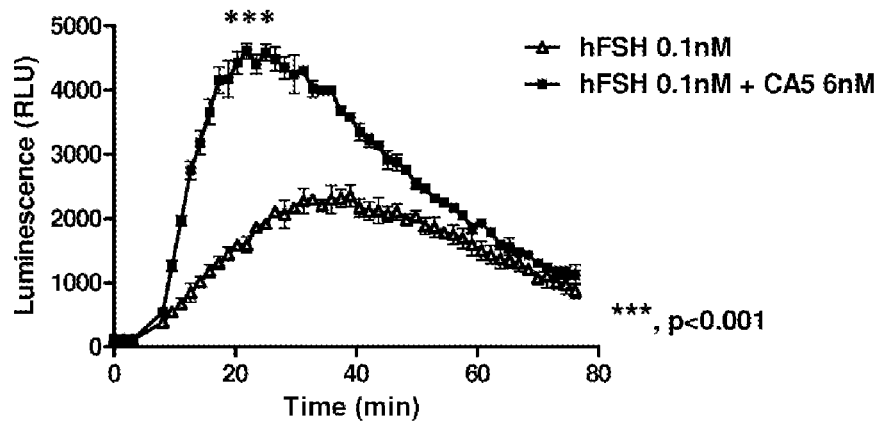
Figure 5:
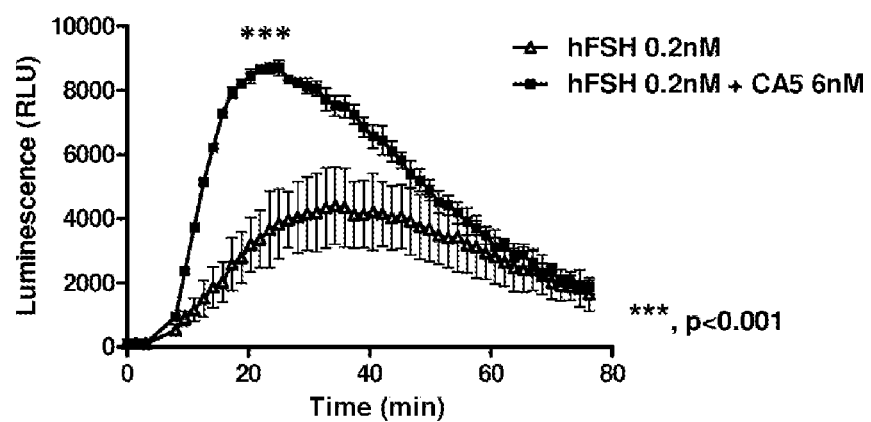

Finally, the potentiating effect of CA5 was studied on the activity of recombinant human FSH (Gonal-F, Serono laboratory). FIG. 5 illustrates the cAMP production kinetics curves expressed in relative luminescence units as a function of time (minutes) obtained during a stimulation with the concentrations 0.03-0.1-0.2-0.3 nM of FSH alone or complexed with the CA5 antibody (6 nM). A potentiating effect of 235% was observed with the 0.03 nM hFSH concentration, of 200% was observed with 0.1 and 0.2 nM of hFSH, then of 170% was observed with the highest hFSH concentration of 0.3 nM because of a saturation of the cell system (maximum 10530 RLU). The EC50 calculation by GraphPad Prism indicated a value of $5.86 \times 10^{-10}$M for hFSH and of $1.36 \times 10^{-10}$M for the hFSH/CA5 complex, reflecting an increase of 0.63 in LogEC50 (from $10^{-9.23}$ to $10^{-9.86}$) when the FSH is complexed with the CA5 antibody. The potentiating effect of the CA5 scFv was also studied on the bioactivity of hFSH at 0.01 nM. A significant increase of 160% ($p<0.01$) was obtained at the scFv concentration of 36 nM (FIG. 5). This increase was similar to that of the divalent whole CA5 antibody. This result means that the monovalent fragment has the same FSH-activity-potentiating properties as the CA5 antibody.

Although significant (p<001), the potentiating effect of the CA5 antibody on the bioactivity of human FSH remains smaller than on the bioactivity of ovine FSH for which an increase of one Log unit was obtained between the EC50 of oFSH and that of the oFSH/CA5 complex.

CH10 Monoclonal Antibody

The modulatory effect of the CH10 antibody was studied on ovine FSH (oFSH) and on human FSH (hFSH) (Gonal F, Serono laboratory).

Figure 6:
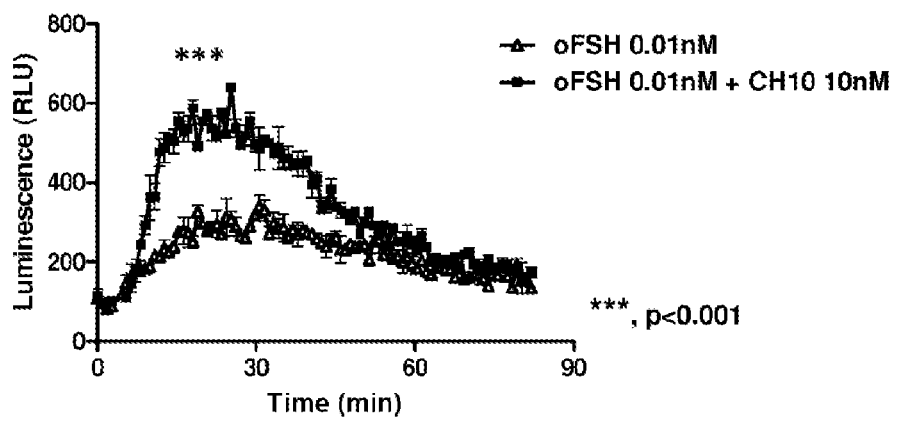
FIG. 6 represents the in vitro potentiating effect of the CH10 monoclonal antibody on the bioactivity of ovine FSH (oFSH) on an HEK 293 cell line stably transfected with the human FSH receptor and the Glosensor® vector.
Figure 6:
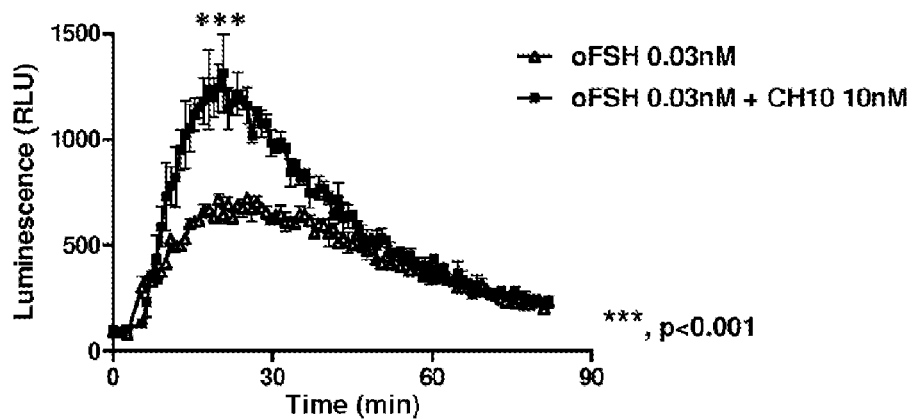
Figure 6:
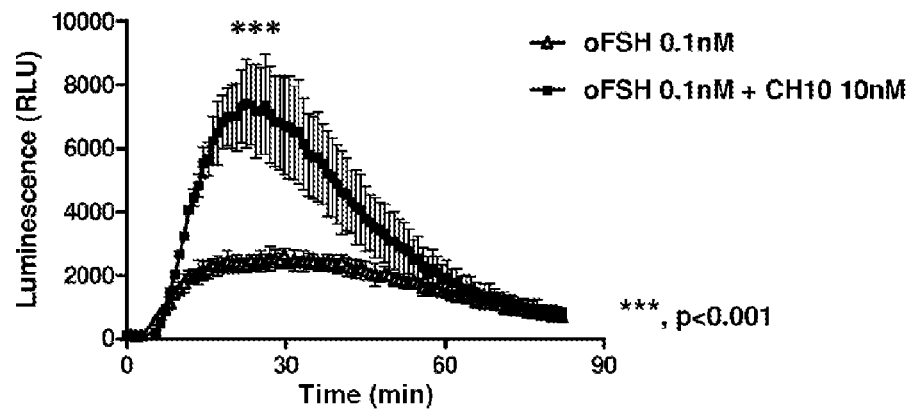

FIG. 6 illustrates the amplifying effect of the CH10 antibody (10 nM) on the bioactivity of oFSH prepared at the concentrations of 0.01-0.03 and 0.1 nM. On the low concentrations (0.01 and 0.03 nM) an increase of 185% of the cell response is obtained with the oFSH/CH10 complex (curves A and B). At the oFSH concentration of 0.1 nM, the increase is 312% with the oFSH/CH10 complex (curve C). These increases are very significant (p<0.001).

Figure 7:
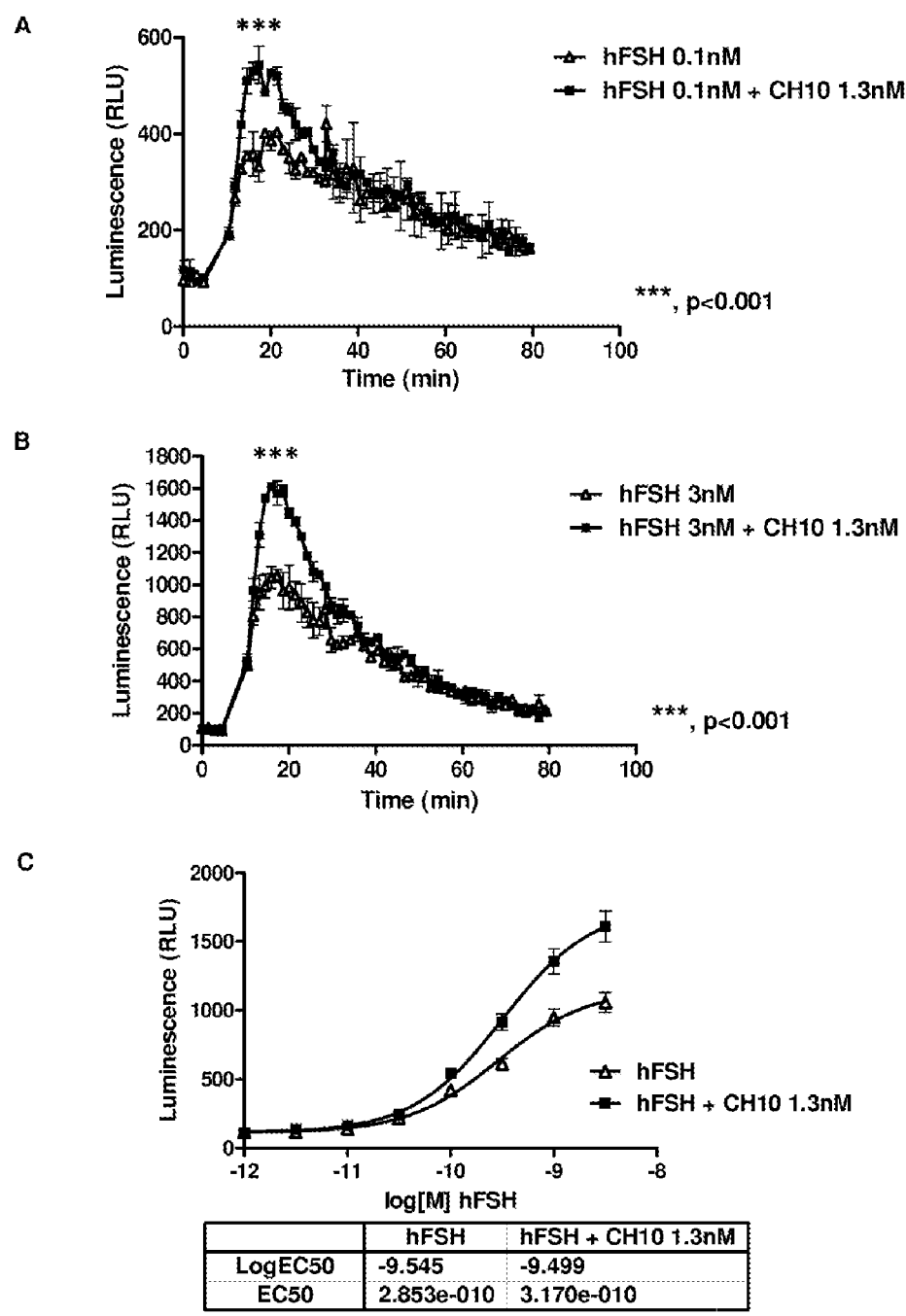
FIG. 7 represents the potentiating effect of the CH10 monoclonal antibody on the bioactivity of human FSH (hFSH) in vitro on an HEK 293 cell line stably transfected with the human FSH receptor and the Glosensor® vector.

The potentiating effect of CH10 (1.3 nM) was measured on human FSH prepared at from 0.1 nM to 3 nM (FIGS. 7A and B). A moderate but significant (p<0.001) increase ranging from 140% to 150% was observed. The EC50 values measured by GraphPad Prism were $2.85 \times 10^{-10}$M for hFSH and $3.17 \times 10^{-10}$M for the hFSH/CH10 complex (FIG. 7C).

The potentiating effect of CH10 is exerted more specifically on ovine animal FSH. A weak effect of the CH10 antibody was observed on human FSH.

Example 3: In Vivo Measurement of the Potentiating Effect of the Ligands of the Invention on the Bioactivity of FSH and LH/CG in the Rat Model After having been characterized in vitro, the potentiating effect of each monoclonal antibody was characterized in vivo, in the female rat for their effect on the bioactivity of FSH and in the male rat for their effect on the bioactivity of LH/CG, that they also recognize.

In order to measure the FSH bioactivity, the protocol used was that of the biological assay described by Steelman and Pohley (Steelman SL, Pohley FM. Endocrinology, 53: 604-616. 1953) [12]. In order to measure the LH bioactivity, the protocol used was that of the assay described by Scobey et al. (Scobey et al., Reprod. Biol. Endocr. 3: 61, 2005) [13].

The effect of the antibodies on the FSH activity was evaluated using ovine and human FSHs. The effect of the antibodies on the LH activity was evaluated on two preparations of hCG (human chorionic gonadotropin).

The statistical analysis was carried out with the GraphPad Prism software (GraphPad Software Inc., San Diego, Calif., USA, version 5). Since the results related to experiments carried out on batches of five animals, a non-parametric, one-way analysis of variance (Kruskal Wallis test), followed by Dunn's correction, was applied or a non-parametric t-test (Mann-Whitney test). For the results relating to larger numbers (n>30) resulting from the compilation of several bioassays, a parametric test (unpaired Student's t test) followed by a Bonferroni correction was applied.

1/Potentiating Effect of the Antibodies on the Bioactivity of FSH in the Female Rat The potentiating effect of the CA5 and CH10 antibodies and of the scFv thereof was studied on ovine FSH and on various preparations of human FSH used in human reproduction, Gonal-F and Puregon (recombinant FSHs from the Merck Serono and Merck Schering-Plough laboratories respectively), and Fostimon and Menopur (extracted FSHs sold by the laboratories Genevrier and Merck Schering-Plough respectively).

As described in the protocol of Steelman and Pohley, 21-day-old immature female rats received, for three consecutive days, two injections, in the morning and the evening, of 100 µl of a mixture of hCG and FSH comprising a constant amount of hCG (3.5 IU) supplemented with a variable amount of FSH ranging from 0.5 to 1.5 IU for the human FSH (Gonal F, Puregon, Fostimon, Menopur) or from 0.5 to 2 µg for the ovine FSH (extracted hormone). Injections were carried out subcutaneously into the nape of the neck. Each experiment comprised a minimum of four batches: one batch treated with physiological saline (serum φ), one batch treated with the antibody or the scFv alone, one batch treated with the hCG+FSH mixture, and one batch treated with the hCG/FSH mixture supplemented with 2 µg of purified scFv antibody.

In the case of a treatment with the hormone/antibody or scFv complex, before the injection, the FSH+antibody mixture was preincubated for 20 minutes at 37° C. or at ambient temperature, without distinction, and then added to the hCG. The hCG can without distinction be mixed with the FSH during the incubation of the complex.

On the fourth day, the female rats were weighed, and their ovaries were taken, dissected and then weighed. The results are expressed in milligram of ovary/100 grams of body weight. The increase in the weight of the ovaries is proportional to the amount of bioactive FSH injected. This makes it possible to quantify and compare the bioactivity of the same amount of hormone injected alone or as a complex with an antibody.

Comparison of the bioactivity of the FSH injected alone or complexed with the antibody or with the scFv makes it possible to measure the differential of the response and to thus quantify the potentiating effect of the antibody or of the scFv thereof.

Effect of the CA5 Antibody and of the scFv Thereof

Figure 8:
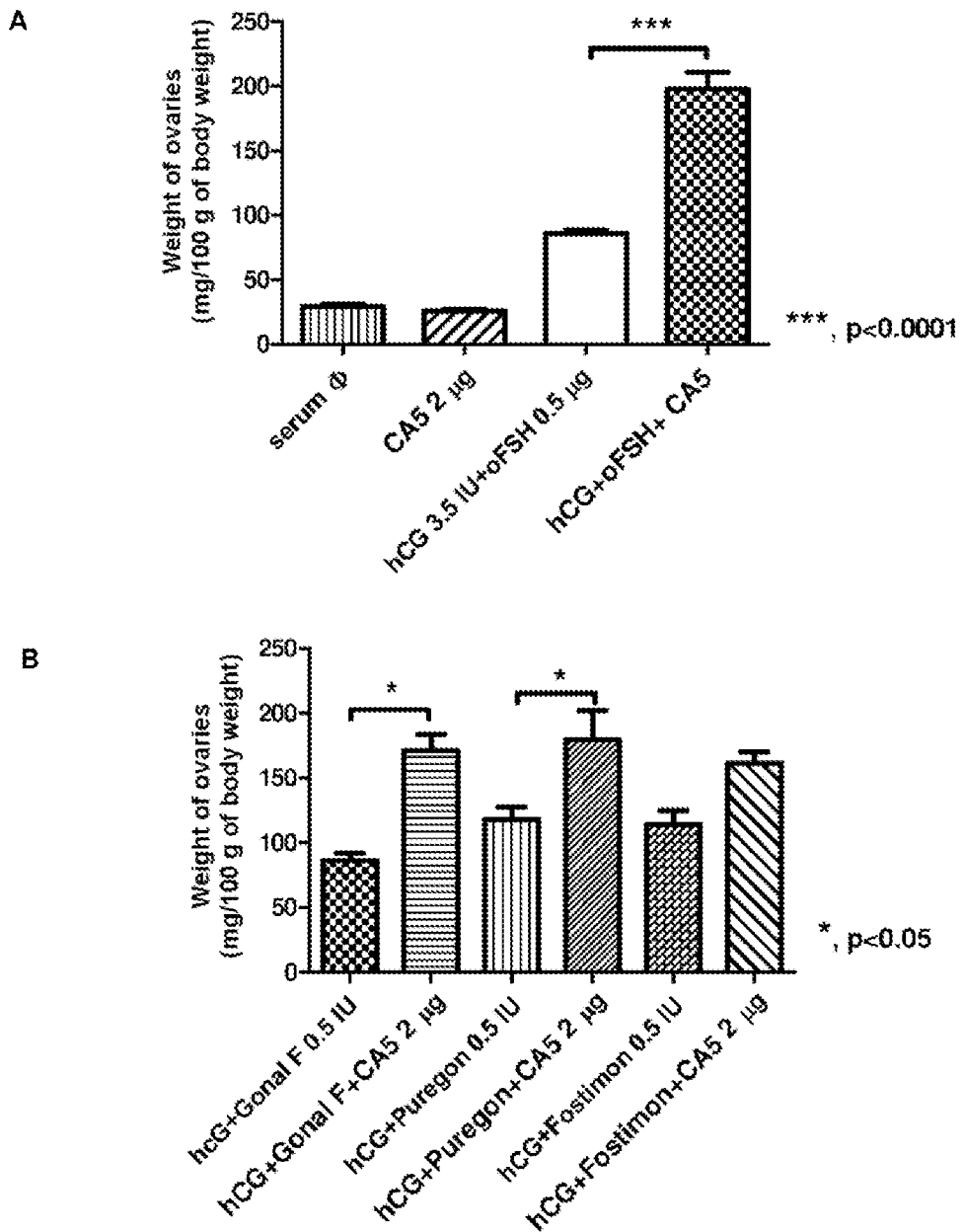
FIG. 8 represents the in vivo potentiating effect of the CA5 monoclonal antibody on the bioactivity of ovine FSH (oFSH) (A) and on the bioactivity of the human FSHs (hFSH) Gonal-F®, Puregon® and Fostimon® (B) in the female rat.

FIG. 8A illustrates a representative example of the effect of the CA5 antibody on the ovine FSH bioactivity. Each batch comprised five females. The batch treated with the CA5 antibody injected alone exhibited the same mean weight of the ovaries as the females of the control batch having received physiological saline (25.6 mg and 29.15 mg respectively). The batch having received the conventional hormonal treatment (3.5 IU hCG+0.5 µg oFSH) gave a mean weight of the ovaries of 85.7 mg significantly higher than the control batch (p<0.05). The batch treated with the ovine FSH precomplexed with the CA5 antibody exhibited a mean weight of 198 mg, i.e. a very significant increase in the FSH bioactivity of 231% compared with the batch having received the conventional hormonal treatment (p<0.0001). The potentiating effect of CA5 on the activity of ovine FSH, in vivo, was analyzed on several experiments, all of the results of which are presented in table 27. The increase in the mean weight of the ovaries, recorded on three experiments, following a stimulation with the hormone/CA5 complex, is highly significant (p<0.0001).

TABLE 27

| batch | Mean ± sem | numbers | statistics |
|---|---|---|---|
| Serum Φ | 25.6 ± 2.4 | 13 | NS |
| CA5 | 29.15 ± 4.6 | 15 | |
| hCG + oFSH | 98.12 ± 6.37 | 13 | *** |
| hCG + oFSH + CA5 | 165.8 ± 11.54 | 12 | p < 0.0001 |

The effect of CA5 on the human FSHs was also analyzed on large numbers over the course of several experiments. The results are presented in table 28 below.

TABLE 28

| batch | Mean ± sem | numbers | statistics |
|---|---|---|---|
| hCG + hFSH | 73.93 ± 1.525 | 77 | *** |
| hCG + hFSH + CA5 | 128.3 ± 4.323 | 80 | $p < 0.0001$ |

The increase in the mean ovary weight recorded in the females treated with the hFSH Gonal F/CA5 complex is 173%: the mean weight of the ovaries goes from 73.93 mg in the females having received a conventional treatment to 128.3 mg in the females having been treated with the hormone/CA5 complex. This difference is highly significant ($p<0.0001$, unpaired t-test).

Finally, the potentiating effect was studied on two other preparations of human FSH (Puregon and Fostimon). The results shown in FIG. 8B are a representative example. A significant increase of 153% was recorded on the activity of the human FSH Puregon ($p<0.05$) and of 142% on the activity of the human FSH Fostimon (NS). In comparison, the increase recorded on the activity of the human FSH Gonal F was 179% in this experiment ($p<0.05$).

In conclusion, the CA5 antibody exerts a major potentiating effect on ovine FSH and a potentiating effect that is also considerable on the activity of human FSH, originating from various pharmaceutical preparations.

Figure 9:
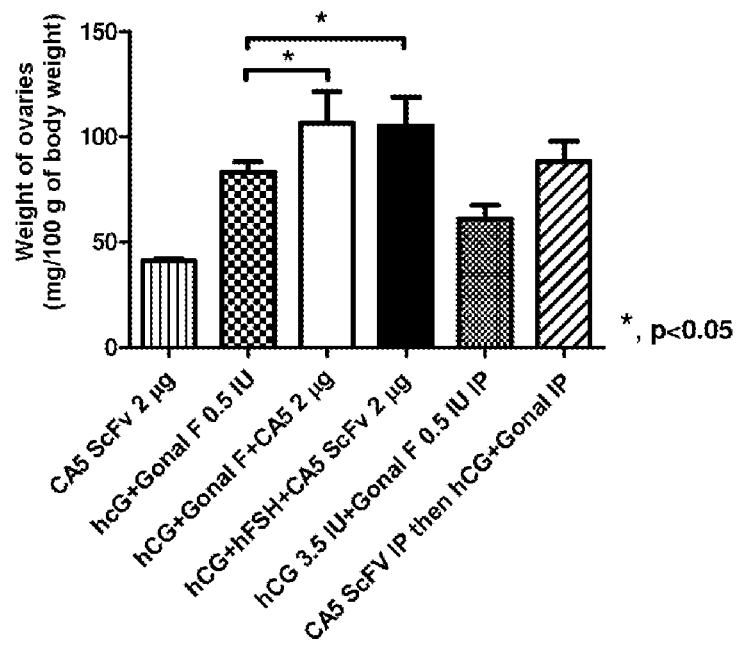
FIG. 9 represents the in vivo potentiating effect of the CA5 monoclonal antibody on the bioactivity of the human FSH (hFSH) Gonal-F® (A) and the potentiating effect of CA5 scFv on the bioactivity of the human FSHs (hFSH) Gonal-F® (A), Puregon® and Fostimon® (B) in the female rat.
Figure 9:
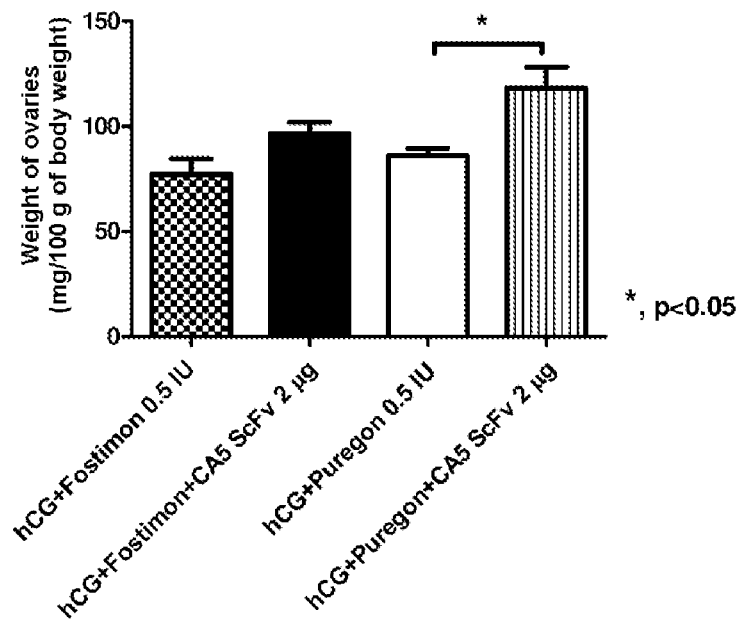

The effect of the CA5 scFv was studied in the same protocol as the whole antibody. FIG. 9A shows the results obtained. The same potentiating effect on the activity of the human FSH Gonal F was obtained with the whole antibody or with the scFv thereof, said effect being significant ($p<0.05$).

Various methods of injection of the hormone/scFv mixtures were evaluated and compared with the conventional protocol (subcutaneous injection). Thus, a bioassay for the purpose of comparing an intraperitoneal injection of the hormonal mixture with an intraperitoneal injection of the hormonal mixture followed by a second, delayed, injection of the CA5 scFv 15 minutes later (FIG. 9A was carried out. In this case, an increase of 146% was obtained in the females treated with the hormone/scFv complex with a mean weight of the ovaries going from 61 mg (batch hCG+hFSH Gonal F) to 89 mg (batch scFv then hCG+hFSH Gonal F). These results are significant since they demonstrate that the potentiating effect of the CA5 scFv can be set up in vivo even if the scFv is injected alone, independently of the hormone and at a later time. The hormone/scFv complex can become formed in vivo in the animal treated.

The potentiating effect of the CA5 scFv was also studied on the activity of the human FSHs Fostimon and Puregon (FIG. 9B). A significant increase of 140% was obtained on the activity of the FSH Puregon ($p<0.05$) and a non-significant increase of 126% was obtained on the activity of the FSH Fostimon (NS).

Effect of the CH10 Antibody and of the scFv Thereof

Figure 10:
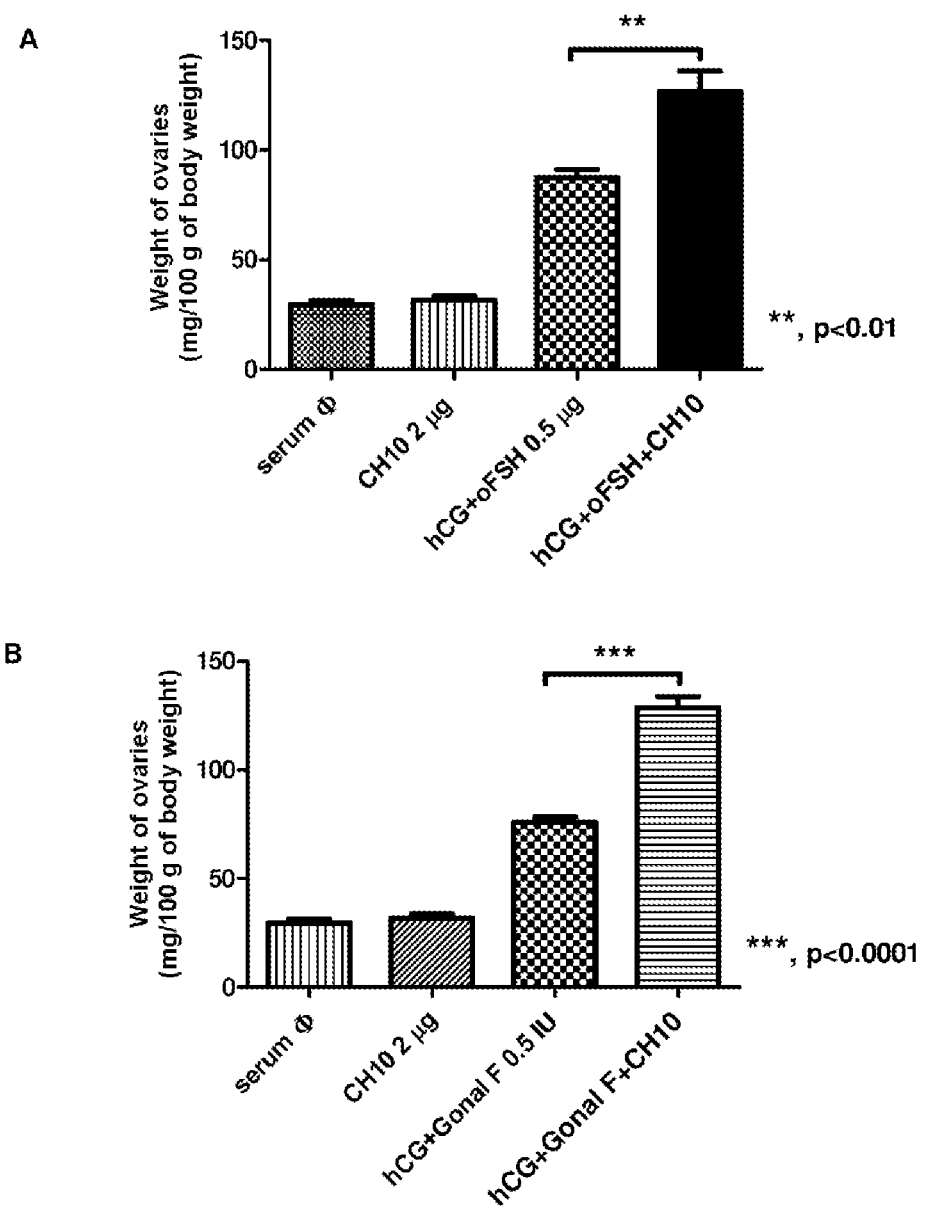
FIG. 10 represents the in vivo potentiating effect of the CH10 monoclonal antibody on the bioactivity of ovine FSH (oFSH) (A) and on the bioactivity of the human FSH (hFSH) Gonal-F® (B) in the female rat.

The potentiating effect of CH10 on the activity of ovine FSH, in vivo, was analyzed during several experiments, all of the results of which are presented in FIG. 10A. Comparison on three experiments of the response between the female rats treated with the hCG+oFSH mixture and those treated with the hormone/CH10 complex demonstrates a significant increase of 145% ($p<0.01$). The mean weight of the ovaries recorded was 87.55±3.724 mg in the females treated with the hCG+oFSH mixture (n=12) to 126.6±9.6 mg/100 g of body weight in the female rats treated with the hormone/CH10 complex (n=13). No effect of the CH10 antibody alone was observed on the ovarian response.

The potentiating effect of CH10 on the human FSH Gonal-F was also analyzed on large numbers over the course of several experiments. The results are presented in table 29 below and in FIG. 10B.

TABLE 29

| batch | Mean ± sem | numbers | statistics |
|---|---|---|---|
| hCG + hFSH GONAL F | 73.93 ± 1.525 | 77 | *** |
| hCG + hFSH Gonal F + CA5 | 128.3 ± 4.323 | 80 | $p < 0.0001$ |

An increase of 170% in the mean weight of the ovaries was recorded in the females treated with the Gonal F/CH10 complex. This difference is highly significant ($p<0.0001$, unpaired t-test).

Figure 11:
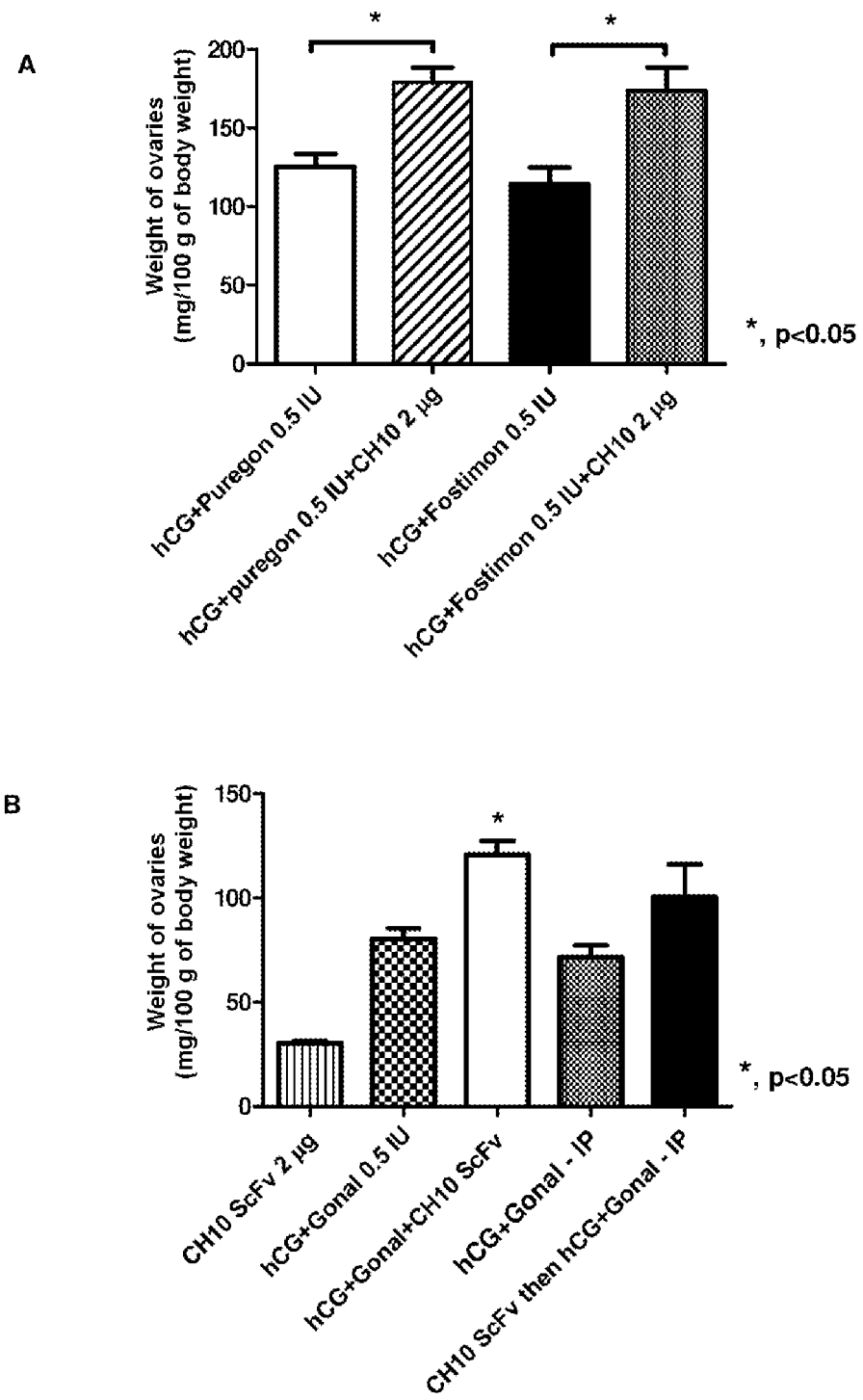
FIG. 11 represents the in vivo potentiating effect of the CH10 monoclonal antibody on the bioactivity of the human FSHs (hFSH) Puregon® and Fostimon® (A) and the potentiating effect of CH10 scFv on the bioactivity of the human FSH (hFSH) Gonal-F® (B) in the female rat.

The potentiating effect of CH10 was also investigated on the human FSHs Puregon and Fostimon (FIG. 11A). A significant increase of 145% and 174% was obtained respectively ($p<0.05$). FIG. 11B shows the effect of the hFSH Gonal F/CH10 scFv complex by conventional subcutaneous injection and by time-delayed intraperitoneal injection. A significant increase of 160% ($p<0.05$) was obtained by conventional injection and an increase of 150%, although not significant, was obtained by independent intraperitoneal injections of the CH10 scFv and of the hFSH. The potentiating effect of the CH10 scFv can thus become set up in vivo, whether it is injected separately or preincubated with the hormone.

Potentiating Effect of the Antibodies on the Bioactivity of LH/CG in the Rat

Because of the very high cost of ovine LH, these biological assays were carried out with hCG, which is readily available, in a very pure and inexpensive form. The effect of the antibodies was studied on two preparations of extracted human hCG (human chorionic gonadotropin), one used in human reproduction in the context of assisted reproductive technology treatments: ENDO 5000 (Schering-Plough laboratory) and the other used in veterinary medicine: Chorulon (MSD laboratory).

According to the protocol of Scobey et al. [13], the bioactivity of LH or of hCG was quantified with respect to the increase in weight of the seminal vesicles, the development of which is androgen-dependent. The weight varies proportionally to the activity of the hCG and thus makes it possible to quantify and compare the biological activity of the hormone injected alone or complexed with the antibody studied. The protocol was carried out with 25-day-old young rats that were injected subcutaneously, once a day for four days, with 100 µl of 1.5 IU of hCG or of a mixture of 1.5 IU hCG+2 µg of antibody, preincubated for 20 min at 37° C. On the fifth day, the rats were weighed and then sacrificed. Their seminal vesicles (SVs) were removed, dissected and weighed. The weight of the seminal vesicles is expressed in mg/100 g of body weight in order to be able to compare and combine the results obtained with various batches. In each experiment, each of the conditions was tested on a batch of five rats. The same experiment was repeated several times.

Figure 12:
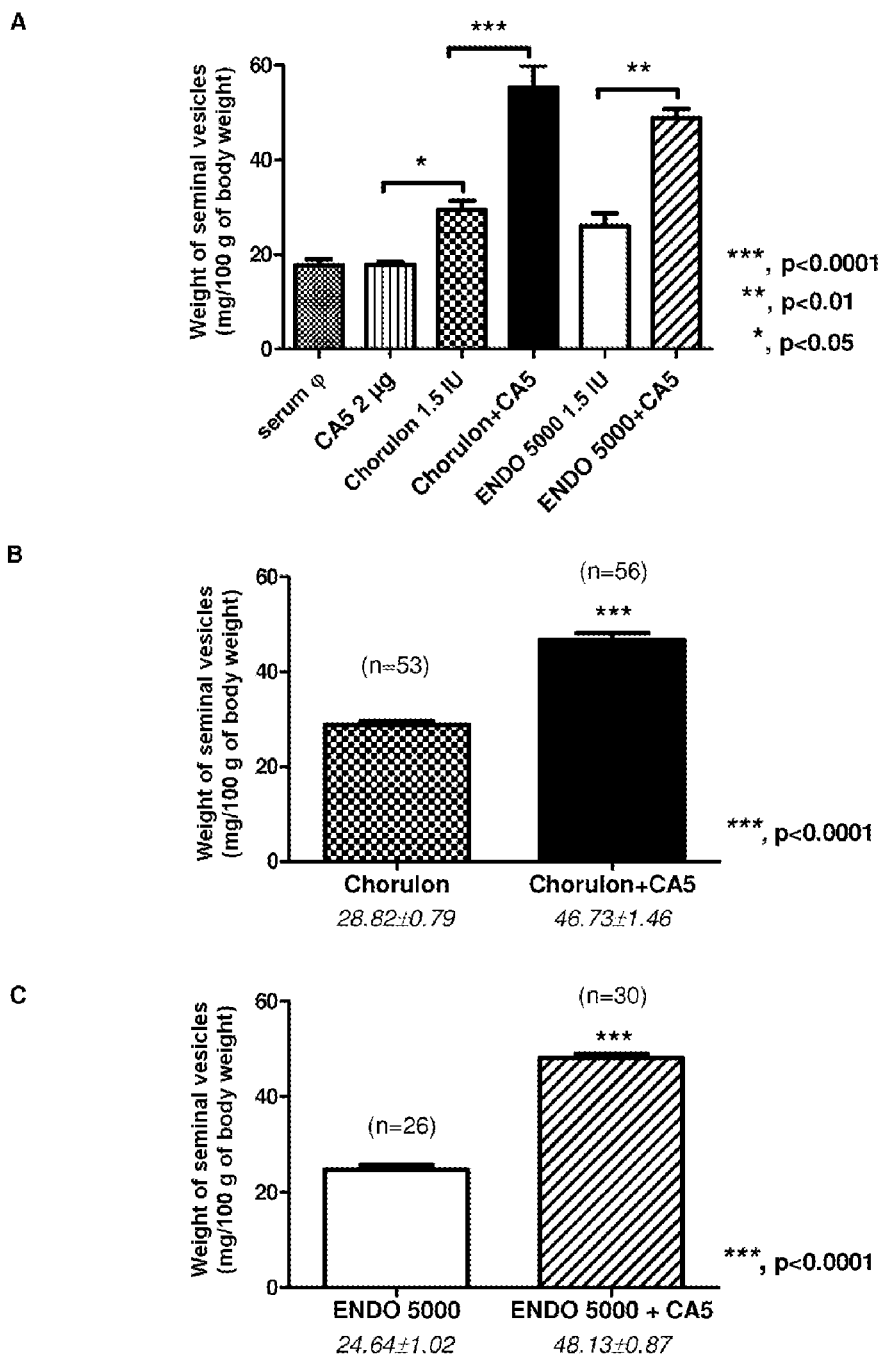
FIG. 12 represents the in vivo potentiating effect of the CA5 monoclonal antibody on the bioactivity of the human chorionic gonadotropins (hCG) Chorulon® and Endo 5000 in the male rat.

The effect of CA5 on the two preparations of hCG: Chorulon and Endo 5000 is shown in FIG. 12. Histogram A is a representative example of a bioassay carried out on six batches of five rats. A very significant potentiating effect ($p<0.0001$, Krustal and Wallis test) was obtained with the hCG Chorulon/CA5 complex with an increase of 196% in the weight of the seminal vesicles compared with the batch treated with hCG alone. A significant effect was also obtained with the hCG ENDO 5000/CA5 complex with an increase in the weight of 193% (p<0.01). It is observed that the batch treated with the CA5 antibody alone shows no change in the weight of the seminal vesicles compared with the control animals treated with physiological saline: the antibody alone exerts no effect on the target organ contrary to the complex.

The sum of the results obtained during the repetitions of this bioassay with the two hCGs confirms a highly significant potentiating effect (p<0.0001, unpaired t-test) of the hormone/CA5 complex:
- on numbers of 53 and 56 animals respectively, the mean weight of the SVs was 28.8 mg/100 g in the rats treated with the hCG Chorulon and 46.7 mg/100 g in the rats treated with the complex (increase of 162%) (FIG. 12B);
- on numbers of 26 and 30 animals respectively, the mean weight of the SVs was 24.64 mg/100 g in the rats treated with hCG ENDO 5000 and 48.13 mg/100 g in the rats treated with the complex (increase of 195%) (FIG. 12C).

The CH10 antibody also exhibited a significant potentiating effect on the hCG Chorulon and the hCG ENDO 5000, in vivo, in the rat.

Figure 13:
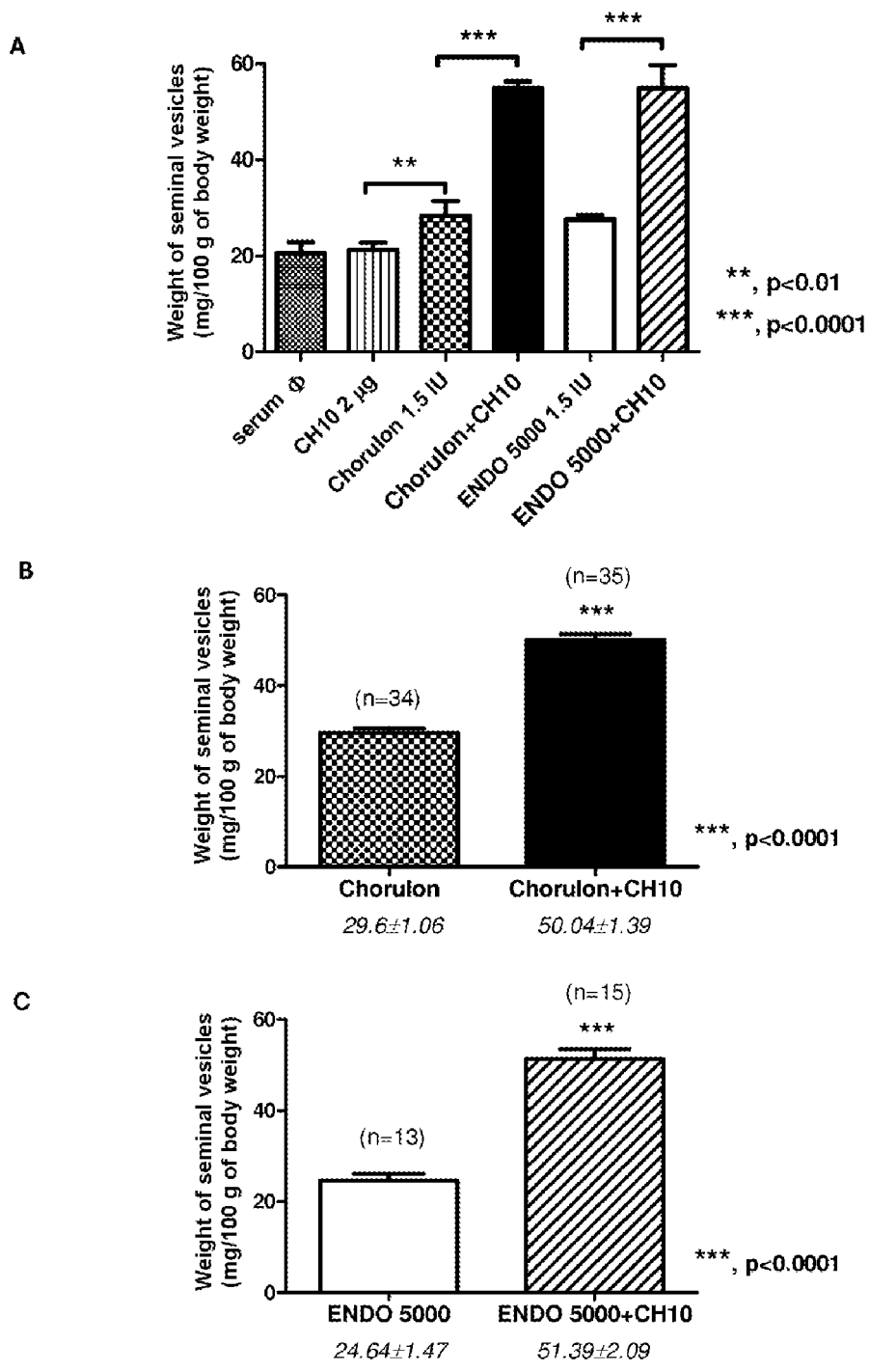
FIG. 13 represents the in vivo potentiating effect of the CH10 monoclonal antibody on the bioactivity of the human chorionic gonadotropins (hCG) Chorulon® and Endo 5000® in the male rat.

FIG. 13A illustrates a representative case of a bioassay carried out on six batches of five rats. A very significant potentiating effect (p<0.0001, Krustal and Wallis test) was obtained with the hCG Chorulon/CH10 complex with an increase of 193% in the weight of the seminal vesicles compared with the batch treated with hCG alone. A significant effect was also obtained on the batch treated with the hCG ENDO 5000/CH10 complex with an increase in the weight of 199% (p<0.0001). It is observed that the batch treated with the CH10 antibody alone shows no change in the weight of the seminal vesicles compared with the control animals treated with physiological saline. CH10 not complexed to the hormone thus has no specific effect on the target organ.

The compilation of the results obtained during the repetitions of this bioassay with the two hCGs confirms a highly significant potentiating effect (p<0.0001, unpaired t-test) of the hormone/CH10 complex:
- on numbers of 34 and 35 animals respectively, the mean weight of the SVs was 29.6 mg/100 g in the rats treated with the hCG Chorulon compared with 50.04 mg/100 g in the rats treated with the complex (increase of 169%) (FIG. 13B);
- on numbers of 13 and 15 animals respectively, the mean weight of the SVs was 24.64 mg/100 g in the rats treated with the hCG ENDO 5000 and 51.39 mg/100 g in the rats treated with the complex (increase of 208%) (FIG. 13C).

Example 4: In Vivo Measurement of the Potentiating Effect of the Ligands of the Invention on the Bioactivity of Endogenous Gonadotropins in Ewes After having demonstrated and characterized the potentiating effect in vivo, of the CA5 and CH10 monoclonal antibodies, in a rodent (small animal), the objective was to study the effect of each antibody on the activity of FSH in productive livestock, which are larger: ewes.

For this, a study was carried out on pubescent, Ile de France, ewes, all of the same age, with the aim of evaluating the potentiating effect of the antibodies on the treated ewes' own hormones (endogenous hormones). The study of the specificity showed strong binding of the CA5 and CH10 antibodies for ovine FSH and more variable binding for ovine LH. For this purpose, a treatment comprising only injection of an antibody alone was developed in order to evaluate the efficacy thereof.

In the protocols set up in ewes, each antibody was thus injected alone and not preincubated with the exogenous FSH, as was done in the studies in the female rat. Furthermore, each antibody was injected into ewes free of any prior stimulation of the ovary: the animals received no hormonal treatment for stimulating ovulation with a gonadotropin prior to the injection of the antibody.

The potentiating effect of the anti-FSH antibodies CA5 and CH10 was evaluated during protocols carried out right in the middle of the sexual season (January) or at the end of the sexual season (end of March). The protocols were all carried out on ewes in which the ovulatory cycle was presynchronized by implanting a vaginal sponge impregnated with a progestogen (45 mg of fluorogestone acetate (FGA)—MSD) for 14 days. The potentiating effect was analyzed by comparing the ovulatory response (number of ovulations) and the establishing of one or more functional corpora lutea of good quality (size of the progesterone secretion) in control ewes (physiological saline batch), ewes stimulated with a porcine FSH treatment (FSH batch) and ewes stimulated with an antibody alone (antibody batch).

In each protocol, a plasma LH assay was carried out by the ELISA method in order to detect and date the preovulatory peak of LH. To evaluate the ovulatory response, an endoscopic observation of the ovaries was carried out by laparoscopy, under anesthesia, eight days after withdrawal of the vaginal sponge, in order to count the number of corpora lutea and to observe their appearance.

To evaluate the functionality and the quality of the corpus luteum or corpora lutea, a quantitative progesterone ELISA assay was carried out using daily blood samples from the 1st to the 21st day after withdrawal of the sponge.

All the statistical analyses were carried out with the GraphPad Prism Version 5.0 software (GraphPad, San Diego, Calif., USA).

CA5 Antibody

The potentiating effect of the CA5 antibody (IgG) was evaluated in two protocols (1 and 2) in the sexual season period and at the end of sexual season.

In protocol 1, carried out at the end of sexual season:
- the "CA5 antibody" batch (n=6) received three injections of purified CA5, intramuscularly: 2 mg 4 days before the withdrawal of the sponge, 1 mg before the withdrawal and 1 mg at the time of the withdrawal of the sponge;
- the "control" batch (n=5) received an injection of physiological saline, intramuscularly, 24 h before the withdrawal of the sponge;
- the "FSH" batch (n=5) received an intramuscular injection of 100 μg of porcine FSH (pFSH) 24 h before the withdrawal of the sponge and of 90 μg 12 h before the withdrawal of the sponge.

The analysis of the ovulatory response gave the results presented in table 30 below.

TABLE 30

|  | Serum Φ batch | FSH batch | CA5 alone batch | Statistics |
|---|---|---|---|---|
| Number of ewes per batch | 5 | 5 | 6 |  |
| Number of ewes having ovulated per batch | 2/5 (40%) | 2/5 (40%) | 2/6 (35%) | NS |
| Number of corpora lutea per ewe having ovulated | 1.5 ± 0.7 | 3 ± 2.8 | 1.5 ± 0.7 | NS |
| Moment of the LH peak (hours after withdrawal) | 72 ± 17 | 60 ± 0 | 78 ± 25 | NS |

The statistical analysis was carried out by means of a Fisher's exact test.

Compared with the control and FSH batches, the results obtained in the CA5 batch do not show any significant effect on the ovulatory response. None of the parameters measured shows a trend.

Figure 14:
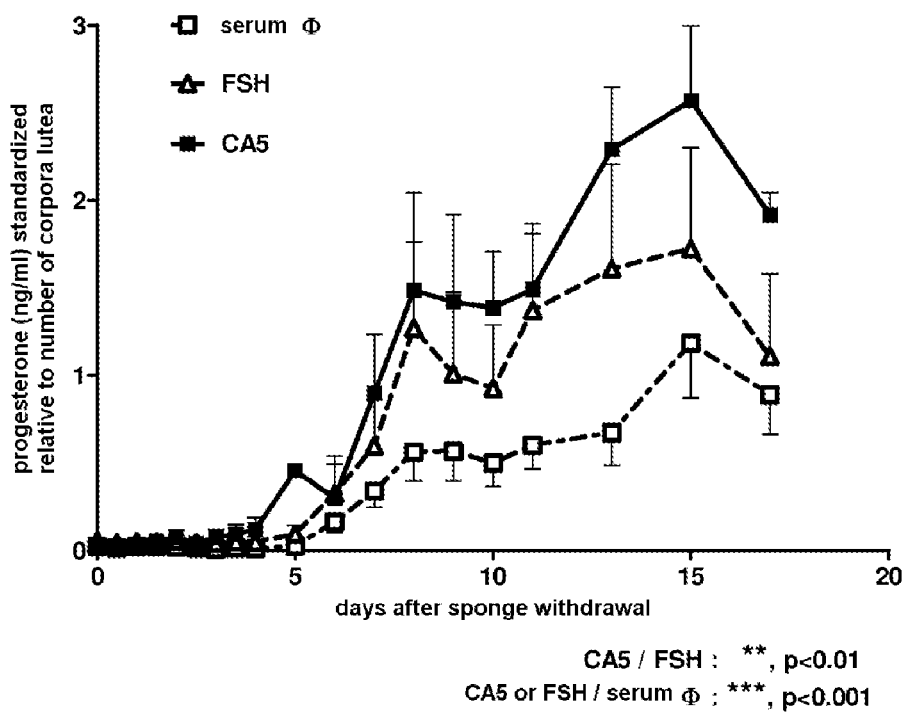
FIG. 14 represents the in vivo potentiating effect of the CA5 monoclonal antibody on the bioactivity of the endogenous gonadotropins in ewes at the end of the sexual season.
Figure 14:
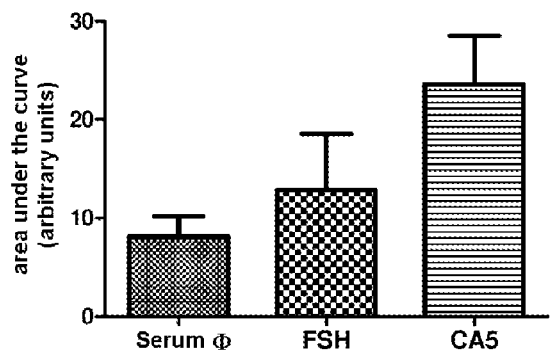

The progesterone secretion profile during the luteal phase obtained in the three batches is illustrated in FIG. 14. For each individual, the progesterone concentration values (ng/ml) were standardized with respect to the number of corpora lutea. Each curve represents the mean of the progesterone values obtained in the females of each batch at a time t.

A significant effect of the CA5 antibody was observed on the strength of progesterone secretion per corpus luteum and on the start of the establishing thereof (FIG. 14A). An effect is observed on the CA5 curve, compared with the curves of the FSH and serum φ batches, a beginning of progesterone secretion as early as D4 followed by a significant increase in the secretion which is maintained throughout the luteal phase until the end of cycle. The mean progesterone values at D10 are 1.38 ng/ml–0.92 and 0.52 ng/ml respectively for the CA5, FSH and serum D batches and 2.58–1.7 and 1.18 ng/ml at D15. The comparison of the three curves was carried out using a paired non-parametric t test (Wilcoxon test). Thus, the curve of the CA5 batch is higher than the curve of the FSH batch and significantly different ($p<0.01$), likewise with the curve of the control batch ($p<0.001$). The curve of the FSH batch is higher and significantly different than that of the control batch ($p<0.001$).

To quantify this significant and constant increase in the level of progesterone secretion until the end of cycle in the ewes under CA5 stimulation, the area under the curve (AUC) was calculated with the GraphPad Prism version 5.0 software. The results are shown in FIG. 14B and show that the AUC of the CA5 curve (23.61 arbitrary units) tends to be higher than the AUC of the serum φ curve (8 units), but this difference is not significant. Likewise, the AUC of the FSH curve (12 units) is not significantly different than the control curve.

In conclusion, the injection of CA5 in ewes gives the same results as a conventional treatment with FSH in terms of ovulation induction, but enables faster establishment of progesterone secretion and the maintaining of a more effective functional corpus luteum with a higher circulating progesterone level, guaranteeing a better success of the early embryonic development and the maintaining of gestation (decreased risk of abortion).

In protocol 2, carried out in the sexual season:
the "CA5 antibody" batch (n=7) received a single intramuscular injection of 2 mg of CA5 antibody 24 h before withdrawal of the sponge;
the "control" batch (n=9) received an injection of physiological saline, intramuscularly, 24 h before the withdrawal of the sponge;
the "FSH" batch (n=11) received an intramuscular injection of 100 µg of porcine FSH (pFSH) 24 h before the withdrawal of the sponge and of 90 µg 12 h before the withdrawal of the sponge.

The analysis of the ovulatory response gave the results presented in table 31 below. The statistical analysis was carried out by means of a Fisher's exact test.

TABLE 31

|  | Serum Φ batch | FSH batch | CA5 alone batch | Statistics |
|---|---|---|---|---|
| Number of ewes per batch | 9 | 11 | 7 |  |
| Number of ewes having ovulated per batch | 4/9 (44%) | 4/11 (36%) | 7/7 (100%) | ***, $p < 0.0001$ |
| Number of corpora lutea per ewe of the batch | 0.67 ± 0.3 | 0.9 ± 0.5 | 1.5 ± 0.4 | NS, $p = 0.06$ |
| Number of corpora lutea per ewe having ovulated | 1.5 ± 0.3 | 3 ± 1.4 | 1.5 ± 0.4 | NS |
| Moment of the LH peak (hours after withdrawal) | 64 ± 13 | 56 ± 7 | 57 ± 4.4 | NS |

Compared with the control and FSH batches, the results obtained in the CA5 batch show a very significant effect of the antibody injected alone on the ovulatory response. Indeed, 100% of the females (7/7) having received an injection of 2 mg of antibody ovulated, compared with 44% and 36% respectively for the serum φ batch and the FSH batch ($p<0.0001$, Fisher's exact test). The number of corpora lutea obtained per female on the total numbers of the batch is likewise greater in the "CA5" batch, almost significantly ($p=0.06$, Mann-Whitney t test): 1.5 corpora lutea compared with 0.9 (FSH) and 0.67 (serum φ) respectively. The mean number of corpora lutea per female having ovulated is not significantly different between the three batches.

The mean moment of appearance of the LH peak is not significantly different between the three batches. Despite everything, a tendency toward less variability in the arrival of the LH peak (and thus in the moment of ovulation) is observed in the CA5 batch compared with the FSH batch and especially serum φ batch.

Figure 15:
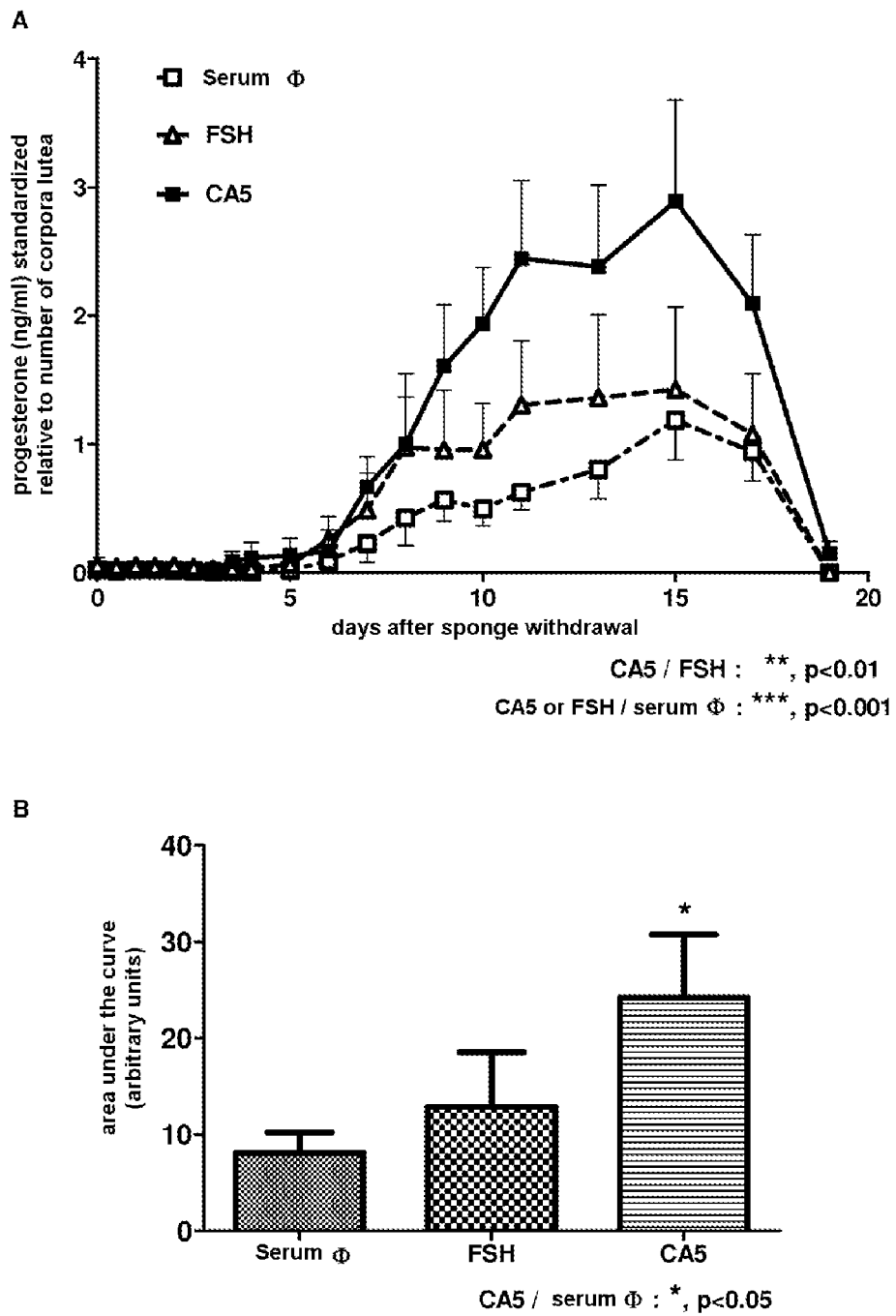
FIG. 15 represents the in vivo potentiating effect of the CA5 monoclonal antibody on the bioactivity of the endogenous gonadotropins in ewes during the period of the sexual season.

The progesterone secretion profile during the luteal phase following the ovulation is shown in FIG. 15A. For each individual, the progesterone concentration values (ng/ml) were standardized with respect to the number of corpora lutea. Each curve of the figure represents the mean of the progesterone values obtained in the females of each batch. A notable effect of the CA5 antibody was observed on the strength of the progesterone secretion: a considerable and very significant increase in progesterone secretion per corpus luteum was observed throughout the luteal phase compared with the curves of the FSH batch and of the serum φ batch. The mean values at D10 are 2.44 ng/ml, 1.3 and 0.62 ng/ml respectively for the CA5, FSH and serum φ batches, and 2.88–1.42 and 1.18 ng/ml at D15. The comparison of the three curves was carried out by means of a paired non-parametric t test (Wilcoxon test). The curve of the CA5 batch is significantly higher and different than the curve of the FSH batch (p<0.01), likewise with the curve of the control batch (p<0.001). The curve of the FSH batch is significantly different than that of the control batch (p<0.001).

To quantify this notable and constant increase in the progesterone secretion level per corpus luteum throughout the luteal phase of the cycle in the ewes under CA5 stimulation, the area under the curve (AUC) was calculated with the GraphPad Prism version 5.0 software. The results are shown in FIG. 15B and show that the AUC of the CA5 curve (24.20 units) is significantly higher by a factor of 3 than the AUC of the serum ϕ curve (8.1) (p<0.05, non-parametric Mann-Whitney t-test). Conversely, the AUC of the FSH curve is not significantly different than the control curve.

In conclusion, the use of the CA5 antibody in the form of a single intramuscular injection of 2 mg gave, very significantly, better results than a conventional treatment with FSH, allowing:

1—the induction of ovulation in 100% of the females stimulated,
2—the development of corpora lutea of better quality with progesterone secretion much higher than that observed following an FSH treatment and a very fast establishment as early as D4. It should be emphasized that the impact on this additional property of CA5 compared with an FSH treatment is very important. This is because the plasma progesterone concentration is a key factor in embryonic development, particularly in its early phases.

The faster establishing of progesterone secretion and the maintaining of a more effective functional corpus luteum with a higher circulating progesterone level is the guarantee of a better success of the early embryonic development and of the maintaining of gestation with a decreased risk of abortion.

All of the results indicate that the potentiating antibodies, particularly CA5, injected in vivo in ewes is capable of complexing the animal's endogenous gonadotropic hormones and of potentiating the biological activity of the animal's own hormones.

The potentiating effect of the CA5 antibody in ewes is capable of inducing a stimulation of the ovary stronger than the conventional FSH hormonal treatment: ovulation induction is 100% in the sexual season and in all cases a considerable increase in circulating progesterone concentration, of 200% to 300%, is maintained throughout the luteal phase. This additional effect is major for reducing progestogen-dependent embryonic development failure rates and the risks of abortion.

Example 5: In Vivo Measurement of the Potentiating Effect of the Ca5 Ligand of the Invention on the Bioactivity of Endogenous Gonadotropins in Heifers After having demonstrated and characterized the potentiating effect of the CA5 monoclonal antibody in rats and ewes, the objective was to study its effect on the activity of endogenous gonadotropins in a larger animal: the heifer. For this, a treatment comprising only the injection of the antibody alone was developed in Prim'Holstein heifers so as to evaluate the efficacy thereof. These heifers were free of any prior stimulation of the ovary, the animals having received no ovulation-stimulating hormonal treatment with a gonadotropin prior to the injection of the antibody.

The protocol aiming to evaluate the potentiating effect of the CA5 antibody was carried out on Prim'Holstein heifers 20 to 22 months old, the ovulatory cycle of which was synchronized beforehand by implanting a progestogen implant (3.3 mg Norgestomet, Crestar®—MSD) for 7 days. An injection of GnRH (0.004 mg of buserelin acetate, Crestar® Pack—MSD) was carried out on the day the implant was implanted, followed by an injection of prostaglandins 24 hours before the withdrawal of the implant (Prosolvin®—Virbac).

The animals were separated into two batches:
the "CA5" batch (n=4) received two injections of 11 mg of purified CA5 antibody intramuscularly: the first given 24 hours after the implantation of the implant and the second given 24 hours before the withdrawal of the progestogen implant;
the "control" batch (n=3) received two injections of physiological saline, intramuscularly, the first given 24 hours after the implantation of the implant and the second given 24 hours before the withdrawal of the progestogen implant.

The potentiating effect was analyzed by comparing the ovulatory response (ovulation or no ovulation) and the establishment of a functional corpus luteum of good quality (size of the corpus luteum and size of the progesterone secretion) in the control heifers (physiological saline batch), and in the heifers treated with the antibody alone (CA5 batch).

A plasma LH and estradiol assay was carried out by the ELISA method in order to detect and date the pre-ovulatory LH peak, and to monitor the estradiol secretion. To evaluate the ovulatory response and the size of the corpora lutea, ovarian ultrasounds were carried out daily. Finally, to evaluate the functionality and the quality of the corpus luteum, a quantitative progesterone ELISA assay was carried out on daily blood samples from the day of the implantation of the implant to the 21st day after withdrawal of the implant.

The heifers were inseminated and a gestation diagnosis was performed by ultrasound 35 days after insemination.

All the statistical analyses were performed with the GraphPad Prism Version 5.0 software (GraphPad, San Diego, Calif., USA).

Figure 16:
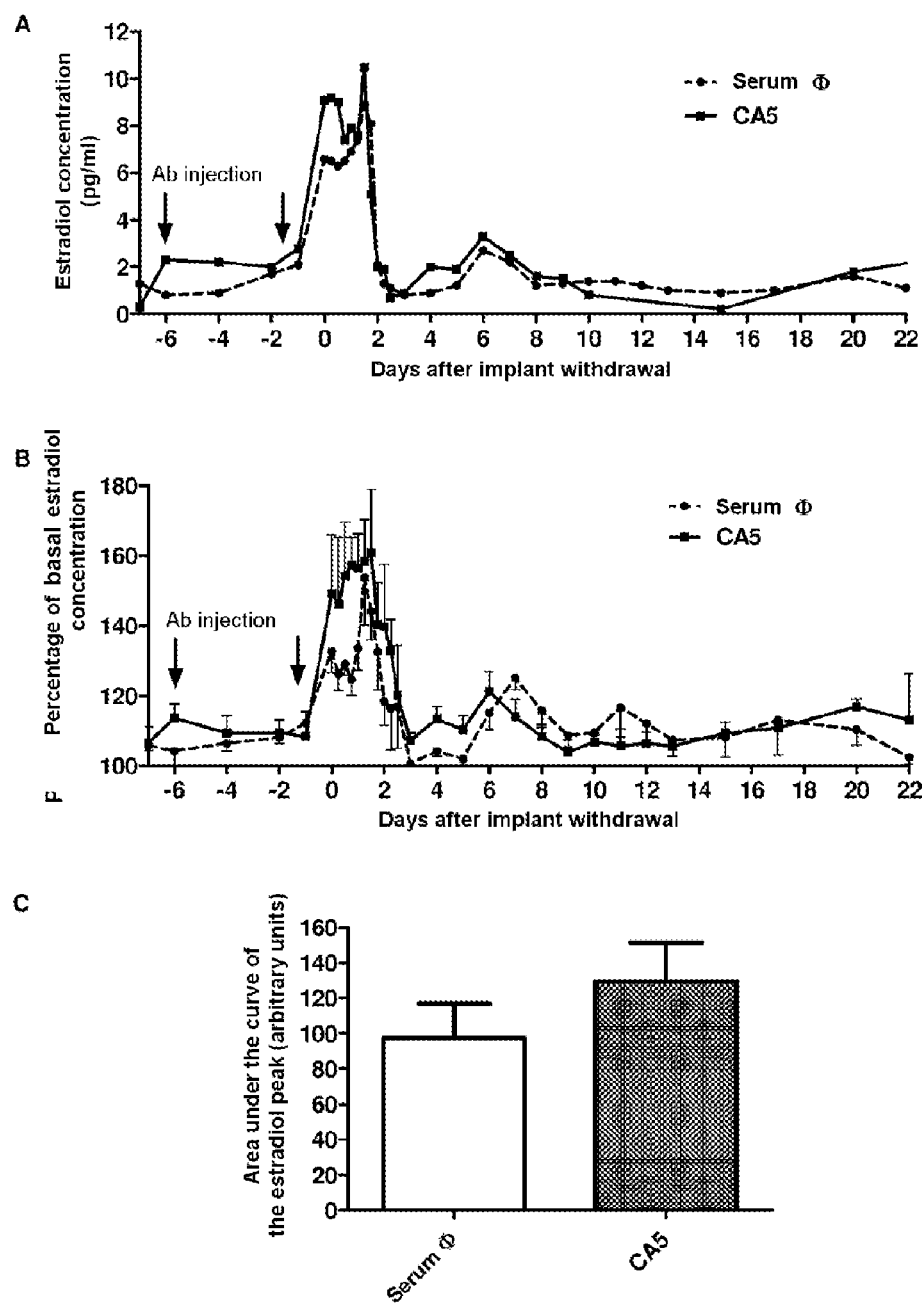
FIG. 16 represents the in vivo potentiating effect of the CA5 monoclonal antibody injected alone, on the endogenous gonadotropins in heifers: effect on estradiol secretion.

The ovulatory response was first of all compared in the two batches of heifers by measuring the circulating estradiol levels. The results presented in FIG. 16A show the estradiol secretion profile in two heifers representative of each batch. The estradiol peak observed at D0 is greater in amplitude in the treated animal, with a concentration of 9.2 pg/ml compared with 6.6 pg/ml in the control at D0 and of 10.5 pg/ml compared with 8.8 pg/ml in the control at D1.5 (not significant). The mean of the results of the heifers of each batch is represented as a percentage of the basal estradiol concentration measured when the implant is implanted (FIG. 16B). The same tendencies are found, with an estradiol peak of which the amplitude tends to be greater in the batch treated with the CA5 antibody compared with the heifers of the control batch: at withdrawal of the implant (D0), with 149±16% compared with 133±7% and, at D1.5 after withdrawal of the implant, 161±6% compared with 144±8% (not significant). The estradiol level between D3 and D8 indicates, in both batches, a second, smaller, secretion peak, reflecting a second follicular wave. In the CA5 batch, the increase in the estradiol concentration tends to be earlier than in the control batch: at D6, it is 113±3% in the heifers treated with CA5 compared with 104±0.5 in the controls.

The analysis of the area under the curve of the estradiol peak in the two batches of heifers (FIG. 16C) also illustrates a tendency, although this is not significant, toward obtaining a higher estradiol peak in the batch treated with CA5 (area of 129.5±20 units) than in the control batch (area of 97.5±18 units).

Overall, the results show a tendency, although not significant, to have better estradiol secretion in the heifers treated with the CA5 antibody, which may reflect a better quality of the follicular phase.

Figure 17:
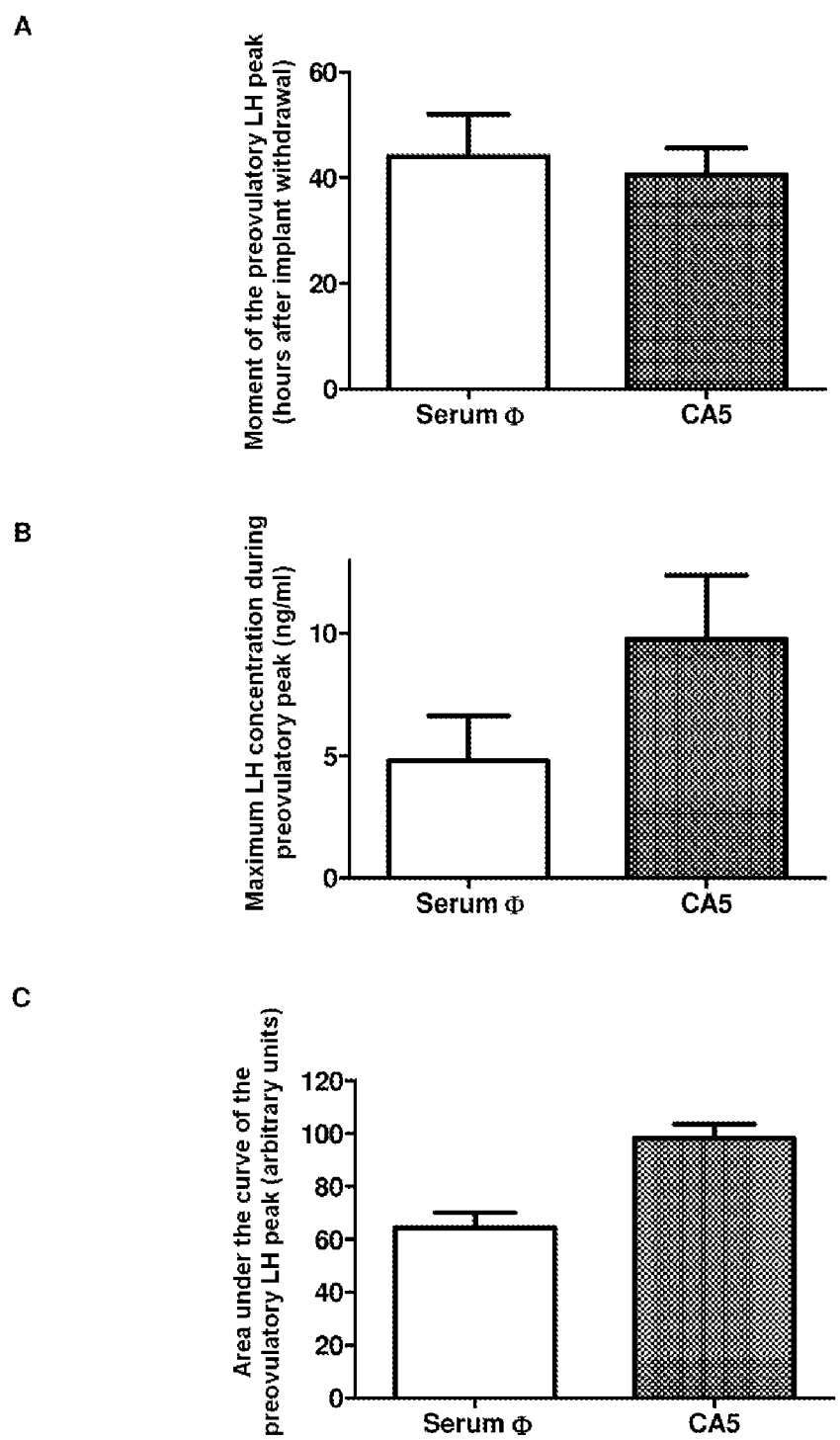
FIG. 17 represents the in vivo potentiating effect of the CA5 monoclonal antibody injected alone, on the endogenous gonadotropins in heifers: effect on the characteristics of the preovulatory LH peak.

The results regarding the preovulatory LH peak are shown in FIG. 17. They show no difference in relation to the moment at which the LH peak appears (FIG. 17A): in the control batch, the LH peak occurs 44 h±8 h after withdrawal of the implant, compared with 40.5 h±5.1 h in the batch treated with the CA5 antibody. The maximum concentration of the LH peak is 4.8±1.8 ng/ml of LH in the control batch compared with 9.8±1.2 ng/ml in the heifers treated with the CA5 antibody (FIG. 17B). The maximum LH concentration during the preovulatory peak tends to be greater in the batch treated with the antibody, but this tendency is not significant. The same tendency is observed with respect to the area under the curve of the preovulatory LH peak: it is 64.5±5.8 arbitrary units in the control heifers compared with 98±4.8 in the heifers treated with the CA5 antibody (FIG. 17C). This tendency toward a greater LH peak in the heifers treated with CA5 is not however significant.

The ultrasound analysis after the ovulation indicated that all the heifers of the two batches had had a single ovulation.

The quality of the luteal phase was subsequently analyzed by regularly measuring the size of the corpus luteum by ultrasound in order to monitor its development. The results shown in FIG. 18A indicate that the batch of heifers treated with CA5 tends to have a larger corpus luteum (26±2 mm in diameter) than the batch of control heifers (22±1 mm in diameter). Nevertheless, this difference is not significant.

Figure 18:
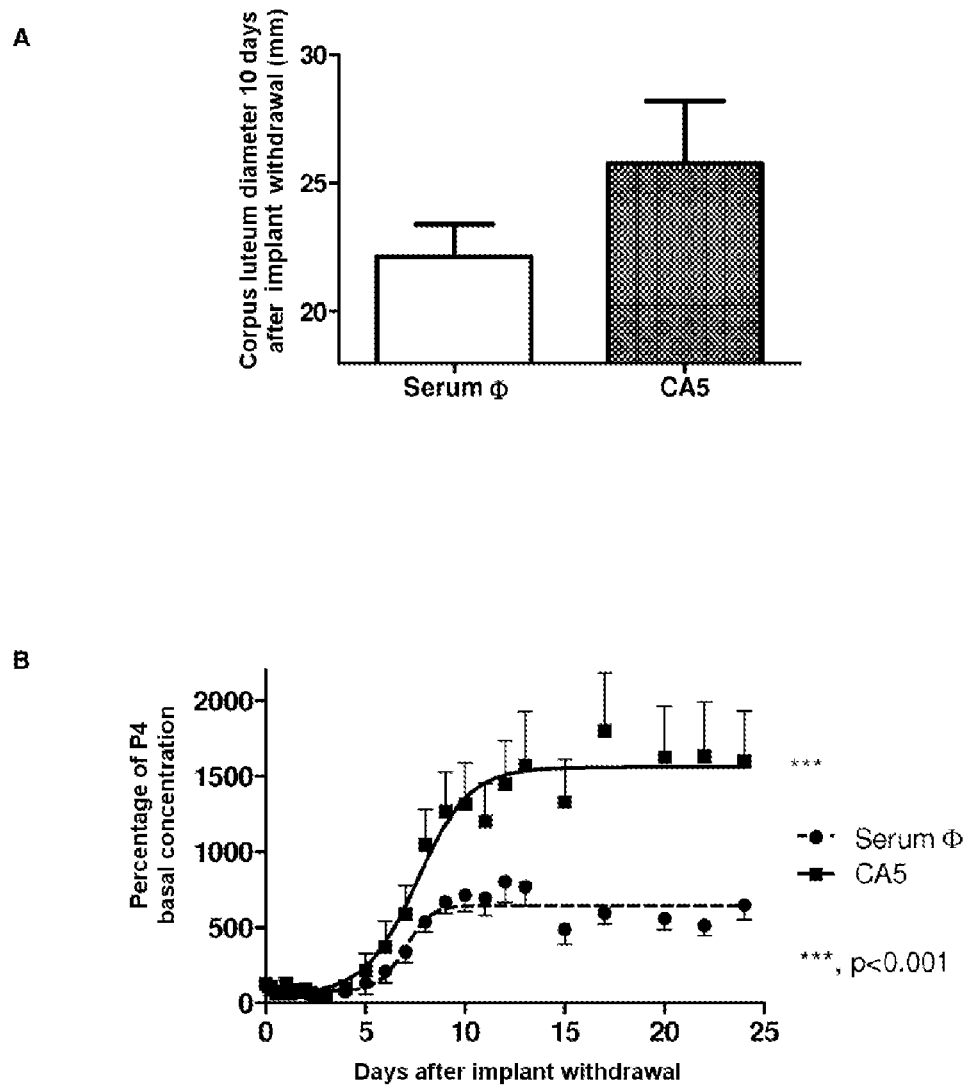
FIG. 18 represents the in vivo potentiating effect of the CA5 monoclonal antibody injected alone, on the endogenous gonadotropins in heifers: effect on the progesterone secretion.

The measurement of the plasma progesterone concentration throughout the luteal phase is represented in FIG. 18B. It reveals a very significant difference between the two batches ($p<0.001$). The circulating progesterone level is expressed as a percentage of the basal concentration measured at withdrawal of the implant. At D9 after withdrawal it is 668±85% in the control batch compared with 1266±254% in the batch treated with the antibody, that is to say a 1.9-fold increase compared with the control batch. At D20 after withdrawal it is 646±74% in the control batch compared with 1598±327% in the batch treated with the antibody, that is to say a 2.47 fold increase compared with the control batch. These results reflect a better quality of the corpus luteum with a tendency to have a greater diameter and especially higher progesterone secretion in the heifers treated with the CA5 antibody. It should be emphasized that a better functional quality of the corpus luteum during the luteal phase is predominant in the success of the implantation of the embryo and of its early development. It reduces the risks of early abortions.

The gestation diagnoses carried out 35 days after artificial insemination indicated that all the heifers in each of the batches were gestating.

In conclusion, these results show that the heifers treated with the CA5 antibody tend to have a better estrogenic response, although this is not significant, during the follicular phase and have a significantly higher progesterone secretion during the luteal phase.

Example 6: In Vivo Measurement of the Potentiating Effect of the Ca5 Ligand of the Invention on the Bioactivity of Endogenous Gonadotropins in Female Monkeys After having demonstrated and characterized the potentiating effect of the CA5 monoclonal antibody in vivo in rats, ewes and heifers, its potentiating effect was studied in a species close to humans: the Cynomolgus monkey (Macaca fascicularis). For this, a study was carried out on pubescent macaques at least 36 months old, with the aim of evaluating the potentiating effect of the antibody on human FSH and on the endogenous hormone of the macaque treated.

For this, a study was carried out on four pubescent macaques at least 36 months old. The CA5 antibody was injected either 20 minutes after an injection of exogenous FSH, or alone. On the first day of menstruation, the macaques received an injection of 1.5 mg of sustained-release GnRH preparation (Decapeptyl® L.P. 3 mg—IPSEN Pharma) intramuscularly. Fifteen days later, the four female monkeys received a different treatment:

animal treated with 25 IU for 8 days ("25 IU×8" batch):
  a daily injection of 25 IU of human FSH (Gonal-f® prefilled pen—Merck Serono) was carried out subcutaneously, for 8 days;

animal treated with 25 IU on one day ("25 IU×1" batch):
  a single injection of 25 IU of human FSH (Gonal-f® prefilled pen—Merck Serono) subcutaneously was carried out on the first day of treatment;

animal treated with CA5+hFSH ("CA5+hFSH" batch): a single injection of CA5 antibody (80 µg) was carried out subcutaneously 20 minutes after the injection of 25 IU of human FSH (Gonal-f® prefilled pen—Merck Serono), on the first day of treatment only;

animal treated with CA5 alone ("CA5" batch): a single injection of CA5 antibody alone (88.5 µg), was carried out subcutaneously without injection of exogenous hormone, on the first day of treatment only.

The potentiating effect was analyzed by comparing the follicular growth induced by the treatment. For this, transabdominal ovarian ultrasounds were performed every 48 hours in order to count the follicles and to measure their surface area (expressed in $mm^2$).

Figure 19:
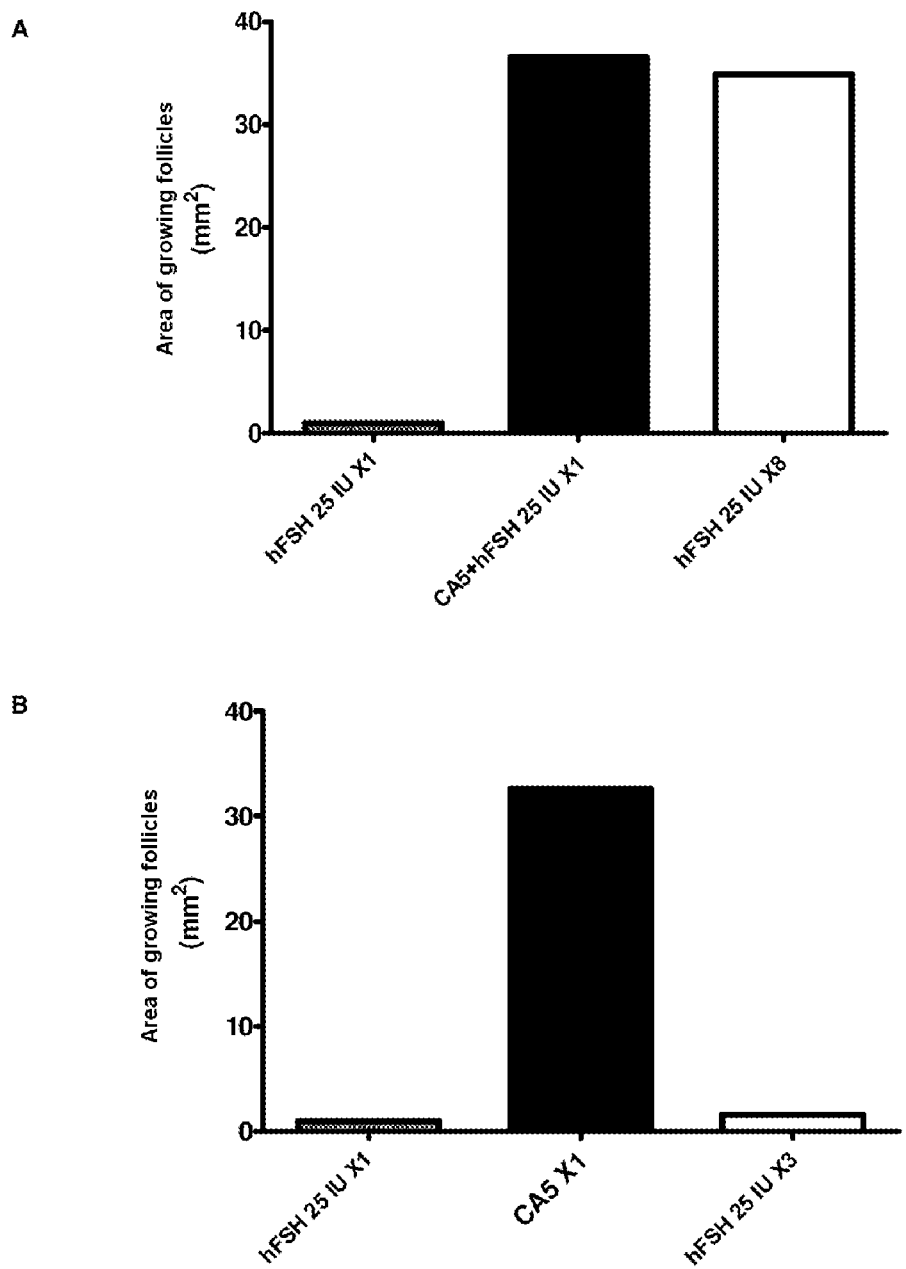
FIG. 19 represents the in vivo potentiating effect of the CA5 monoclonal antibody injected alone after 25 IU of hFSH, on follicular growth in female monkeys.

The effect obtained with an injection of the CA5 antibody carried out 20 minutes after injection of 25 IU of hFSH ("CA5+hFSH" batch) was compared to that of an injection of 25 IU of hFSH ("25 IU×1" batch) and to that of eight daily injections of 25 IU of hFSH ("25 IU×8" batch). The results shown in FIG. 19A show that, on the 9th day after the beginning of the FSH treatment, the female monkey treated with a single injection of 25 IU of hFSH exhibits no stimulated follicle (area under the curve, zero). Conversely, the female monkey treated a single time with the "CA5+hFSH" mixture on the first day of treatment exhibited eight growing follicles with a total area of the follicles of 37 $mm^2$ equal to that measured in the female monkey having received eight injections of hFSH ("25 IU×8"), which was 35 $mm^2$ with 11 stimulated follicles. A single injection of the CA5+25 IU hFSH complex thus stimulated the ovaries as effectively as eight injections of 25 IU of hFSH. This result demonstrates a potentiating effect of CA5, in vivo in female monkeys, resulting in follicular stimulation. Indeed, since the half-life of FSH is less than one hour, the effects observed with CA5 cannot be attributed solely to an effect on the injected hFSH, but also reflect an effect on the endogenous FSH of the female monkey.

The effect of an injection of the CA5 antibody injected alone ("CA5") was then studied and compared to that of an injection of 25 IU of hFSH ("25 IU×1") and to that of three daily injections of 25 IU of hFSH ("25 IU×3" batch). A stimulatory effect of the antibody injected alone was optimally observed three days after its injection. The results shown in FIG. 19B show that, on the 3rd day of the treatment, the female monkey having received a single injection of antibody alone ("CA5") exhibits ovarian stimulation with five growing follicles representing an area of 32.6 $mm^2$. In comparison, the female monkey having received three injections of 25 IU of hFSH ("25 IU×3") exhibited only a very weak stimulation with just one growing follicle, the area of which was 1.6 mm². Beyond the 3rd day of treatment, the ovarian stimulation induced by CA5 alone was not maintained and the stimulated follicles disappeared. A further injection of antibody or the adjustment of the dose injected on D1 would probably have been necessary in order to maintain the stimulatory effect on the ovaries. This result nevertheless indicates that the CA5 antibody injected alone was capable of complexing the endogenous FSH of the female monkey and of potentiating its biological activity sufficiently to induce the beginning of ovarian stimulation.

Example 7: Prediction of the Epitope Recognized by the CA5 and CH10 Ligands of the Invention, and Prediction of their Paratope The respective epitope of the CA5 and CH10 antibodies was determined on the gonadotropic hormones of various species using a protein-docking algorithm based on protein structure modeling using a Voronoï diagram and optimization by various score function evolutionary learning methods making it possible to differentiate native and non-native conformations (Bernauer et al., Bioinformatics 2007, 5:555) [14], (Bernauer et al., Bioinformatics 2008, 24:652) [15], (Bourquard et al., PLoS One 2011, 6:e18541) [16] and (Bourquard et al., Sci. Reports 2015, 5:10760) [17].

Each antibody was docked with human FSH (hFSH), human LH (hLH), the human CG (hCG), ovine FSH (oFSH) and ovine LH (oLH), porcine FSH (pFSH) and porcine LH (pLH). The crystallographic structures of hFSH and of hCG are available in the Protein Data Bank (PDB): 4MQW and 1QFW respectively. The structure of human FSH complexed with the extracellular domain of the human FSH receptor was used (Fan and Hendrickson, Nature 2005, 433:269) [18]. For the other hormones (hLH, oFSH, oLH, pFSH and pLH), homology models were produced and then used for the docking.

1/Epitope and Paratope of the CA5 Ligand

Since the 3D structure of the CA5 antibody is not available, the study was carried out using the sequences of the monovalent VH and VL fragments of CA5. For this, variable part homology models were produced. The VH and VL models were produced separately, from different structures, and their relative orientation was determined from the structure having served as support for the VH modeling. The structures used for the homology models are available in the Protein Data Bank (PDB): 3OKK for the CA5 VH and 3MBX for the CA5 VL.

Figure 20:
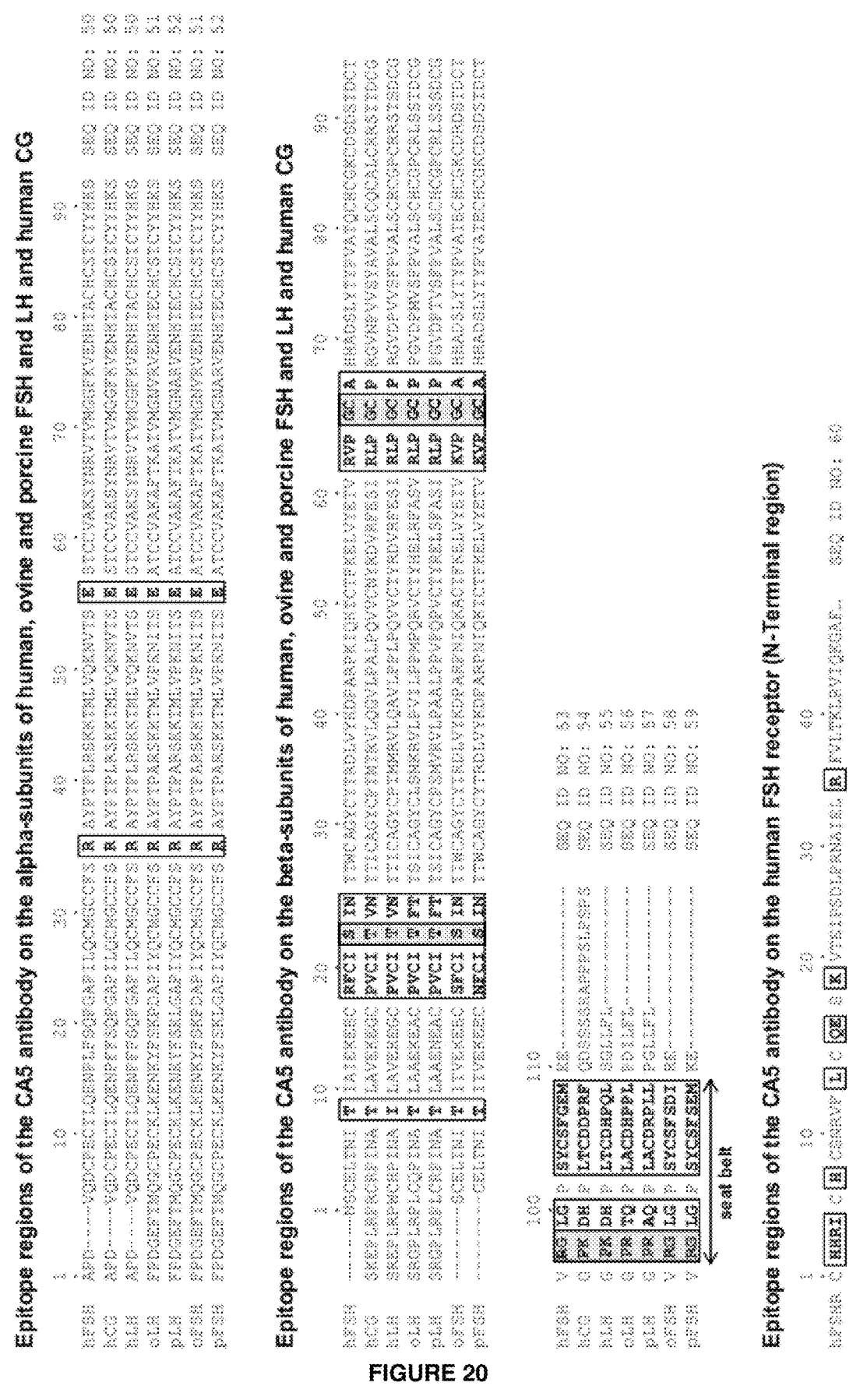

The docking results are shown in FIG. 20. It appears that the CA5 ligand docks similarly on the seven target hormones. The epitope is defined by several regions located discontinuously on the beta-subunit essentially and, for two residues, on the alpha-subunit of the gonadotropins studied. The epitope also involves ten residues of the ectodomain of the human FSH receptor. The epitope of the CA5 ligand is thus highly conformational: it is made up of several sequential regions of the hormone and of a sequence of the receptor, which are spatially close in the native conformation of the hormone and of the activated receptor.

The various residues of the hormone and of the receptor that are involved in the interface with the CA5 ligand are surrounded by rectangles in FIG. 20. The five residues denoted by a shaded area on the beta-subunit of hFSH are involved in the main interaction and have a major role in the antibody/antigen recognition: these are the serine in position 22 (Ser22), the glycine in position 65 (Gly65), the cysteine in position 66 (Cys66), the arginine 97 (Arg97) and the glycine 98 (Gly98) on the beta-subunit of hFSH. The Gly65 and Cys66 residues are present in the sequence of all the other target hormones.

The CA5 ligand also recognizes residues 97 to 100 and 102 to 109 in the C-terminal end of the FSH beta-subunit. This region, which constitutes a seat belt, plays a major role in stabilizing the association of the alpha/beta dimer of the hormone. It thus appears that the binding of the CA5 ligand to the hormone makes safe the closure of the seat belt and thus contributes to the stability of the dimer, which is essential for the bioactivity of the hormone (only the dimer is active).

The CA5 antibody is essentially directed against the beta-subunit of hFSH.

Only two residues of the alpha-subunit are involved in the interface: these are the arginine residue in position 35 (Arg35) and the glutamic acid residue in position 56 (Glu56) which are spatially close in the native hormone. Their role is to fix the C-terminal end of the beta-subunit in order to maintain the "seat belt" around the alpha-subunit. These two residues are constantly present and recognized in all the target hormones. They play a very important role in the bioactivity of the hormone.

Another characteristic of the epitope of the CA5 antibody is the involvement of the His2-His3-Arg4-Ile5, His7, Leu14, Gln16-Glu17, Lys19 and Arg35 residues of the N-terminal region of the human FSH receptor, in the interface recognized by the CA5 antibody.

TABLE 32

Epitope and paratope of the CA5 ligand. The bolded residues are involved in the main interaction zone

| Epitope regions on human FSH | | Paratope of the CA5 antibody |
|---|---|---|
| αFSH | Arg35 | VL: CDR1 |
|  | Glu56 | VL: CDR1 |
| βFSH | Thr9 | VH: CDR2 |
|  | Arg18 Phe19 Cys20 Ile21 Ser22 Ile23 Asn24 | VH: CDR1-CDR2-CDR3 |
|  | Arg62 Val63 Pro64 Gly65 Cys66 Ala67 | VH: CDR1-CDR2-FR |
|  | Arg97 Gly98 Leu99 Gly100 - Ser102 | VH: CDR3 |
|  | Tyr103 Cys104 Ser105 Phe106 Gly107 Glu108 Met109 | VL: CDR1-CDR2-CDR3-FR |
| Epitope regions on the human FSH receptor | | |
|  | His2 His3 Arg4 Ile5 - His7 | VL: CDR2-FR |
|  | Leu14 - Gln16 Glu17 - Lys19 | VL: CDR1-CDR2-FR |
|  | Arg35 | VL: CDR1 |

Table 32 shows the various regions constituting the epitope of the CA5 ligand and those constituting its paratope.

The two VH and VL chains are involved in the recognition of the hormone, via their three CDRs and some residues of their frameworks.

The five residues involved in the main interaction are recognized by Asn53 of the VH CDR2, residues Asp31, Phe27 and Thr28 of the VH CDR1 and residues Ser33 and Asn34 of the VL CDR1.

Only the VL chain is involved in the recognition of the ectodomain of the FSH receptor, particularly residues Gln35 and Lys36 of its CDR1, residue Ser58 of its CDR2 and several residues of framework 3.

In conclusion, the CA5 ligand recognizes a conformational epitope involving the alpha-subunit and the beta-subunit of hFSH and its C-terminal end forming the seat belt, and also the ectodomain of the FSH receptor. The VL chain is the only one involved in the interaction with the ectodomain of the receptor. The two VH and VL chains are involved in the interaction with the subunits of the hormone. The conformational epitope of the CA5 ligand enables it, on the one hand, to stabilize the hormone dimer association and, on the other hand, to stabilize the binding of the hormone to its receptor. These two mechanisms are complementary and fundamental for resulting in better interaction of the hormone on its receptor and thus obtaining better efficacy. They thus appear to constitute the mechanistic bases of the potentiating effect of the CA5 ligand on gonadotropins.

2/Epitope and Paratope of the CH10 Ligand

Since the 3D structure of the CH10 antibody is not available, the study was carried out using the sequences of the monovalent VH and VL fragments of CH10. For this, variable part homology models were produced. The VH and VL models were produced separately, from different structures, and their relative orientation was determined from the structure having served as a support for the VH modeling. The structures used for the homology models are available in the Protein Data Bank (PDB): 4QNP for the CH10 VH and 3D85 for the CH10 VL.

Figure 21:
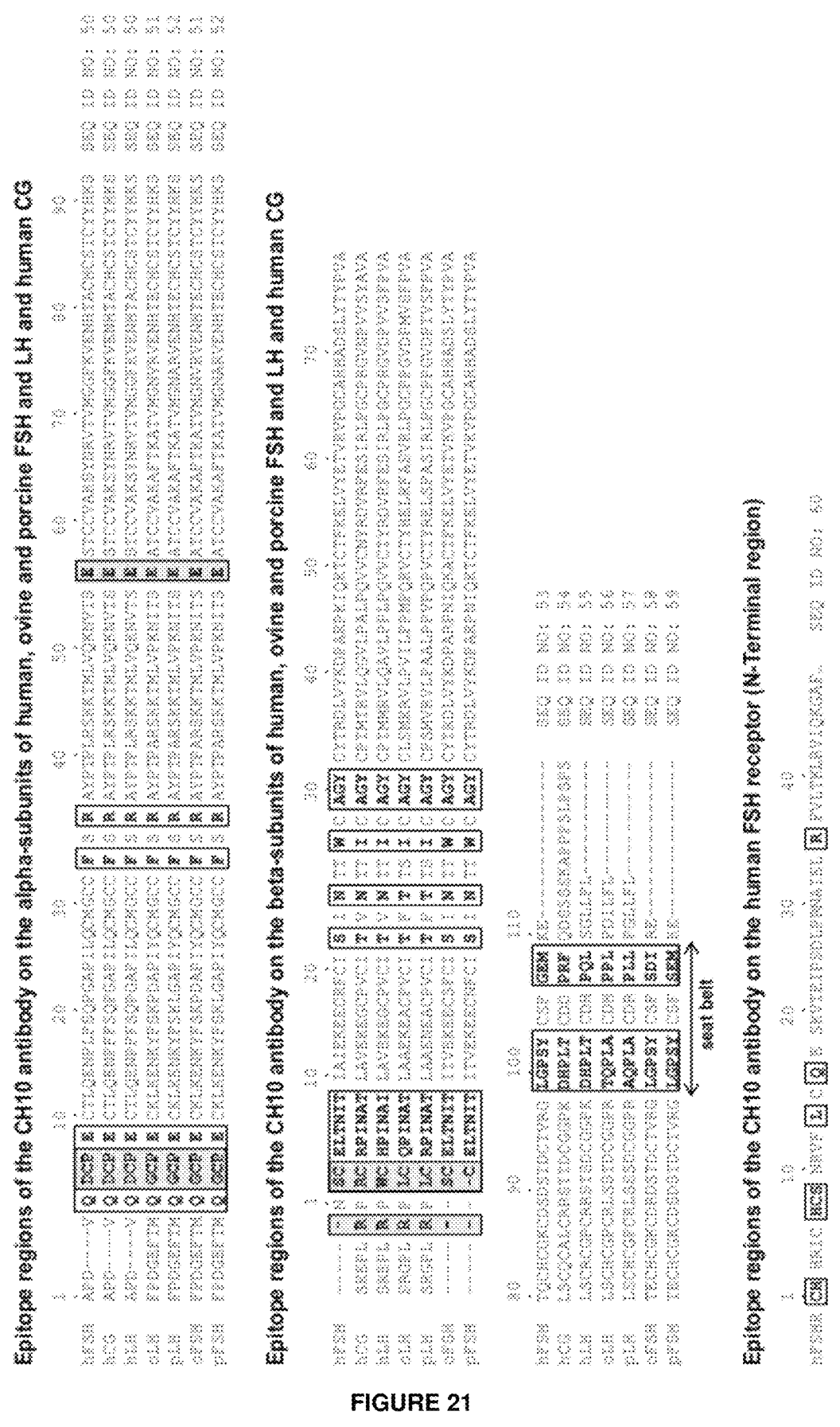

The docking results are shown in FIG. 21. It appears that the CH10 ligand docks similarly on the seven target hormones. The epitope is defined by several regions located discontinuously on the alpha- and beta-subunits of FSH and also involves eight residues of the N-terminal end of the human FSH receptor. The epitope of the CH10 ligand is thus conformational: it consists of several sequential regions of the hormone and of a sequence in the N-terminal end of the FSH receptor. All of these regions are spatially close in the native conformation of the hormone and of the activated receptor.

The various residues of the hormone and of the receptor that are involved in the interface with the CH10 ligand are surrounded by rectangles in FIG. 21. The four residues denoted by a shaded area on the alpha-subunit (Asp6-Cys7-Pro8 and Glu56 on hFSH) and the two residues denoted by a shaded area on the beta-subunit (Ser2-Cys3 on hFSH) are involved in the main interaction and have a major role in the antibody/antigen recognition. Among the other residues involved in the interface, those located on the C-terminal part of the beta-subunit are involved in the region known as the "seat belt", the role of which is to stabilize the association of the alpha/beta dimer of the hormone. It thus appears that the binding of the CH10 ligand to the hormone makes safe the closure of the seat belt and thus contributes to the stability of the dimer, which is essential for the bioactivity of the hormone. Furthermore, the CH10 ligand exhibits major recognition of residue Glu56 on the alpha-subunit, which is involved in the fixing of the "seat belt" on the alpha-subunit.

Another characteristic of the epitope of the CH10 antibody is the involvement of the Cys1-His2, His7-Cys8-Ser9, Lys14, Gln16 and Arg35 residues of the N-terminal region of the human FSH receptor in the interface recognized by the antibody.

TABLE 33

Epitope and paratope of the CH10 ligand. The bolded residues are involved in the main interaction zone

| | | Paratope of the CH10 antibody |
|---|---|---|
| Epitope regions on human FSH | | |
| αFSH | Gln5 Asp6 Cys7 Pro8 Glu9 | VH: FR |
| | Phe33 - Arg35 | VL: CDR3 |
| | Glu56 | VL: CDR3 |
| βFSH | Ser2 Cys3 Glu4 Leu5 Thr6 Asn7 | VH: CDR2-CDR3-FR |
| | Ile8 Thr9 | VL: CDR1 |
| | Ser22 - Asn24 - - Trp27 - Ala29 | VH: CDR2-CDR3-FR |
| | Gly30 Tyr31 | VL: CDR3-FR |
| | Leu99 Gly100 Pro101 Ser102 | VH: CDR3 |

TABLE 33-continued

Epitope and paratope of the CH10 ligand. The bolded residues are involved in the main interaction zone

| | | Paratope of the CH10 antibody |
|---|---|---|
| | Tyr103 - - - Gly107 Glu108 Met109 | VL: CDR1-CDR2-CDR3-FR |
| Epitope regions on the human FSH receptor | | |
| | Cys1 His2 - - - - His7 Cys8 Ser9 | VL: FR |
| | Leu14 - Gln16 | VL: CDR1-FR |
| | Arg35 | VL: CDR1-FR |

Table 33 shows the various regions constituting the epitope of the CH10 ligand and those constituting its paratope.

The CDR2 and CDR3 of the VH chain and the CDR1, CDR2 and CDR3 of the VL chain are involved in the recognition of the hormone, as are some residues of framework 3 of the VH chain and of frameworks 1 and 2 of the VL chain.

The residues involved in the main interaction are recognized by the residues Thr60 of the CDR2, Tyr61-Tyr62-Asp64-Lys67 of framework 3 of the VH chain and residues His92 and Ser93 of the CDR3 of the VL chain.

Only the VL chain is involved in the interaction on the ectodomain of the receptor via its CDR1 and its frameworks 1 and 2.

Example 8: Construction, Production and Characterization of Various Fragments of the CA5 Ligand of the Invention Various fragments of the CA5 antibody were constructed in order to evaluate their capacity to potentiate the biological activity of ovine FSH and human FSH (Gonal-f® Merck Serono). A fragment comprising the light variable chain alone, called "CA5 VL", a fragment comprising the heavy variable chain alone, called "CA5 VH" and a "reverse CA5 scFv" constructed in a reverse VL-VH order compared with the VH-VL sequence (SEQ ID NO: 19 and SEQ ID NO: 20) of the CA5 scFv described in example 1, paragraph 4 of the present invention, were produced.

1/Antibody Fragment Construction and Production

The synthetic genes encoding the CA5 VL and reverse CA5 scFv fragments derived from the CA5 antibody were synthesized by ATG:Biosynthetics GmbH (Germany). The reverse CA5 scFv consists of the CA5 VL of the CA5 scFv-linker-CA5 VH of the CA5 scFv fusion (SEQ ID No 19). Each synthetic gene is designed by the fusion of the sequence of the pSW1 plasmid [7], included between the HindIII site and the end of the sequence encoding the PelB protein, and the sequence of the protein of interest to be synthesized (SEQ ID No 44 and SEQ ID No 48), flanked by the XhoI restriction site. The sequences are inserted between the HindIII and XhoI sites of the pSW1 plasmid. The codons were optimized for expression in E. coli.

The pSW1-CA5 VH expression plasmid was obtained by insertion, into the pSW1 plasmid [7] at the PstI-XhoI sites, of the fragment resulting from the digestion by these same enzymes of the pSW1 reverse CA5 scFv plasmid.

After verification by sequencing of the quality of the constructs, the pSW1-CA5 VL, pSW1-CA5 VH and pSW1 reverse CA5 scFv plasmids were used to transform, by heat shock, HB2151 bacteria (T53040, Interchim, France) made competent [8].

TABLE 34

Nucleotide and peptide sequences of CA5 VL
CA5 VL

| | |
|---|---|
| Nucleotide sequence SEQ ID NO: 44 | GATATTCAGATGACCCAGACCCCGTCAAGCCTGGCGGTGTCAG TCGGCGAAGAGATTACTATGAGCTGTAAAAGCTCGCAGAGCCTG CTGTACTCATCGAACCAGAAAAATTACCTGGCATGGTATCAACA GAAGCCGGGTCAGTCGCCGAAACTGCTGATCTACTGGGCCTCA ACCCGTGAGAGCGGCGTACCGGATCGCTTTACTGGCAGCGGCA GCGGCACGGACTTTACGCTGACGATTAGCTCGGTGAAGGCCGA AGACCTGGCGGTTTATTATTGCCAACAGTACTATAGCTACCCTC GTACCTTCGGCGGCGGCACGAAACTTGAGATTAAACATCACCAT CACCATCACTAA |
| Peptide sequence SEQ ID NO: 45 | DIQMTQTPSSLAVSVGEEITMSCKSSQSLLYSSNQKNYLAWYQQK PGQSPKLLIYWASTRESGVPDRFTGSGSGTDFTLTISSVKAEDLAV YYCQQYYSYPRTFGGGTKLEIKHHHHHH* |

TABLE 35

Nucleotide and peptide sequences of CA5 VH
CA5 VH

| | |
|---|---|
| Nucleotide sequence SEQ ID NO: 46 | CAGGTGCAGCTGCAGCAGTCAGGCGGCGGCCTGGTACAACCT GGTGGCTCACTGCGCCTGAGCTGCGCAACCAGCGGTTTTACCT TTAGCGATTTCTACATGGAATGGGTTCGCCAACCGCCGGGTAAG CGTCTGGAATGGATCGCGGCGAGCCGTAACAAGGCGAAAGATT ATACCACTGAATATAGCGCGTCGGTGAAAGGTCGCTTCATTGTC TCGCGCGATACCAGCCAGTCGATTCTGTATCTGCAAATGAATGC CCTGCGTGCCGAAGACACGGCCATCTACTTCTGTGCGCGTGAT GCACGCTTTGCCTATTGGGGCCAAGGCACCCTGGTGACCGTTA GCGCCCATCACCATCACCATCACTAA |
| Peptide sequence SEQ ID NO: 47 | QVQLQQSGGGLVQPGGSLRLSCATSGFTFSDFYMEWVRQPPGKR LEWIAASRNKAKDYTTEYSASVKGRFIVSRDTSQSILYLQMNALRAE DTAIYFCARDARFAYWGQGTLVTVSAHHHHHH* |

TABLE 36

Nucleotide and peptide sequences of reverse CA5 scFv
Reverse CA5 scFv

| | |
|---|---|
| Nucleotide sequence SEQ ID NO: 48 | GATATTCAGATGACCCAGACCCCGTCAAGCCTGGCGGTGTCAG TCGGCGAAGAGATTACTATGAGCTGTAAAAGCTCGCAGAGCCTG CTGTACTCATCGAACCAGAAAAATTACCTGGCATGGTATCAACA GAAGCCGGGTCAGTCGCCGAAACTGCTGATCTACTGGGCCTCA ACCCGTGAGAGCGGCGTACCGGATCGCTTTACTGGCAGCGGCA GCGGCACGGACTTTACGCTGACGATTAGCTCGGTGAAGGCCGA AGACCTGGCGGTTTATTATTGCCAACAGTACTATAGCTACCCTC GTACCTTCGGCGGCGGCACGAAACTTGAGATTAAAGGTGGTGG CGGTTCAGGTGGTGGCGGTAGCGGTGGCGGTGGCTCACAGGT GCAGCTGCAGCAGTCAGGCGGCGGCCTGGTACAACCTGGTGG CTCACTGCGCCTGAGCTGCGCAACCAGCGGTTTTACCTTTAGCG ATTTCTACATGGAATGGGTTCGCCAACCGCCGGGTAAGCGTCTG GAATGGATCGCGGCGAGCCGTAACAAGGCGAAAGATTATACCA CTGAATATAGCGCGTCGGTGAAAGGTCGCTTCATTGTCTCGCGC GATACCAGCCAGTCGATTCTGTATCTGCAAATGAATGCCCTGCG TGCCGAAGACACGGCCATCTACTTCTGTGCGCGTGATGCACGC TTTGCCTATTGGGGCCAAGGCACCCTGGTGACCGTTAGCGCCC ATCACCATCACCATCACTAA |
| Peptide sequence SEQ ID NO: 49 | DIQMTQTPSSLAVSVGEEITMSCKSSQSLLYSSNQKNYLAWYQQK PGQSPKLLIYWASTRESGVPDRFTGSGSGTDFTLTISSVKAEDLAV YYCQQYYSYPRTFGGGTKLEIKGGGGSGGGGSGGGGSQVQLQQ SGGGLVQPGGSLRLSCATSGFTFSDFYMEWVRQPPGKRLEWIAA SRNKAKDYTTEYSASVKGRFIVSRDTSQSILYLQMNALRAEDTAIYF CARDARFAYWGQGTLVTVSAHHHHHH* |

The fragment production was carried out according to the method previously described in example 1 of the present invention.

2/In Vitro Measurement of the Effect of the CA5 VL, CA5 VH and Reverse CA5 scFv Fragments on the Bioactivity of FSH The in vitro effect of the "CA5 VL", "CA5 VH" and "reverse CA5 scFv" fragments on the bioactivity of ovine and human FSH was studied with the HEK 293 cell line stably transfected with the human FSH receptor and the Glosensor® system according to the protocol previously described in example 2 of the present invention. The "CA5 VL" and "CA5 VH" fragments alone or as a mixture were tested at 40 nM each. The reverse CA5 scFv was tested at the concentration of 80 nM, just like the reference CA5 scFv. The ovine FSH and the human FSH (Gonal f®) were tested at 0.1 nM.

Figure 22:
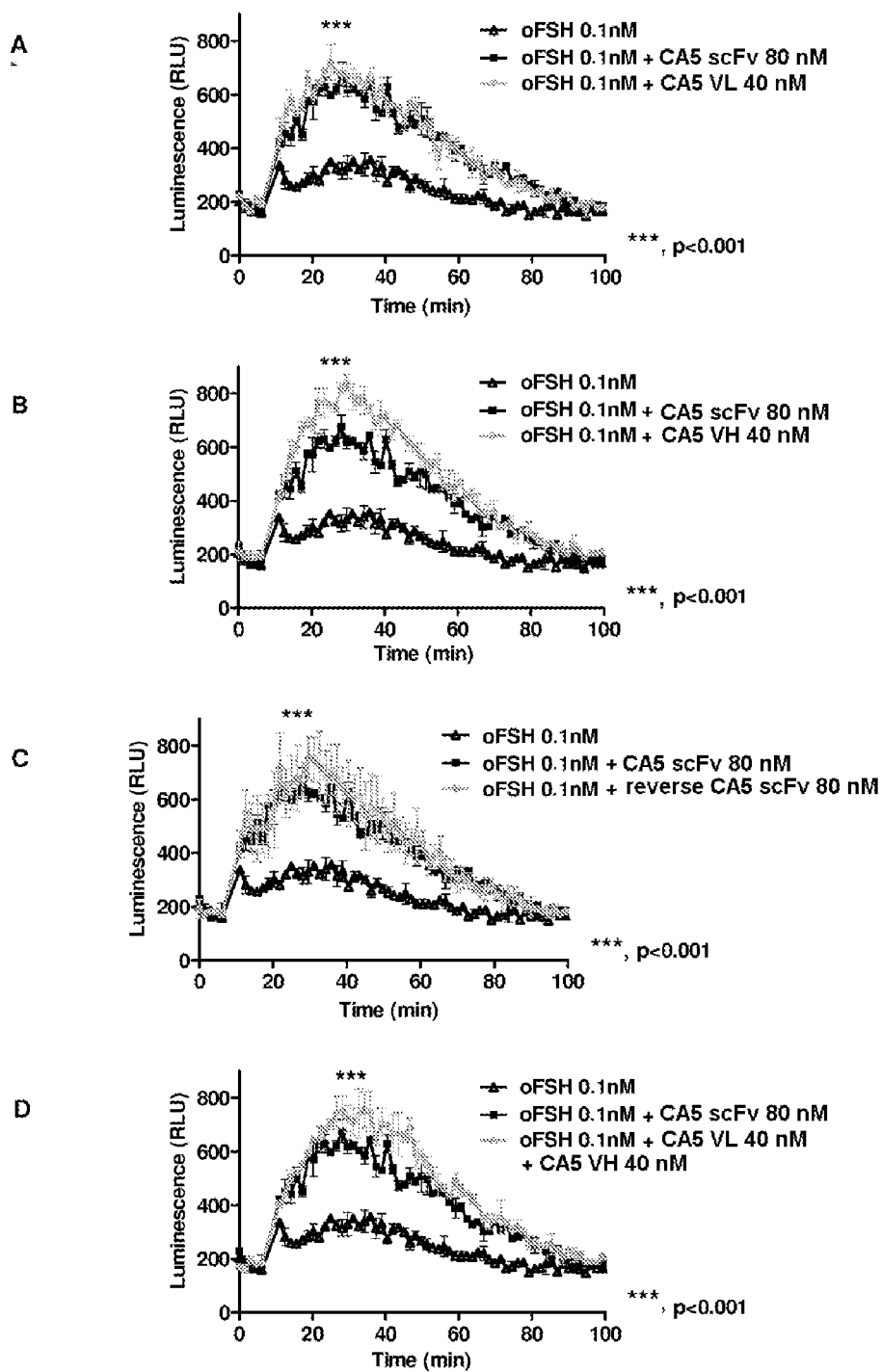
FIG. 22 represents the in vitro potentiating effect of various fragments of the CA5 monoclonal antibody on the bioactivity of ovine FSH and of human FSH.

FIG. 22 shows the cAMP production kinetics curves expressed in relative luminescence units as a function of time (in minutes) obtained in the presence of 0.1 nM of ovine FSH (oFSH) alone or complexed with the various CA5 fragments. Four conditions were compared with oFSH alone: the oFSH+CA5 VL complex (FIG. 22A), the oFSH+CA5 VH complex (FIG. 22B), the oFSH+reverse CA5 scFv complex (FIG. 22C) and finally the complex of oFSH with an equimolar mixture of 40 nM of CA5 VL and of 40 nM of CA5 VH (FIG. 22D). It is observed that, in all cases, a very significant potentiating effect is obtained ($p<0.001$), increasing the cell response to 30 mn of stimulation by a factor of 2.1 to 2.4 times compared with the response induced by FSH alone. These results indicate that the VH and VL fragments alone are capable of exerting a potentiating effect on the bioactivity of oFSH in the same way as the whole scFv. They validate the involvement of the two variable chains in the potentiating effect, described in the model of example 7 of the present invention. The CA5 VH+CA5 VL mixture like the reverse CA5 scFv (VL-VH) exerts the same potentiating effect as the CA5 scFv of origin (VH-VL).

The same study was carried out with human FSH (Gonal f®) at the concentration of 0.1 nM, alone or complexed with the various CA5 fragments. Four conditions were compared with hFSH alone: the hFSH+CA5 VL complex (FIG. 22E), the hFSH+CA5 VH complex (FIG. 22F), the hFSH+reverse CA5 scFv complex (FIG. 22G) and finally the complex of hFSH with an equimolar mixture of 40 nM of CA5 VL and of 40 nM of CA5 VH (FIG. 22H). It is observed that the "CA5 VL" fragment at the concentration of 40 nM complexed with hFSH does not exert a significant potentiating effect, contrary to the "CA5 VH" fragment which very significantly ($p<0.001$) amplifies the maximum cell response of 225% in a manner comparable to CA5 scFv (275% increase) compared with a stimulation with hFSH alone (FIGS. 22E and 22F). Likewise, the reverse CA5 scFv "CA5 VL-VH" (FIG. 22G) and the mixture of the two VH+VL chains (FIG. 22H), complexed with hFSH, induce a significant increase ($p<0.001$) in the cell response of 225% and 230% respectively, close to that obtained with the CA5 scFv complexed with hFSH (increase between 250% and 260%). These results indicate that the CA5 VL+CA5 VH mixture just like the reverse CA5 scFv, complexed with hFSH, induces a significant potentiating effect close to that induced by the reference CA5 scFv. Only the VH fragment exerts a significant potentiating effect on hFSH in this test, unlike CA5 VL.

3/In Vivo Measurement of the Potentiating Effect of the CA5 VL, CA5 VH and Reverse CA5 scFv Fragments on the Bioactivity of FSH in the Female Rat After having been characterized in vitro, the potentiating effect of the various CA5 fragments was characterized in vivo, in the female rat, in order to characterize their effect on the bioactivity of FSH.

In order to measure the FSH bioactivity, the protocol used was that of the biological assay of Steelman and Pohley (Steelman SL, Pohley FM. Endocrinology, 53: 604-616. 1953) [12] as described in example 3 of the present invention.

Figure 23:
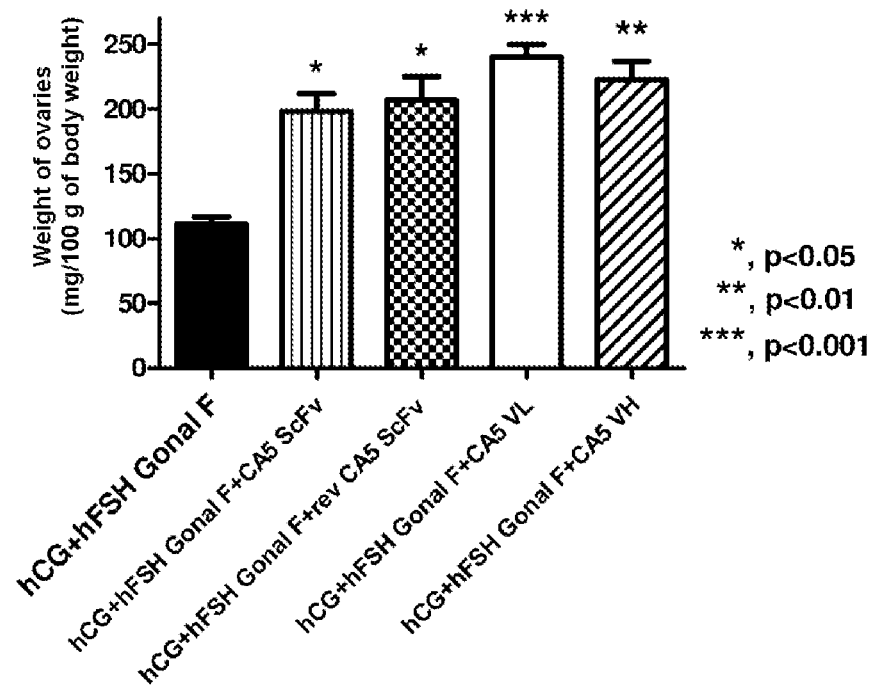
FIG. 23 represents the in vivo potentiating effect, in the female rat, of various fragments of the CA5 monoclonal antibody on the bioactivity of human FSH.

FIG. 23 illustrates the effect of the various fragments of the bioactivity of hFSH. Each batch comprised five female rats. The batch treated with hFSH complexed with the reverse CA5 scFv gave a mean weight of the ovaries of 210 mg, identical to that of the batch treated with the CA5 scFv complexed with hFSH (200 mg), that is to say an increase of 190% compared with the batch having received the hormonal treatment alone ($p<0.05$). The batches treated with the CA5 VL or CA5 VH fragments complexed with hFSH had a mean weight of the ovaries of 240 mg and 230 mg respectively, that is to say an increase of 218% and 209% respectively compared with the batch having received the hormonal treatment alone ($p<0.001$ and $p<0.01$ respectively).

These results demonstrate significantly that the order of construction of the scFv (VL-VH versus VH-VL) complexed with hFSH does not affect the potentiating properties of the scFv on the bioactivity of FSH. These results also demonstrate very significantly that the CA5 VH or CA5 VL chains complexed with the hormone are themselves also capable of potentiating the bioactivity of the hormone. This reflects the respective involvement of the two chains in this effect, as predicted by the interaction model described in example 7 of the present invention.

The invention claimed is:

1. A follicle-stimulating hormone (FSH) ligand which potentiates the bioactivity of FSH, of luteinizing hormone (LH), and of chorionic gonadotropin (CG), wherein said ligand is (A) an antibody or (B) an antibody fragment, and wherein:

when the ligand is the antibody:

the heavy chain variable domain of the antibody contains the following CDRs:

VH-CDR1, consisting of the sequence GFTFSDFY (SEQ ID NO: 9);

VH-CDR2, consisting of the sequence SRNKAKDYTT (SEQ ID NO: 10); and

VH-CDR3, consisting of the sequence ARDARFAY (SEQ ID NO: 11);

and the light chain variable domain of the antibody contains the following CDRs:

VL-CDR1, consisting of the sequence QSLLYSSN-QKNY (SEQ ID NO: 12);

VL-CDR2, consisting of the sequence WAS; and

VL-CDR3, consisting of the sequence QQYYSYPRT (SEQ ID NO: 13);

and when the ligand is the antibody fragment:
the heavy chain variable domain of the antibody fragment contains the following CDRs:
VH-CDR1, consisting of the sequence GFTFSDFY (SEQ ID NO: 9);
VH-CDR2, consisting of the sequence SRNKAKDYTT (SEQ ID NO: 10);
VH-CDR3, consisting of the sequence ARDARFAY (SEQ ID NO: 11); and optionally
the light chain variable domain of the antibody fragment contains the following CDRs:
VL-CDR1, defined by the sequence QSLLYSSN-QKNY (SEQ ID NO: 12);
VL-CDR2, defined by the sequence WAS;
VL-CDR3, defined by the sequence QQYYSYPRT (SEQ ID NO: 13).

2. The ligand as claimed in claim 1, wherein the ligand is chosen from the group consisting of Fab, Fab', F(ab')2, Fv, dsFv, scFv, diabodies, triabodies, tetrabodies, domain $V_HH$, light chain variable domain, and heavy chain variable domain.

3. The ligand as claimed in claim 2, characterized in that the peptide sequence of the scFv is the sequence SEQ ID NO: 20.

4. The ligand as claimed in claim 1, characterized in that the ligand is the CA5 monoclonal antibody produced by the CNCM I-4801 hybridoma.

5. A pharmaceutical composition comprising a ligand as claimed in claim 1, and a pharmaceutically acceptable carrier.

6. The pharmaceutical composition as claimed in claim 5, further comprising an FSH, an LH and/or a CG.

7. A ligand-gonadotropin complex chosen from:
a complex of a ligand as claimed in claim 1 with FSH; or
a complex of a ligand as claimed in claim 1 with LH or the chorionic gonadotropin (CG) hormone.

8. A pharmaceutical composition comprising a complex as claimed in claim 7, and a pharmaceutically acceptable carrier.

9. The pharmaceutical composition as claimed in claim 8, further comprising an FSH, an LH and/or a CG.

10. A follicle-stimulating hormone (FSH) ligand which potentiates the bioactivity of FSH, of luteinizing hormone (LH), and of chorionic gonadotropin (CG),
wherein said ligand is (A) an antibody or (B) an antibody fragment, and
wherein:
when the ligand is the antibody:
the heavy chain variable domain of the antibody contains the sequence SEQ ID NO: 2 or 47; and
the light chain variable domain of the antibody contains the sequence SEQ ID NO: 4 or 45; and
when the ligand is the antibody fragment
the heavy chain variable domain of the antibody fragment contains the sequence SEQ ID NO: 2 or 47; and/or
the light chain variable domain of the antibody fragment contains the sequence SEQ ID NO: 4 or 45.

11. A pharmaceutical composition comprising a ligand as claimed in claim 10 and a pharmaceutically acceptable carrier.

12. The pharmaceutical composition as claimed in claim 11, further comprising an FSH, an LH and/or a CG.

13. A ligand-gonadotropin complex chosen from:
a complex of a ligand as claimed in claim 10 with FSH; or
a complex of a ligand as claimed in claim 10 with LH or the chorionic gonadotropin (CG) hormone.

14. A pharmaceutical composition comprising a complex as claimed in claim 13, and a pharmaceutically acceptable carrier.

15. A follicle-stimulating hormone (FSH) ligand which potentiates the bioactivity of FSH, of luteinizing hormone (LH), and of chorionic gonadotropin (CG),
wherein said ligand is (A) an antibody or (B) an antibody fragment, and wherein:
the heavy chain variable domain of the antibody or the antibody fragment contains the following CDRs:
VH-CDR1, consisting of the sequence GFTFNTYA (SEQ ID NO: 14);
VH-CDR2, consisting of the sequence IRSKSNNYAT (SEQ ID NO: 15); and
VH-CDR3, consisting of the sequence VRQDYYGSSYFDY (SEQ ID NO: 16); and
the light chain variable domain of the antibody or the antibody fragment contains the following CDRs:
VL-CDR1, consisting of the sequence QSISDY (SEQ ID NO: 17);
VL-CDR2, consisting of the sequence YAS; and
VL-CDR3, consisting of the sequence QNGHSFPYT (SEQ ID NO: 18).

16. The ligand as claimed in claim 15, characterized in that the ligand is the CH10 monoclonal antibody produced by the CNCM I-4802 hybridoma.

17. The ligand as claimed in claim 15, wherein the ligand is chosen from the group consisting of Fab, Fab', F(ab')2, Fv, dsFv, scFv, diabodies, triabodies, and tetrabodies.

18. The ligand as claimed in claim 17, characterized in that the peptide sequence of the scFv is the sequence SEQ ID NO: 22.

19. A ligand-gonadotropin complex chosen from:
a complex of a ligand as claimed in claim 15 with FSH;
a complex of a ligand as claimed in claim 15 with LH or the chorionic gonadotropin (CG) hormone.

20. A pharmaceutical composition comprising a complex as claimed in claim 19, and a pharmaceutically acceptable carrier.

21. The pharmaceutical composition as claimed in claim 20, further comprising an FSH, an LH and/or a CG.

22. A pharmaceutical composition comprising a ligand as claimed in claim 15, and a pharmaceutically acceptable carrier.

23. The pharmaceutical composition as claimed in claim 22, further comprising an FSH, an LH and/or a CG.

24. A method of inducing ovulation or polyovulation in a female mammal in need thereof, the method comprising administering to the female mammal an effective amount of the ligand of claim 1, 10, or 15 or of the complex of claim 7, 19 or 13, and optionally an FSH, an LH and/or a CG.

25. A method of increasing circulating endogenous progesterone level in a female mammal in need thereof, the method comprising administering to the female mammal an effective amount of the ligand of claim 1, 10, or 15 or of the complex of claim 7, 19 or 13, and optionally an FSH, an LH and/or a CG.

26. A method of treating infertility or hypofertility in a mammal in need thereof, the method comprising administering to the mammal an effective amount of the ligand of claim 1, 10, or 15 or of the complex of claim 7, 19 or 13, and optionally an FSH, an LH and/or a CG.

27. A method of stimulating procreation in a healthy female mammal in need thereof, the method comprising administering to the female mammal an effective amount of the ligand of claim 1, 10, or 15 or of the complex of claim 7, 19 or 13, and optionally an FSH, an LH and/or a CG.

28. A method of reducing the likelihood of infertility or hypofertility in a mammal in need thereof, the method comprising administering to the mammal an effective amount of the ligand of claim 1, 10, or 15 or of the complex of claim 7, 19 or 13, wherein the mammal is not suffering from infertility or hypofertility, and optionally an FSH, an LH and/or a CG.

29. A follicle-stimulating hormone (FSH) ligand which potentiates the bioactivity of FSH, of luteinizing hormone (LH), and of chorionic gonadotropin (CG),
   wherein said ligand is an antibody fragment, and wherein:
   the heavy chain variable domain of the antibody fragment contains the sequence SEQ ID NO: 6; or
   wherein said ligand is an antibody or antibody fragment, and wherein:
   the heavy chain variable domain of the antibody or the antibody fragment contains the sequence SEQ ID NO: 6 and the light chain variable domain of the antibody or the antibody fragment contains the sequence SEQ ID NO: 8.

* * * * *

SEQUENCE LISTING

<160> NUMBER OF SEQ ID NOS: 70

<210> SEQ ID NO 1
<211> LENGTH: 351
<212> TYPE: DNA
<213> ORGANISM: Artificial Sequence
<220> FEATURE:
<223> OTHER INFORMATION: VH CA5

<400> SEQUENCE: 1

```
gaggtgaagc tggtggaatc tggaggaggc ttggtacagc ctgggggttc tctgagactc        60
tcctgtgcaa cttctgggtt caccttcagt gatttctaca tggagtgggt ccgccagcct       120
```

```
ccagggaaga gactggagtg gattgctgca agtagaaaca aagctaagga ttatacaaca      180
gagtacagtg catctgtgaa gggtcggttc atcgtctcca gagacacttc ccaaagcatc      240
ctctaccttc agatgaatgc cctgagagct gaggacactg ccatttattt ctgtgcaaga      300
gatgcaaggt tgcttactg gggccaaggg actctggtca ctgtctctgc a                351

<210> SEQ ID NO 2
<211> LENGTH: 117
<212> TYPE: PRT
<213> ORGANISM: Artificial Sequence
<220> FEATURE:
<223> OTHER INFORMATION: VH CA5

<400> SEQUENCE: 2

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Asp Phe
            20                  25                  30

Tyr Met Glu Trp Val Arg Gln Pro Pro Gly Lys Arg Leu Glu Trp Ile
        35                  40                  45

Ala Ala Ser Arg Asn Lys Ala Lys Asp Tyr Thr Thr Glu Tyr Ser Ala
    50                  55                  60

Ser Val Lys Gly Arg Phe Ile Val Ser Arg Asp Thr Ser Gln Ser Ile
65                  70                  75                  80

Leu Tyr Leu Gln Met Asn Ala Leu Arg Ala Glu Asp Thr Ala Ile Tyr
                85                  90                  95

Phe Cys Ala Arg Asp Ala Arg Phe Ala Tyr Trp Gly Gln Gly Thr Leu
            100                 105                 110

Val Thr Val Ser Ala
        115

<210> SEQ ID NO 3
<211> LENGTH: 339
<212> TYPE: DNA
<213> ORGANISM: Artificial Sequence
<220> FEATURE:
<223> OTHER INFORMATION: VL CA5

<400> SEQUENCE: 3
gacattgtga tgtcacagtc tccatcctcc ctagctgtgt cagttggaga gaagattact      60
atgagctgca agtccagtca gagccttta tatagtagca atcaaaagaa ctacttggcc       120
tggtaccagc agaaaccagg gcagtctcct aaactgctga tttactgggc atccactagg      180
gaatctgggg tccctgatcg cttcacaggc agtggatctg gacagattt cactctcacc       240 atcagcagtg tgaaggctga agacctggca gtttattact gtcagcaata ttatagctat      300
cctcggacgt tcggtggagg caccaagctg gaaatcaaa                             339

<210> SEQ ID NO 4
<211> LENGTH: 113
<212> TYPE: PRT
<213> ORGANISM: Artificial Sequence
<220> FEATURE:
<223> OTHER INFORMATION: VL CA5

<400> SEQUENCE: 4

Asp Ile Val Met Ser Gln Ser Pro Ser Ser Leu Ala Val Ser Val Gly
1               5                   10                  15

Glu Lys Ile Thr Met Ser Cys Lys Ser Ser Gln Ser Leu Leu Tyr Ser
            20                  25                  30
```

```
Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Lys Ala Glu Asp Leu Ala Val Tyr Tyr Cys Gln Gln
                 85                  90                  95

Tyr Tyr Ser Tyr Pro Arg Thr Phe Gly Gly Gly Thr Lys Leu Glu Ile
            100                 105                 110

Lys

<210> SEQ ID NO 5
<211> LENGTH: 366
<212> TYPE: DNA
<213> ORGANISM: Artificial Sequence
<220> FEATURE:
<223> OTHER INFORMATION: VH CH10

<400> SEQUENCE: 5
gaggtgcagc ttgttgagtc tggtggagga ttggtgcagc ctaaagggtc attgaaactc      60
tcatgtgcag cctctggatt cacccttcaat acctacgcca tgaactgggt ccgccaggct   120
ccaggaaagg gtttggaatg ggttgctcgc ataagaagta aaagtaataa ttatgcaaca   180
tattatgccg attcagtgaa agacaggttc accatctcca gagatgattc acaaagcatg   240
ctctatctgc aaatgaacaa cttgaaaact gaggacacag ccatgtatta ctgtgtgaga   300
caggattact acggtagtag ctactttgac tactgggggcc aaggcaccac tctcacagtc   360
tcctca                                                                366

<210> SEQ ID NO 6
<211> LENGTH: 122
<212> TYPE: PRT
<213> ORGANISM: Artificial Sequence
<220> FEATURE:
<223> OTHER INFORMATION: VH CH10

<400> SEQUENCE: 6

Glu Val Gln Leu Val Glu Ser Gly Gly Gly Leu Val Gln Pro Lys Gly
 1               5                  10                  15

Ser Leu Lys Leu Ser Cys Ala Ala Ser Gly Phe Thr Phe Asn Thr Tyr
             20                  25                  30

Ala Met Asn Trp Val Arg Gln Ala Pro Gly Lys Gly Leu Glu Trp Val
         35                  40                  45

Ala Arg Ile Arg Ser Lys Ser Asn Asn Tyr Ala Thr Tyr Tyr Ala Asp
 50                  55                  60

Ser Val Lys Asp Arg Phe Thr Ile Ser Arg Asp Asp Ser Gln Ser Met
 65                  70                  75                  80

Leu Tyr Leu Gln Met Asn Asn Leu Lys Thr Glu Asp Thr Ala Met Tyr
                 85                  90                  95

Tyr Cys Val Arg Gln Asp Tyr Tyr Gly Ser Ser Tyr Phe Asp Tyr Trp
            100                 105                 110

Gly Gln Gly Thr Thr Leu Thr Val Ser Ser
            115                 120

<210> SEQ ID NO 7
<211> LENGTH: 321
```

<212> TYPE: DNA
<213> ORGANISM: Artificial Sequence
<220> FEATURE:
<223> OTHER INFORMATION: VL CH10

<400> SEQUENCE: 7

```
gacattgtga tgactcagtc tccagccacc ctgtctgtga ctccaggaga tagagtctct    60
ctttcctgca gggccagcca gagtattagc gactacttac actggtatca acaaaaatca   120
catgagtctc caaggcttct catcaaatat gcttcccaat ccatctctgg gatcccctcc   180
aggttcagtg gcagtggatc agggtcagat ttcactctca gtatcaacag tgtggaacct   240
gaagatgttg gagtgtatta ctgtcaaaat ggtcacagct ttccgtacac gttcggaggg   300
gggaccaagc tggaaataaa a                                             321
```

<210> SEQ ID NO 8
<211> LENGTH: 107
<212> TYPE: PRT
<213> ORGANISM: Artificial Sequence
<220> FEATURE:
<223> OTHER INFORMATION: VL CH10

<400> SEQUENCE: 8

```
Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Tyr
                85                  90                  95

Thr Phe Gly Gly Gly Thr Lys Leu Glu Ile Lys
            100                 105
```

<210> SEQ ID NO 9
<211> LENGTH: 8
<212> TYPE: PRT
<213> ORGANISM: Artificial Sequence
<220> FEATURE:
<223> OTHER INFORMATION: VH-CDR1 CA5

<400> SEQUENCE: 9

```
Gly Phe Thr Phe Ser Asp Phe Tyr
1               5
```

<210> SEQ ID NO 10
<211> LENGTH: 10
<212> TYPE: PRT
<213> ORGANISM: Artificial Sequence
<220> FEATURE:
<223> OTHER INFORMATION: VH-CDR2 CA5

<400> SEQUENCE: 10

```
Ser Arg Asn Lys Ala Lys Asp Tyr Thr Thr
1               5                   10
```

<210> SEQ ID NO 11
<211> LENGTH: 8

```
<212> TYPE: PRT
<213> ORGANISM: Artificial Sequence
<220> FEATURE:
<223> OTHER INFORMATION: VH-CDR3 CA5

<400> SEQUENCE: 11

Ala Arg Asp Ala Arg Phe Ala Tyr
1               5

<210> SEQ ID NO 12
<211> LENGTH: 12
<212> TYPE: PRT
<213> ORGANISM: Artificial Sequence
<220> FEATURE:
<223> OTHER INFORMATION: VL-CDR1 CA5

<400> SEQUENCE: 12

Gln Ser Leu Leu Tyr Ser Ser Asn Gln Lys Asn Tyr
1               5                   10

<210> SEQ ID NO 13
<211> LENGTH: 9
<212> TYPE: PRT
<213> ORGANISM: Artificial Sequence
<220> FEATURE:
<223> OTHER INFORMATION: VL-CDR3 CA5

<400> SEQUENCE: 13

Gln Gln Tyr Tyr Ser Tyr Pro Arg Thr
1               5

<210> SEQ ID NO 14
<211> LENGTH: 8
<212> TYPE: PRT
<213> ORGANISM: Artificial Sequence
<220> FEATURE:
<223> OTHER INFORMATION: VH-CDR1 CH10

<400> SEQUENCE: 14

Gly Phe Thr Phe Asn Thr Tyr Ala
1               5

<210> SEQ ID NO 15
<211> LENGTH: 10
<212> TYPE: PRT
<213> ORGANISM: Artificial Sequence
<220> FEATURE:
<223> OTHER INFORMATION: VH-CDR2 CH10

<400> SEQUENCE: 15

Ile Arg Ser Lys Ser Asn Asn Tyr Ala Thr
1               5                   10

<210> SEQ ID NO 16
<211> LENGTH: 13
<212> TYPE: PRT
<213> ORGANISM: Artificial Sequence
<220> FEATURE:
<223> OTHER INFORMATION: VH-CDR3 CH10

<400> SEQUENCE: 16

Val Arg Gln Asp Tyr Tyr Gly Ser Ser Tyr Phe Asp Tyr
1               5                   10

<210> SEQ ID NO 17
<211> LENGTH: 6
<212> TYPE: PRT
```

```
<213> ORGANISM: Artificial Sequence
<220> FEATURE:
<223> OTHER INFORMATION: VL-CDR1 CH10

<400> SEQUENCE: 17

Gln Ser Ile Ser Asp Tyr
1               5

<210> SEQ ID NO 18
<211> LENGTH: 9
<212> TYPE: PRT
<213> ORGANISM: Artificial Sequence
<220> FEATURE:
<223> OTHER INFORMATION: VL-CDR3 CH10

<400> SEQUENCE: 18

Gln Asn Gly His Ser Phe Pro Tyr Thr
1               5

<210> SEQ ID NO 19
<211> LENGTH: 771
<212> TYPE: DNA
<213> ORGANISM: Artificial Sequence
<220> FEATURE:
<223> OTHER INFORMATION: scFv CA5

<400> SEQUENCE: 19
caggtgcagc tgcagcagtc aggcggcggc ctggtacaac tggtggctc actgcgcctg      60 agctgcgcaa ccagcggttt tacctttagc gatttctaca tggaatgggt tcgccaaccg    120
ccgggtaagc gtctggaatg gatcgcggcg agccgtaaca aggcgaaaga ttataccact    180
gaatatagcg cgtcggtgaa aggtcgcttc attgtctcgc gcgataccag ccagtcgatt    240
ctgtatctgc aaatgaatgc cctgcgtgcc gaagacacgg ccatctactt ctgtgcgcgt    300
gatgcacgct ttgcctattg gggccaaggc accctggtga ccgttagcgc cggtggtggc    360
ggttcaggtg gtggcggtag cggtggcggt ggctcagata ttcagatgac ccagaccccg    420
tcaagcctgg cggtgtcagt cggcgaagag attactatga gctgtaaaag ctcgcagagc    480
ctgctgtact catcgaacca gaaaaattac ctggcatggt atcaacagaa gccgggtcag    540
tcgccgaaac tgctgatcta ctgggcctca acccgtgaga gcggcgtacc ggatcgcttt    600
actggcagcg gcagcggcac ggactttacg ctgacgatta gctcggtgaa ggccgaagac    660
ctggcggttt attattgcca acagtactat agctacccctc gtaccttcgg cggcggcacg    720
aaactcgaga ttaaacatca ccatcaccat cactaactcg agatcaagta a              771

<210> SEQ ID NO 20
<211> LENGTH: 251
<212> TYPE: PRT
<213> ORGANISM: Artificial Sequence
<220> FEATURE:
<223> OTHER INFORMATION: scFv CA5

<400> SEQUENCE: 20

Gln Val Gln Leu Gln Gln Ser Gly Gly Gly Leu Val Gln Pro Gly Gly
1               5                   10                  15

Ser Leu Arg Leu Ser Cys Ala Thr Ser Gly Phe Thr Phe Ser Asp Phe
                20                  25                  30

Tyr Met Glu Trp Val Arg Gln Pro Pro Gly Lys Arg Leu Glu Trp Ile
            35                  40                  45

Ala Ala Ser Arg Asn Lys Ala Lys Asp Tyr Thr Thr Glu Tyr Ser Ala
        50                  55                  60
```

-continued

```
Ser Val Lys Gly Arg Phe Ile Val Ser Arg Asp Thr Ser Gln Ser Ile
 65                 70                  75                  80

Leu Tyr Leu Gln Met Asn Ala Leu Arg Ala Glu Asp Thr Ala Ile Tyr
                 85                  90                  95

Phe Cys Ala Arg Asp Ala Arg Phe Ala Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Gly Ser Asp Ile Gln Met Thr Gln Thr Pro Ser Ser Leu Ala
    130                 135                 140

Val Ser Val Gly Glu Glu Ile Thr Met Ser Cys Lys Ser Ser Gln Ser
145                 150                 155                 160

Leu Leu Tyr Ser Ser Asn Gln Lys Asn Tyr Leu Ala Trp Tyr Gln Gln
                165                 170                 175

Lys Pro Gly Gln Ser Pro Lys Leu Leu Ile Tyr Trp Ala Ser Thr Arg
            180                 185                 190

Glu Ser Gly Val Pro Asp Arg Phe Thr Gly Ser Gly Ser Gly Thr Asp
        195                 200                 205

Phe Thr Leu Thr Ile Ser Ser Val Lys Ala Glu Asp Leu Ala Val Tyr
    210                 215                 220

Tyr Cys Gln Gln Tyr Tyr Ser Tyr Pro Arg Thr Phe Gly Gly Gly Thr
225                 230                 235                 240

Lys Leu Glu Ile Lys His His His His His
                245                 250
```

<210> SEQ ID NO 21
<211> LENGTH: 768
<212> TYPE: DNA
<213> ORGANISM: Artificial Sequence
<220> FEATURE:
<223> OTHER INFORMATION: scFv CH10

<400> SEQUENCE: 21

```
caggtgcagc tgcagcaatc aggcggcggc ctggtccaac cgaaaggtag cctgaaactg      60
tcgtgcgccg ccagcggctt tacgttcaac acttacgcga tgaattgggt gcgtcaggcg     120
cctggtaaag gcctggaatg ggtggcacgc atccgttcaa aagcaacaa ttacgcgacg     180
tattatgcag acagcgtaaa agatcgcttt accatcagcc gtgatgattc acagtcaatg     240
ctgtacctgc aaatgaataa cctgaaaact gaagacactg cgatgtatta ttgtgttcgc     300
caggactatt acggtagctc gtatttcgat tactggggcc aaggcaccac cctgacggtg     360
agctcgggtg gcggtggctc aggtggtggt ggtagcggcg gtggcggtag cgatatccag     420
atgacccaga ccccggcaac cctgagcgtt accctggtg accgcgtttc gctgagctgc     480
cgtgcctcgc agagcatttc ggactatctg cactggtatc agcaaaaatc acacgaatca     540
ccgcgtctgc tgattaagta cgccagccaa tcgattagcg gtattccgag ccgcttttcg     600
ggctcgggtt cgggctcgga ttttacctg tcaattaata gcgtagagcc ggaagatgta     660
ggcgtctact attgtcagaa cggccattca ttcccgtaca cgtttggcgg cggcaccaag     720
ctcgagatta agcatcacca tcatcaccat taactcgaga tcaagtaa                  768
```

<210> SEQ ID NO 22
<211> LENGTH: 250
<212> TYPE: PRT
<213> ORGANISM: Artificial Sequence
<220> FEATURE:

<223> OTHER INFORMATION: scFv CH10

<400> SEQUENCE: 22

```
Gln Val Gln Leu Gln Gln Ser Gly Gly Gly Leu Val Gln Pro Lys Gly
1               5                   10                  15
Ser Leu Lys Leu Ser Cys Ala Ala Ser Gly Phe Thr Phe Asn Thr Tyr
            20                  25                  30
Ala Met Asn Trp Val Arg Gln Ala Pro Gly Lys Gly Leu Glu Trp Val
        35                  40                  45
Ala Arg Ile Arg Ser Lys Ser Asn Asn Tyr Ala Thr Tyr Tyr Ala Asp
    50                  55                  60
Ser Val Lys Asp Arg Phe Thr Ile Ser Arg Asp Asp Ser Gln Ser Met
65                  70                  75                  80
Leu Tyr Leu Gln Met Asn Asn Leu Lys Thr Glu Asp Thr Ala Met Tyr
                85                  90                  95
Tyr Cys Val Arg Gln Asp Tyr Tyr Gly Ser Ser Tyr Phe Asp Tyr Trp
            100                 105                 110
Gly Gln Gly Thr Thr Leu Thr Val Ser Ser Gly Gly Gly Gly Ser Gly
        115                 120                 125
Gly Gly Gly Ser Gly Gly Gly Ser Asp Ile Gln Met Thr Gln Thr
    130                 135                 140
Pro Ala Thr Leu Ser Val Thr Pro Gly Asp Arg Val Ser Leu Ser Cys
145                 150                 155                 160
Arg Ala Ser Gln Ser Ile Ser Asp Tyr Leu His Trp Tyr Gln Gln Lys
                165                 170                 175
Ser His Glu Ser Pro Arg Leu Leu Ile Lys Tyr Ala Ser Gln Ser Ile
            180                 185                 190
Ser Gly Ile Pro Ser Arg Phe Ser Gly Ser Gly Ser Gly Ser Asp Phe
        195                 200                 205
Thr Leu Ser Ile Asn Ser Val Glu Pro Glu Asp Val Gly Val Tyr Tyr
    210                 215                 220
Cys Gln Asn Gly His Ser Phe Pro Tyr Thr Phe Gly Gly Gly Thr Lys
225                 230                 235                 240
Leu Glu Ile Lys His His His His His His
                245                 250
```

<210> SEQ ID NO 23
<211> LENGTH: 35
<212> TYPE: DNA
<213> ORGANISM: Artificial Sequence
<220> FEATURE:
<223> OTHER INFORMATION: VHRev1

<400> SEQUENCE: 23
cgggatcctc tagaggtcca actgcaggag tcagg       35

<210> SEQ ID NO 24
<211> LENGTH: 19
<212> TYPE: DNA
<213> ORGANISM: Artificial Sequence
<220> FEATURE:
<223> OTHER INFORMATION: VHFor

<400> SEQUENCE: 24
caggggccag tggatagac       19

<210> SEQ ID NO 25
<211> LENGTH: 21

```
<212> TYPE: DNA
<213> ORGANISM: Artificial Sequence
<220> FEATURE:
<223> OTHER INFORMATION: MKRev5

<400> SEQUENCE: 25
gacattgtga tgacccagtc t                                              21

<210> SEQ ID NO 26
<211> LENGTH: 21
<212> TYPE: DNA
<213> ORGANISM: Artificial Sequence
<220> FEATURE:
<223> OTHER INFORMATION: MKC5For

<400> SEQUENCE: 26
ggatacagtt ggtgcagcat c                                              21

<210> SEQ ID NO 27
<211> LENGTH: 22
<212> TYPE: DNA
<213> ORGANISM: Artificial Sequence
<220> FEATURE:
<223> OTHER INFORMATION: CA5VH_Fw

<400> SEQUENCE: 27
cacttttaca tggtatccag tg                                             22

<210> SEQ ID NO 28
<211> LENGTH: 23
<212> TYPE: DNA
<213> ORGANISM: Artificial Sequence
<220> FEATURE:
<223> OTHER INFORMATION: CA5VH_Rev

<400> SEQUENCE: 28
gtttctactt gcagcaatcc act                                            23

<210> SEQ ID NO 29
<211> LENGTH: 19
<212> TYPE: DNA
<213> ORGANISM: Artificial Sequence
<220> FEATURE:
<223> OTHER INFORMATION: CA5VL_Fw
<220> FEATURE:
<221> NAME/KEY: misc_feature
<222> LOCATION: (3)..(3)
<223> OTHER INFORMATION: W = A ou T
<220> FEATURE:
<221> NAME/KEY: misc_feature
<222> LOCATION: (10)..(10)
<223> OTHER INFORMATION: R = G ou A
<220> FEATURE:
<221> NAME/KEY: misc_feature
<222> LOCATION: (18)..(18)
<223> OTHER INFORMATION: Y = T ou C

<400> SEQUENCE: 29
gawtcacagr cccaggtyc                                                 19

<210> SEQ ID NO 30
<211> LENGTH: 23
<212> TYPE: DNA
<213> ORGANISM: Artificial Sequence
<220> FEATURE:
<223> OTHER INFORMATION: CA5VL_Rev

<400> SEQUENCE: 30
```
cccagtaaat cagcagttta gga    23

<210> SEQ ID NO 31
<211> LENGTH: 20
<212> TYPE: DNA
<213> ORGANISM: Artificial Sequence
<220> FEATURE:
<223> OTHER INFORMATION: MuCFor

<400> SEQUENCE: 31
ggggaagaca tttgggaagg    20

<210> SEQ ID NO 32
<211> LENGTH: 21
<212> TYPE: DNA
<213> ORGANISM: Artificial Sequence
<220> FEATURE:
<223> OTHER INFORMATION: MKRev2

<400> SEQUENCE: 32
gatattgtga tgacgcaggc t    21

<210> SEQ ID NO 33
<211> LENGTH: 18
<212> TYPE: DNA
<213> ORGANISM: Artificial Sequence
<220> FEATURE:
<223> OTHER INFORMATION: MKRev3

<400> SEQUENCE: 33
gatattgtga taacccag    18

<210> SEQ ID NO 34
<211> LENGTH: 21
<212> TYPE: DNA
<213> ORGANISM: Artificial Sequence
<220> FEATURE:
<223> OTHER INFORMATION: MKRev4

<400> SEQUENCE: 34
gacattgtgc tgacccaatc t    21

<210> SEQ ID NO 35
<211> LENGTH: 21
<212> TYPE: DNA
<213> ORGANISM: Artificial Sequence
<220> FEATURE:
<223> OTHER INFORMATION: MKRev6

<400> SEQUENCE: 35
gatattgtgc taactcagtc t    21

<210> SEQ ID NO 36
<211> LENGTH: 21
<212> TYPE: DNA
<213> ORGANISM: Artificial Sequence
<220> FEATURE:
<223> OTHER INFORMATION: MKRev8

<400> SEQUENCE: 36
gacatccagc tgactcagtc t    21

<210> SEQ ID NO 37
<211> LENGTH: 21
<212> TYPE: DNA
<213> ORGANISM: Artificial Sequence
<220> FEATURE:
<223> OTHER INFORMATION: MKC5for

<400> SEQUENCE: 37
ggatacagtt ggtgcagcat c                                          21

<210> SEQ ID NO 38
<211> LENGTH: 20
<212> TYPE: DNA
<213> ORGANISM: Artificial Sequence
<220> FEATURE:
<223> OTHER INFORMATION: CH10VH_Fw

<400> SEQUENCE: 38
atggtgttgg ggctgaagtg                                            20

<210> SEQ ID NO 39
<211> LENGTH: 22
<212> TYPE: DNA
<213> ORGANISM: Artificial Sequence
<220> FEATURE:
<223> OTHER INFORMATION: CH10VH_Rev

<400> SEQUENCE: 39
cagttcatgg cgtaggtatt ga                                         22

<210> SEQ ID NO 40
<211> LENGTH: 20
<212> TYPE: DNA
<213> ORGANISM: Artificial Sequence
<220> FEATURE:
<223> OTHER INFORMATION: CH10VL_Fw

<400> SEQUENCE: 40
ttctggaytt cagcctccag                                            20

<210> SEQ ID NO 41
<211> LENGTH: 23
<212> TYPE: DNA
<213> ORGANISM: Artificial Sequence
<220> FEATURE:
<223> OTHER INFORMATION: CH10VL_Rev

<400> SEQUENCE: 41
gattgggaag catatttgat gag                                        23

<210> SEQ ID NO 42
<211> LENGTH: 14
<212> TYPE: PRT
<213> ORGANISM: Artificial Sequence
<220> FEATURE:
<223> OTHER INFORMATION: Lieur

<400> SEQUENCE: 42

Gly Gly Gly Gly Ser Gly Gly Gly Ser Gly Gly Gly Ser
1               5                   10

<210> SEQ ID NO 43
<211> LENGTH: 16
<212> TYPE: PRT
<213> ORGANISM: Artificial Sequence
<220> FEATURE:
<223> OTHER INFORMATION: Fragment VL de scFv

<400> SEQUENCE: 43

Leu Glu Ile Lys His His His His His His Leu Glu Ile Lys Val Asp

<210> SEQ ID NO 44
<211> LENGTH: 360
<212> TYPE: DNA
<213> ORGANISM: Artificial Sequence
<220> FEATURE:
<223> OTHER INFORMATION: VL CA5

<400> SEQUENCE: 44

```
gatattcaga tgacccagac cccgtcaagc ctggcggtgt cagtcggcga agagattact      60
atgagctgta aaagctcgca gagcctgctg tactcatcga accagaaaaa ttacctggca     120
tggtatcaac agaagccggg tcagtcgccg aaactgctga tctactgggc ctcaacccgt     180
gagagcggcg taccggatcg ctttactggc agcggcagcg gcacggactt tacgctgacg     240
attagctcgg tgaaggccga agacctggcg gtttattatt gccaacagta ctatagctac     300
cctcgtacct tcggcggcgg cacgaaactt gagattaaac atcaccatca ccatcactaa     360
```

<210> SEQ ID NO 45
<211> LENGTH: 119
<212> TYPE: PRT
<213> ORGANISM: Artificial Sequence
<220> FEATURE:
<223> OTHER INFORMATION: VL CA5

<400> SEQUENCE: 45

Asp Ile Gln Met Thr Gln Thr Pro Ser Ser Leu Ala Val Ser Val Gly
1               5                   10                  15

Glu Glu Ile Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Arg Thr Phe Gly Gly Gly Thr Lys Leu Glu Ile
            100                 105                 110

Lys His His His His His
        115

<210> SEQ ID NO 46
<211> LENGTH: 372
<212> TYPE: DNA
<213> ORGANISM: Artificial Sequence
<220> FEATURE:
<223> OTHER INFORMATION: VH CA5

<400> SEQUENCE: 46

```
caggtgcagc tgcagcagtc aggcggcggc ctggtacaac tggtggctc actgcgcctg       60
agctgcgcaa ccagcggttt tacctttagc gatttctaca tggaatgggt tcgccaaccg     120
ccgggtaagc gtctggaatg gatcgcggcg agccgtaaca aggcgaaaga ttataccact     180
gaatatagcg cgtcggtgaa aggtcgcttc attgtctcgc gcgataccag ccagtcgatt     240
ctgtatctgc aaatgaatgc cctgcgtgcc gaagacacgg ccatctactt ctgtgcgcgt     300
gatgcacgct ttgcctattg gggccaaggc accctggtga ccgttagcgc ccatcaccat     360
```
caccatcact aa     372

<210> SEQ ID NO 47
<211> LENGTH: 123
<212> TYPE: PRT
<213> ORGANISM: Artificial Sequence
<220> FEATURE:
<223> OTHER INFORMATION: VH CA5

<400> SEQUENCE: 47

Gln Val Gln Leu Gln Gln Ser Gly Gly Gly Leu Val Gln Pro Gly Gly
1               5                   10                  15

Ser Leu Arg Leu Ser Cys Ala Thr Ser Gly Phe Thr Phe Ser Asp Phe
            20                  25                  30

Tyr Met Glu Trp Val Arg Gln Pro Gly Lys Arg Leu Glu Trp Ile
        35                  40                  45

Ala Ala Ser Arg Asn Lys Ala Lys Asp Tyr Thr Thr Glu Tyr Ser Ala
    50                  55                  60

Ser Val Lys Gly Arg Phe Ile Val Ser Arg Asp Thr Ser Gln Ser Ile
65                  70                  75                  80

Leu Tyr Leu Gln Met Asn Ala Leu Arg Ala Glu Asp Thr Ala Ile Tyr
                85                  90                  95

Phe Cys Ala Arg Asp Ala Arg Phe Ala Tyr Trp Gly Gln Gly Thr Leu
            100                 105                 110

Val Thr Val Ser Ala His His His His His His
        115                 120

<210> SEQ ID NO 48
<211> LENGTH: 756
<212> TYPE: DNA
<213> ORGANISM: Artificial Sequence
<220> FEATURE:
<223> OTHER INFORMATION: ScFv CA5 inverse

<400> SEQUENCE: 48
gatattcaga tgacccagac cccgtcaagc ctggcggtgt cagtcggcga agagattact     60
atgagctgta aaagctcgca gagcctgctg tactcatcga accagaaaaa ttacctggca    120
tggtatcaac agaagccggg tcagtcgccg aaactgctga tctactgggc ctcaacccgt    180
gagagcggcg taccggatcg ctttactggc agcggcagcg gcacggactt tacgctgacg    240
attagctcgg tgaaggccga agacctggcg gtttattatt gccaacagta ctatagctac    300
cctcgtacct tcggcggcgg cacgaaactt gagattaaag gtggtggcgg ttcaggtggt    360
ggcggtagcg gtggcggtgg ctcacaggtg cagctgcagc agtcaggcgg cggcctggta    420
caacctggtg gctcactgcg cctgagctgc gcaaccagcg gttttacctt tagcgatttc    480
tacatggaat gggttcgcca accgccgggt aagcgtctgg aatggatcgc ggcgagccgt    540
aacaaggcga agattatac cactgaatat agcgcgtcgg tgaaaggtcg cttcattgtc    600
tcgcgcgata ccagccagtc gattctgtat ctgcaaatga atgccctgcg tgccgaagac    660
acggccatct acttctgtgc gcgtgatgca cgctttgcct attggggcca aggcaccctg    720
gtgaccgtta gcgcccatca ccatcaccat cactaa                             756

<210> SEQ ID NO 49
<211> LENGTH: 251
<212> TYPE: PRT
<213> ORGANISM: Artificial Sequence
<220> FEATURE:

<223> OTHER INFORMATION: ScFv CA5 inverse

<400> SEQUENCE: 49

Asp Ile Gln Met Thr Gln Thr Pro Ser Ser Leu Ala Val Ser Val Gly
1               5                   10                  15

Glu Glu Ile Thr Met Ser Cys Lys Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Arg Thr Phe Gly Gly Gly Thr Lys Leu Glu Ile
            100                 105                 110

Lys Gly Gly Gly Gly Ser Gly Gly Gly Gly Ser Gly Gly Gly Gly Ser
        115                 120                 125

Gln Val Gln Leu Gln Gln Ser Gly Gly Gly Leu Val Gln Pro Gly Gly
    130                 135                 140

Ser Leu Arg Leu Ser Cys Ala Thr Ser Gly Phe Thr Phe Ser Asp Phe
145                 150                 155                 160

Tyr Met Glu Trp Val Arg Gln Pro Pro Gly Lys Arg Leu Glu Trp Ile
                165                 170                 175

Ala Ala Ser Arg Asn Lys Ala Lys Asp Tyr Thr Thr Glu Tyr Ser Ala
            180                 185                 190

Ser Val Lys Gly Arg Phe Ile Val Ser Arg Asp Thr Ser Gln Ser Ile
        195                 200                 205

Leu Tyr Leu Gln Met Asn Ala Leu Arg Ala Glu Asp Thr Ala Ile Tyr
    210                 215                 220

Phe Cys Ala Arg Asp Ala Arg Phe Ala Tyr Trp Gly Gln Gly Thr Leu
225                 230                 235                 240

Val Thr Val Ser Ala His His His His His
                245                 250

<210> SEQ ID NO 50
<211> LENGTH: 92
<212> TYPE: PRT
<213> ORGANISM: Homo sapiens
<220> FEATURE:
<221> NAME/KEY: misc_feature
<223> OTHER INFORMATION: sous-unite alpha hFSH, hCG et hLH
<220> FEATURE:
<221> NAME/KEY: misc_feature
<222> LOCATION: (17)..(17)
<223> OTHER INFORMATION: Xaa = Leu ou Phe

<400> SEQUENCE: 50

Ala Pro Asp Val Gln Asp Cys Pro Glu Cys Thr Leu Gln Glu Asn Pro
1               5                   10                  15

Xaa Phe Ser Gln Pro Gly Ala Pro Ile Leu Gln Cys Met Gly Cys Cys
            20                  25                  30

Phe Ser Arg Ala Tyr Pro Thr Pro Leu Arg Ser Lys Lys Thr Met Leu
        35                  40                  45

Val Gln Lys Asn Val Thr Ser Glu Ser Thr Cys Cys Val Ala Lys Ser
    50                  55                  60

Tyr Asn Arg Val Thr Val Met Gly Gly Phe Lys Val Glu Asn His Thr
65                  70                  75                  80

Ala Cys His Cys Ser Thr Cys Tyr Tyr His Lys Ser
                85                  90

<210> SEQ ID NO 51
<211> LENGTH: 96
<212> TYPE: PRT
<213> ORGANISM: Ovis aries
<220> FEATURE:
<221> NAME/KEY: misc_feature
<223> OTHER INFORMATION: sous-unite alpha oLH et oFSH

<400> SEQUENCE: 51

Phe Pro Asp Gly Glu Phe Thr Met Gln Gly Cys Pro Glu Cys Lys Leu
1               5                   10                  15

Lys Glu Asn Lys Tyr Phe Ser Lys Pro Asp Ala Pro Ile Tyr Gln Cys
            20                  25                  30

Met Gly Cys Cys Phe Ser Arg Ala Tyr Pro Thr Pro Ala Arg Ser Lys
        35                  40                  45

Lys Thr Met Leu Val Pro Lys Asn Ile Thr Ser Glu Ala Thr Cys Cys
    50                  55                  60

Val Ala Lys Ala Phe Thr Lys Ala Thr Val Met Gly Asn Val Arg Val
65                  70                  75                  80

Glu Asn His Thr Glu Cys His Cys Ser Thr Cys Tyr Tyr His Lys Ser
                85                  90                  95

<210> SEQ ID NO 52
<211> LENGTH: 96
<212> TYPE: PRT
<213> ORGANISM: Sus scrofa
<220> FEATURE:
<221> NAME/KEY: misc_feature
<223> OTHER INFORMATION: sous-unite alpha pLH et pFSH

<400> SEQUENCE: 52

Phe Pro Asp Gly Glu Phe Thr Met Gln Gly Cys Pro Glu Cys Lys Leu
1               5                   10                  15

Lys Glu Asn Lys Tyr Phe Ser Lys Leu Gly Ala Pro Ile Tyr Gln Cys
            20                  25                  30

Met Gly Cys Cys Phe Ser Arg Ala Tyr Pro Thr Pro Ala Arg Ser Lys
        35                  40                  45

Lys Thr Met Leu Val Pro Lys Asn Ile Thr Ser Glu Ala Thr Cys Cys
    50                  55                  60

Val Ala Lys Ala Phe Thr Lys Ala Thr Val Met Gly Asn Ala Arg Val
65                  70                  75                  80

Glu Asn His Thr Glu Cys His Cys Ser Thr Cys Tyr Tyr His Lys Ser
                85                  90                  95

<210> SEQ ID NO 53
<211> LENGTH: 111
<212> TYPE: PRT
<213> ORGANISM: Homo sapiens
<220> FEATURE:
<221> NAME/KEY: misc_feature
<223> OTHER INFORMATION: sous-unite beta hFSH

<400> SEQUENCE: 53

Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys 20                  25                  30

Tyr Thr Arg Asp Leu Val Tyr Lys Asp Pro Ala Arg Pro Lys Ile Gln
                35                  40                  45

Lys Thr Cys Thr Phe Lys Glu Leu Val Tyr Glu Thr Val Arg Val Pro
        50                  55                  60

Gly Cys Ala His His Ala Asp Ser Leu Tyr Thr Tyr Pro Val Ala Thr
65                  70                  75                  80

Gln Cys His Cys Gly Lys Cys Asp Ser Asp Ser Thr Asp Cys Thr Val
                85                  90                  95

Arg Gly Leu Gly Pro Ser Tyr Cys Ser Phe Gly Glu Met Lys Glu
            100                 105                 110

<210> SEQ ID NO 54
<211> LENGTH: 132
<212> TYPE: PRT
<213> ORGANISM: Homo sapiens
<220> FEATURE:
<221> NAME/KEY: misc_feature
<223> OTHER INFORMATION: sous-unite beta hCG

<400> SEQUENCE: 54

Ser Lys Glu Pro Leu Arg Pro Arg Cys Arg Pro Ile Asn Ala Thr Leu
1               5                   10                  15

Ala Val Glu Lys Glu Gly Cys Pro Val Cys Ile Thr Val Asn Thr Thr
                20                  25                  30

Ile Cys Ala Gly Tyr Cys Pro Thr Met Thr Arg Val Leu Gln Gly Val
            35                  40                  45

Leu Pro Ala Leu Pro Gln Val Val Cys Asn Tyr Arg Asp Val Arg Phe
        50                  55                  60

Glu Ser Ile Arg Leu Pro Gly Cys Pro Arg Gly Val Asn Pro Val Val
65                  70                  75                  80

Ser Tyr Ala Val Ala Leu Ser Cys Gln Cys Ala Leu Cys Arg Arg Ser
                85                  90                  95

Thr Thr Asp Cys Gly Gly Pro Lys Asp His Pro Leu Thr Cys Asp Asp
            100                 105                 110

Pro Arg Phe Gln Asp Ser Ser Ser Ser Lys Ala Pro Pro Pro Ser Leu
        115                 120                 125

Pro Ser Pro Ser
        130

<210> SEQ ID NO 55
<211> LENGTH: 123
<212> TYPE: PRT
<213> ORGANISM: Homo sapiens
<220> FEATURE:
<221> NAME/KEY: misc_feature
<223> OTHER INFORMATION: sous-unite beta hLH

<400> SEQUENCE: 55

Ser Arg Glu Pro Leu Arg Pro Trp Cys His Pro Ile Asn Ala
1               5                   10                  15

Ile Leu Ala Val Glu Lys Glu Gly Cys Pro Val Cys Ile Thr Val Asn
                20                  25                  30

Thr Thr Ile Cys Ala Gly Tyr Cys Pro Thr Met Met Arg Val Leu Gln
            35                  40                  45

Ala Val Leu Pro Pro Leu Pro Gln Val Val Cys Thr Tyr Arg Asp Val
        50                  55                  60

Arg Phe Glu Ser Ile Arg Leu Pro Gly Cys Pro Arg Gly Val Asp Pro

```
              65                  70                  75                  80
Val Val Ser Phe Pro Val Ala Leu Ser Cys Arg Cys Gly Pro Cys Arg
                    85                  90                  95

Arg Ser Thr Ser Asp Cys Gly Gly Pro Lys Asp His Pro Leu Thr Cys
                    100                 105                 110

Asp His Pro Gln Leu Ser Gly Leu Leu Phe Leu
                    115                 120

<210> SEQ ID NO 56
<211> LENGTH: 121
<212> TYPE: PRT
<213> ORGANISM: Ovis aries
<220> FEATURE:
<221> NAME/KEY: misc_feature
<223> OTHER INFORMATION: sous-unite beta oLH

<400> SEQUENCE: 56

Ser Arg Gly Pro Leu Arg Pro Leu Cys Gln Pro Ile Asn Ala Thr Leu
1               5                   10                  15

Ala Ala Glu Lys Glu Ala Cys Pro Val Cys Ile Thr Phe Thr Thr Ser
                    20                  25                  30

Ile Cys Ala Gly Tyr Cys Leu Ser Met Lys Arg Val Leu Pro Val Ile
                    35                  40                  45

Leu Pro Pro Met Pro Gln Arg Val Cys Thr Tyr His Glu Leu Arg Phe
                50                  55                  60

Ala Ser Val Arg Leu Pro Gly Cys Pro Pro Gly Val Asp Pro Met Val
65                  70                  75                  80

Ser Phe Pro Val Ala Leu Ser Cys His Cys Gly Pro Cys Arg Leu Ser
                    85                  90                  95

Ser Thr Asp Cys Gly Gly Pro Arg Thr Gln Pro Leu Ala Cys Asp His
                    100                 105                 110

Pro Pro Leu Pro Asp Ile Leu Phe Leu
                    115                 120

<210> SEQ ID NO 57
<211> LENGTH: 121
<212> TYPE: PRT
<213> ORGANISM: Sus scrofa
<220> FEATURE:
<221> NAME/KEY: misc_feature
<223> OTHER INFORMATION: sous-unite beta pLH

<400> SEQUENCE: 57

Ser Arg Gly Pro Leu Arg Pro Leu Cys Arg Pro Ile Asn Ala Thr Leu
1               5                   10                  15

Ala Ala Glu Asn Glu Ala Cys Pro Val Cys Ile Thr Phe Thr Thr Ser
                    20                  25                  30

Ile Cys Ala Gly Tyr Cys Pro Ser Met Val Arg Val Leu Pro Ala Ala
                    35                  40                  45

Leu Pro Pro Val Pro Gln Pro Val Cys Thr Tyr Arg Glu Leu Ser Phe
                50                  55                  60

Ala Ser Ile Arg Leu Pro Gly Cys Pro Gly Val Asp Pro Thr Val
65                  70                  75                  80

Ser Phe Pro Val Ala Leu Ser Cys His Cys Gly Pro Cys Arg Leu Ser
                    85                  90                  95

Ser Ser Asp Cys Gly Gly Pro Arg Ala Gln Pro Leu Ala Cys Asp Arg
                    100                 105                 110

Pro Leu Leu Pro Gly Leu Leu Phe Leu
```

<210> SEQ ID NO 58
<211> LENGTH: 110
<212> TYPE: PRT
<213> ORGANISM: Ovis aries
<220> FEATURE:
<221> NAME/KEY: misc_feature
<223> OTHER INFORMATION: sous-unite beta oFSH

<400> SEQUENCE: 58

Ser Cys Glu Leu Thr Asn Ile Thr Ile Thr Val Glu Lys Glu Glu Cys
1               5                   10                  15

Ser Phe Cys Ile Ser Ile Asn Thr Thr Trp Cys Ala Gly Tyr Cys Tyr
            20                  25                  30

Thr Arg Asp Leu Val Tyr Lys Asp Pro Ala Arg Pro Asn Ile Gln Lys
        35                  40                  45

Ala Cys Thr Phe Lys Glu Leu Val Tyr Glu Thr Val Lys Val Pro Gly
    50                  55                  60

Cys Ala His His Ala Asp Ser Leu Tyr Thr Tyr Pro Val Ala Thr Glu
65                  70                  75                  80

Cys His Cys Gly Lys Cys Asp Arg Asp Ser Thr Asp Cys Thr Val Arg
                85                  90                  95

Gly Leu Gly Pro Ser Tyr Cys Ser Phe Ser Asp Ile Arg Glu
            100                 105                 110

<210> SEQ ID NO 59
<211> LENGTH: 109
<212> TYPE: PRT
<213> ORGANISM: Sus scrofa
<220> FEATURE:
<221> NAME/KEY: misc_feature
<223> OTHER INFORMATION: sous-unite beta pFSH

<400> SEQUENCE: 59

Cys Glu Leu Thr Asn Ile Thr Ile Val Lys Glu Glu Cys Gly
1               5                   10                  15

Phe Cys Ile Ser Ile Asn Thr Thr Trp Cys Ala Gly Tyr Cys Tyr Thr
            20                  25                  30

Arg Asp Leu Val Tyr Lys Asp Pro Ala Arg Pro Asn Ile Gln Lys Thr
        35                  40                  45

Cys Thr Phe Lys Glu Leu Val Tyr Glu Thr Val Lys Val Pro Gly Cys
    50                  55                  60

Ala His His Ala Asp Ser Leu Tyr Thr Tyr Pro Val Ala Thr Glu Cys
65                  70                  75                  80

His Cys Gly Lys Cys Asp Ser Asp Ser Thr Asp Cys Thr Val Arg Gly
                85                  90                  95

Leu Gly Pro Ser Tyr Cys Ser Phe Ser Glu Met Lys Glu
            100                 105

<210> SEQ ID NO 60
<211> LENGTH: 49
<212> TYPE: PRT
<213> ORGANISM: Homo sapiens
<220> FEATURE:
<221> NAME/KEY: misc_feature
<223> OTHER INFORMATION: Region N terminale du recepteur de la hFSH

<400> SEQUENCE: 60

Cys His His Arg Ile Cys His Cys Ser Asn Arg Val Phe Leu Cys Gln
1               5                   10                  15

-continued

```
Glu Ser Lys Val Thr Glu Ile Pro Ser Asp Leu Pro Arg Asn Ala Ile
            20                  25                  30

Glu Leu Arg Phe Val Leu Thr Lys Leu Arg Val Ile Gln Lys Gly Ala
        35                  40                  45

Phe

<210> SEQ ID NO 61
<211> LENGTH: 7
<212> TYPE: PRT
<213> ORGANISM: Artificial Sequence
<220> FEATURE:
<223> OTHER INFORMATION: Region epitopique de CA5 sur betaFSH

<400> SEQUENCE: 61

Arg Phe Cys Ile Ser Ile Asn
1               5

<210> SEQ ID NO 62
<211> LENGTH: 6
<212> TYPE: PRT
<213> ORGANISM: Artificial Sequence
<220> FEATURE:
<223> OTHER INFORMATION: Region epitopique de CA5 sur betaFSH

<400> SEQUENCE: 62

Arg Val Pro Gly Cys Ala
1               5

<210> SEQ ID NO 63
<211> LENGTH: 12
<212> TYPE: PRT
<213> ORGANISM: Artificial Sequence
<220> FEATURE:
<223> OTHER INFORMATION: Region epitopique de CA5 sur betaFSH

<400> SEQUENCE: 63

Arg Gly Leu Gly Ser Tyr Cys Ser Phe Gly Glu Met
1               5                   10

<210> SEQ ID NO 64
<211> LENGTH: 5
<212> TYPE: PRT
<213> ORGANISM: Artificial Sequence
<220> FEATURE:
<223> OTHER INFORMATION: Region epitopique de CA5 sur recepteur de la
      hFSH

<400> SEQUENCE: 64

His His Arg Ile His
1               5

<210> SEQ ID NO 65
<211> LENGTH: 4
<212> TYPE: PRT
<213> ORGANISM: Artificial Sequence
<220> FEATURE:
<223> OTHER INFORMATION: Region epitopique de CA5 sur recepteur de la
      hFSH

<400> SEQUENCE: 65

Leu Gln Glu Lys
1

<210> SEQ ID NO 66
<211> LENGTH: 5
```

```
<212> TYPE: PRT
<213> ORGANISM: Artificial Sequence
<220> FEATURE:
<223> OTHER INFORMATION: Region epitopique de CH10 sur alphaFSH

<400> SEQUENCE: 66

Gln Asp Cys Pro Glu
1               5

<210> SEQ ID NO 67
<211> LENGTH: 8
<212> TYPE: PRT
<213> ORGANISM: Artificial Sequence
<220> FEATURE:
<223> OTHER INFORMATION: Region epitopique de CH10 sur betaFSH

<400> SEQUENCE: 67

Ser Cys Glu Leu Thr Asn Ile Thr
1               5

<210> SEQ ID NO 68
<211> LENGTH: 6
<212> TYPE: PRT
<213> ORGANISM: Artificial Sequence
<220> FEATURE:
<223> OTHER INFORMATION: Region epitopique de CH10 sur betaFSH

<400> SEQUENCE: 68

Ser Asn Trp Ala Gly Tyr
1               5

<210> SEQ ID NO 69
<211> LENGTH: 8
<212> TYPE: PRT
<213> ORGANISM: Artificial Sequence
<220> FEATURE:
<223> OTHER INFORMATION: Region epitopique de CH10 sur betaFSH

<400> SEQUENCE: 69

Leu Gly Pro Ser Tyr Gly Glu Met
1               5

<210> SEQ ID NO 70
<211> LENGTH: 5
<212> TYPE: PRT
<213> ORGANISM: Artificial Sequence
<220> FEATURE:
<223> OTHER INFORMATION: Region epitopique de CH10 sur recepteur de la
      hFSH

<400> SEQUENCE: 70

Cys His His Cys Ser
1               5
```